United States Patent [19]

Fischman et al.

[11] Patent Number: 5,792,444
[45] Date of Patent: Aug. 11, 1998

[54] LABELED CHEMOTACTIC PEPTIDES TO IMAGE FOCAL SITES OF INFECTION OR INFLAMMATION

[75] Inventors: Alan J. Fischman, Boston, Mass.; Howard F. Solomon, New Hope, Pa.; Claudia K. Derian, Hatboro, Pa.; Gary J. Bridger, Bryn Mawr, Pa.; John D. Higgins, III; Scott K. Larsen, both of West Chester, Pa.; Pedro E. Hernandez, Malvern, Pa.; Robert H. Rubin, Brookline, Mass.; H. William Strauss, Skillman, N.J.; Anthony J. Fuccello, Princeton, N.J.; Daniel J. Kroon, Flemington, N.J.

[73] Assignees: The General Hospital Corporation, Boston, Mass.; Johnson Matthey, Inc., West Chester, Pa.; Ortho Pharmaceutical Corporation, Raritan, N.J.

[21] Appl. No.: 140,000

[22] Filed: Oct. 22, 1993

Related U.S. Application Data

[63] Continuation-in-part of Ser. No. 55,312, May 3, 1993, Pat. No. 5,350,837, and a continuation-in-part of Ser. No. 56,950, May 5, 1993, abandoned, which is a continuation of Ser. No. 349,186, May 4, 1989, abandoned.

[51] Int. Cl.$^6$ .................. A61K 51/08; A61K 37/00
[52] U.S. Cl. .............. 424/1.69; 424/9.34; 424/9.341; 530/330; 530/331; 514/6; 514/17; 514/18
[58] Field of Search .................. 424/1.41, 1.69, 424/9, 9.34, 9.341, 9.36, 9.364; 530/330, 331; 514/6, 17, 18

[56] References Cited

U.S. PATENT DOCUMENTS

| | | | |
|---|---|---|---|
| 4,315,906 | 2/1982 | Gelder et al. | 424/1 |
| 4,348,375 | 9/1982 | Goedemans et al. | 424/1 |
| 4,360,509 | 11/1982 | Goedemans et al. | 424/1 |
| 4,427,660 | 1/1984 | Schiffman et al. | 424/177 |
| 4,444,744 | 4/1984 | Goldenberg et al. | 424/1.1 |
| 4,472,509 | 9/1984 | Gansow et al. | 436/548 |
| 4,636,380 | 1/1987 | Wong et al. | 424/1.1 |
| 4,639,365 | 1/1987 | Sherry et al. | 424/9 |
| 4,707,353 | 11/1987 | Bugaj et al. | 424/1.1 |
| 4,741,900 | 5/1988 | Alvarez et al. | 424/85 |
| 4,915,933 | 4/1990 | Matwiyoff et al. | 424/9 |
| 4,926,869 | 5/1990 | Rubin et al. | 128/654 |
| 4,986,979 | 1/1991 | Morgan, Jr. et al. | 424/1.1 |
| 5,094,950 | 3/1992 | Kondo et al. | 530/391.5 |
| 5,225,180 | 7/1993 | Dean et al. | 424/1.1 |
| 5,376,356 | 12/1994 | Morgan, Jr. | 424/1.41 |

FOREIGN PATENT DOCUMENTS

| | | |
|---|---|---|
| 0 038 546 | 10/1981 | European Pat. Off. |
| 0 165 716 | 12/1985 | European Pat. Off. |
| 0 233 619 | 8/1987 | European Pat. Off. |
| 0 256 989 | 2/1988 | European Pat. Off. |
| 0 384 769 | 8/1990 | European Pat. Off. |
| 2109407 | 6/1983 | United Kingdom |
| WO 87/04351 | 7/1987 | WIPO |
| WO 88/05537 | 7/1988 | WIPO |
| WO 92/13572 | 8/1992 | WIPO |
| WO 93/10747 | 6/1993 | WIPO |
| WO 93/17719 | 9/1993 | WIPO |
| WO 93/21962 | 11/1993 | WIPO |
| WO 93/23085 | 11/1993 | WIPO |
| WO 93/25244 | 12/1993 | WIPO |

OTHER PUBLICATIONS

Goodwin, D. A., et al., "Indium–111 Labeled Cells: New Approaches and Radiation Dosimetry", pp. 343–351 in *Radiolabelled Cellular Blood Elements* by Thakur et al., Plenum Press, NY, 1985.

Hattori, Hiroshi, et al., "Synaptosomal Phospholipase D: Potential Role in Providing Choline for Acetylcholine Synthesis", *Biochemical and Biophysical Research Communications* 124(3):945–949 (Nov. 1984).

McAfee, J. G., et al., "Trends in Leukocyte Labeling", pp. 274–283 in *Radio labelled Cellular Blood Elements* by Thakur et al., Plenum Press, NY, 1985.

"Protecting Groups in Organic Synthesis"; John Wiley & Sons, New York, 193–217 (1981).

Weiner, Ronald, et al., "Lactoferrin: Its Role as a Ga–67–Binding Protein in Polymorphonuclear Leukocytes", *The Journal of Nuclear Medicine* 22(1):32–37 (1981).

English Abstract of FI 823633 from World Patents Index. Dialog file 351 (Accession number 83–27457K/12), 1983.
English Abstract of FI 870122 from World Patents Index. Dialog file 351 (Accession number 88–220366/31), 1988.

Abrams, M.J. et al., "Technetium–99m–Human Polyclonal IgG Radiolabeled via the Hydrazino Nicotinamide Derivative for Imaging Focal Sites of Infection in Rats" *J. Nucl. Med.* 31(12):2022–2028 (Dec. 1990).

Anderson, R.P. et al., "Hepatobiliary Excretion of Bacterial Formyl–methionyl Peptides in Rat", *Dig. Dis. Sci.* 37(2): 248–256 (Feb. 1992).

(List continued on next page.)

*Primary Examiner*—John Kight
*Assistant Examiner*—Lara C. Kelley
*Attorney, Agent, or Firm*—Sterne, Kessler, Goldstein & Fox P.L.L.C.

[57] ABSTRACT

The invention relates to a method of detecting a site of infection or inflammation, and a method for treating such infection or inflammation, in an individual by administering to the individual a diagnostically or therapeutically effective amount of detectably labeled, therapeutic, or therapeutically-conjugated, chemotactic peptide that accumulates substantially at the infected or inflamed site, said chemotactic peptide having the general structure

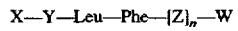

X—Y—Leu—Phe—[Z]$_n$—W wherein:

X is an amino protecting group,
Y is an amino acid residue,
Z is a spacer sequence,
n is 0 or 1, and
W is a labeling or attachment substituent.

73 Claims, 16 Drawing Sheets

OTHER PUBLICATIONS

Babich et al., "Technetium–99m–Labeled Hydrazino Nicotinamide Derivatized Chemotactic Peptide Analogs for Imaging Focal Sites of Bacterial Infection". *J. Nucl. Med.* 34(11): 1964–1974 (Nov. 1993).

Babich et al., "Technetium–99m–Labeled Chemotactic Peptides: Comparison with Indium–111–Labeled White Blood Cells for Localizing Acute Bacterial Infection in the Rabbit", *J. Nucl. Med.* 34(12):2176–2181 (Dec. 1993).

Babich, J. W., et al., "Imaging Focal Sites of Infection with Technetium–99M–labeled Hydrazino Nicotinamide Conjugated Chemotactic Peptides", *J. Nucl. Med.* 33:910, Absract 363. (1992).

Babior, B. M. et al., "The Production By Leukocytes Of Superoxide, A Potential Bactericidal Agent", *J. Clin. Invest.* 52:741–744 (1973).

Baggiolini, M., et al., "Neutrophil–activating Peptide–1/ Interleukin 8, a Novel Cytokine That Activates Neutrophils", *J. Clin. Invest.* 84:1045–1049 (Oct. 1989).

Becker, E. L., "Some Interrelations of Neutrophil Chemotaxis, Lysosomal Enzyme Secretion, and Phagocytosis as Revealed by Synthetic Peptides", *Am. J. Pathol.* 85(2) : 385–394 (Nov. 1976).

Butcher, E. C., "Leukocyte–Endothelial Cell Recognition: Three (or More) Steps to Specificity and Diversity", *Cell* 67:1033–1036 (Dec. 20, 1991).

Chauhan et al., "Conformational Analysis of an Active Chemotactic Peptide Analog Containing Z–Dehydrophenylalanine at Position 3", *Tetrahedron* 44(8) : 2359–2366 (1988).

Crystal et al., "Pulmonary Sarcoidosis: A Disease Characterized and Perpetuated by Activated Lung T–Lymphocytes", *Annals of Internal Medicine* 94(1) : 73–94 (1981).

Dentino et al., "Role of Peptide Backbone Conformation on Biological Activity of Chemotactic Peptides", *J. Biol. Chem.* 266(28) : 18460–18468 (1991).

Deuel, T. F., et al., "Platelet factor 4 is chemotactic for neutrophils and monocytes", *Proc. Natl. Acad. Sci. USA* 78(1) : 4584–4587 (1981).

Dolmatch and Niedel, "Formyl Peptide Chemotactic Receptor", *J. Biol. Chem.* 258(12) : 7570–7577 (Jun. 25, 1983).

Dorland, W. A., Dorland's Illustrated Medical Dictionary, ed. 26, *W. B. Saunders Company;* see: agonist and antagonist, pp. 85 (1981).

Duncan, D. B., "Multile Range and Multiple F Tests", *Biometrics* 11 : 1–42 (Mar. 1995).

Fischman et al., "Localization of Fc and Fab Fragments of Nonspecific Polyclonal IgG at Focal Sites of Inflammation", *J. Nucl. Med.* 31(7) : 1199–1205 (Jul. 1990).

Fischman et al., "Imaging of Focal Sites of Inflammation in Non–Human Primates with a Tc99m–Labeled Chemotactic Peptide", *J. Nucl. Med.* 34 : 104P, Abstract No. 415 (Jun. 11, 1993).

Fischman, A. J. et al., "Imaging Focal Sites of Bacterial Infection in Rats with Indium–111–Labeled Chemotactic Peptide Analogs", *J. Nucl. Med.* 32(3) : 483–491 (Mar. 1991).

Fletcher, M. P. et al., "Correlation of Human Neutrophil Secretion, Chemoattractant Receptor Mobilization, and Enhanced Functional Capacity", *J. Immunol.* 128(2) : 941–948 (Feb. 1982).

Freer, R. J., "Antagonists of the Formylated Peptide Chemoattractants: Structure–Activity Comparisons With Formyl–Methionyl–Leucyl–Phenylalanine–OH", *Biochemistry of Acute Allergic Reactions*, ed. Alan R. Liss, N.Y., pp. 161–168 (1981).

Freer, R. J., et al., "Formyl Peptide Chemoattractants: A Model of the Receptor on Rabbit Neutrophils", *Biochem.* 21:257–263 (1982).

Gavuzzo, E. et al., "Synthesis and Properties of Chemotactic Peptide Analogs", *Int. J. Peptides Protein Res.* 37:268–276 (1991).

Greene, T. W.: Protecting Groups in Organic Synthesis, Chapter 6: Protection for the Thiol Group, *John Wiley & Sons, N. Y.:* 193–217 (1981).

Harrison, W.T. , "Principles of Internal Medicine", 10th ed., *McGraw–Hill Publishers, N.Y.:* 346 (1983).

Hnatowich, D.J. et al., "Radioactive Labeling of Antibody: A Simple and Efficient Method", *Science* 220 : 613–615 (May 6, 1983).

Hnatowich, D.J. et al., "The Preparation and Labeling of DTPA–Coupled Albumin", *Int. J. Appl. Radiat. Isot.* 33: 327–332 (1982).

Igbal, M., et al., "Conformationally constrained chemotactic peptide analogs of high biological activity", *FEBS* 165(2) : 171–174 (Jan. 1984).

Jiang et al., "Localization of Abscess with an Iodinated Synthetic Chemotactic Peptide", *J. Nucl. Med.* 21(3) : 110–113 (1982).

Johnson, J.A., et al., "Detection of Occult Infection Following Total Joint Arthroplasty Using Sequential Technetium–99m HDP Bone Scintigraphy and Indium–111 WBC Imaging", *J. Nucl. Med.* 29:1347–1353 (1988).

Juweid, M., et al., "Accumulation of immunoglobulin G at focal sites of inflammation", *Eur. J. Nucl. Med.* 19:159–165 (1992).

Kate ten, C. I. et al., "Effect of isoelectric point on biodistribution and inflammation: imaging with indium–111–labelled IgG", *Eur. J. Nucl. Med.* 17:305–309 (1990).

Khaw, B.A., et al., "Myocardial Infarct Imaging of Antibodies to Canine Cardiac Myosin with Indium–11–Diethylenetriamine Pentaacetic Acid", *Science* 209 : 295–297 (1980).

Kraus, J. L. and Attardo, G., "Synthesis and Biological Activities of New N–Formylated Methionyl Peptides Containing an α–substituted Glycine Residue", *Eur. J. Med. Chem.* 27:19–26 (1992).

Kraus, J. L. et al. , "Cyclic Tetrameric Clusters of Chemotactic Peptides as Superactive Activators of Lysozyme Release from Human Neutrophils", *Biochem. Biophys. Res. Comm.* 124(3):9399–944 (Nov. 1984).

Larson, S. M. "Radiolabeled Monoclonal Anti–Tumor Antibodies in Diagnosis and Therapy", *J. Nucl. Med.* 26:538–545 (1985).

Lasky, L. A. ,"Selectins: Interpreters of Cell–Specific Carbohydrate Informaton During Inflammmation", *Science* 258 : 964–970 (Nov. 6, 1992).

Magnuson, J. E. , et al. , "In–111 labeled Leukocyte Scintigraphy in Suspected Orthopedic Prosthesis Infection: Comparison with Other Imaging Modalities", *Radiology* 168(1) : 235–239 (1988).

Mansfield, P., et al, "NMR Imaging in Biomedicine", *Academic Press, N.Y.:*234 see lines 12–20 (1982).

McAfee, J. G., et al., "Distribution of Leukocytes Labeled with In-111 Oxine in Dogs With Acute Inflammatory Lesions", *J. Nucl. Med.* 21(11):1059–1068 (1980).

McAfee, J. G. et al., "Technique of Leukocyte Harvesting and Labeling: Problems and Perspectives", *Semin. Nucl. Med.* 14(2):83–106 (Apr. 1984).

Merrifield, R. B., "Solid Phase Peptide Synthesis. I. The Synthesis of Tetrapeptide", *J. Am. Chem. Soc.* 15:2149–2154 (1963).

Morrison, R. T. and Boyd, R.N., "The $S_N2$ Reaction": Reactivity: page 465, Reduction of Acids to Alcohols: page603, in: *Organic Chemistry*, 3rd ed., Allyn and Bacon, Inc. (1973).

Niedel, J. et al., "Covalent Affinity Labeling of the Formyl Peptide Chemotactic Receptor", *J. Biol. Chem.* 255(15):7063–7066 (Aug. 10, 1980).

Niedel, J., et al., "Receptor–Mediated Uptake and Degradation of $^{125}$I–Chemotactic Peptide by Human Neutrophiles", *J. Biol Chem.* 254(21):10700–10706, (1979).

Niedel, J., et al., "Receptor —Mediated Internalization of Fluorescent Chemotactic Peptide by Human Neutrophils", *Science* 205:1412–1414 (Sep. 28, 1979).

O'Flaherty, J.T. et al., "Neutropenia Induced by Systemic Infusion of Chemotactic Factors", *J. Immunol.* 118(5):1586–1589 (May, 1977).

O'Flaherty, J.T., et al., "Inhibition of In Vivo and In Vitro Neutrophil Responses to Chemotactic Factors by a Competitive Antagonist", *J. Immunol.* 120(4):1326–1332 (Apr., 1978).

Parker, S.P., Dictionary of Scientific and Technical Terms, 4th ed., McGraw–Hill Book Company, New York, St. Louis, San Francisco, p. 1850 (1989).

Pike, M.C. and Snyderman, R., "Leukocyte Chemoattractant Receptors", *Methods Enzymol.* 162:236–245 (1988).

Pike, M.C. et al., "Chemoattractant—Mediated Stimulation of the Respiratory Burst in Human Polymorphonuclear Leukocytes May Require Appearance of Protein Kinase Activity in the Cells' Particulate Fraction", *Blood* 67(4):909–913 (Apr., 1986).

Ranney and Huffaker, "Magnetic Micropheres for the Targeted Controlled Release of Drugs and Diagnostic Agents", *Ann. N.Y. Acad. Sci.* 507:104–119 (1987).

Rom, W. N., "Commentary: Research on the Mechanisms of the Occupational Lung Diseases", *Archives of Environmental Health* 39(3):186–189 (May/Jun. 1984).

Rot, A., et al., "A series of six ligands for the human formyl peptide receptor: Tetrapeptides with high chemotactic potency and efficiency", *Proc. Natl. Acad. Sci. USA* 84:7967–7971 (1987).

Schiffmann, E., et al., "N–Formylmethionyl Peptides as Chemoattractants for Leucocytes", *Proc. Natl. Acad. Sci. USA* 72:1059–1062 (1985).

Schmitt, M., et al., "Photoaffinity Labeling of the N–Formyl Peptide Receptor Binding Site of Intact Human Polymorphonuclear Leukocytes", *J. Biol. Chem.* 236(1):649–654, (10th Jan. 1983).

Schwartz, D.A., et al., "Preparation of Hydrazino–Modified Proteins and Their Use for the Synthesis of $^{99m}$Tc–Protein Conjugates", *Bioconjugate Chem.* 2(5):333–336 (1991).

Showell, H.J., et al., "The Structure–Activity Relations of Synthetic Peptides as Chemotactic Factors and Inducers of Lysosomal Enzyme Secretion for Neurophils", *J. Exper. Med.* 143:1154–1169 (1976).

Snyderman, R. and Verghese, M.W., "Leukocyte Activation by Chemoattractant Receptors: Roles of a Guanine Nucleotide Regulatory Protein and Polyphosphoinositide Metabolism", *Rev. Infect. Dis.* 9 (*Suppl.*):S562–S569 (Sep.–Oct. 1987).

Spisani, S., et al., "Response of Human Neutrophils to Formyl—Peptide Modified at the Terminal Amino and Carboxyl Groups", *Inflammation* 10(4):363–369 (1986).

Stedman, T.L., Stedman's Medical Dictionary, 25th Edition, Williams & Wilkins, Baltimore, Hong Kong, London, Sydney, p. 37 and p. 91 (1990).

Strauss et al., "Non–tumor Applications of Radioimmune Imaging", *Nucl. Med. Biol.* vol. 18 (1):127–134 (1991).

Syrjälä, M.T., et al., "Diagnostic Significance of Indium–111 Granulocyte Scintigraphy in Febrile Patients", *J. Nucl. Med.* 28(2):155–160 (1987).

Syrjälä, M.T., et al., "Sensitivity of $^{111}$In–Granulocyte Scintigraphy in Various Local Infections", *Acta Radiologica* 28(5):549–553 (1987).

Tharkur, M. L. et al., "Neutrophile Labeling: Problems and Pitfalls", *Semin. Nucl. Med.* 14:107–117 (1984).

Toniolo, C., et al., "Structural Requirements for Formyl Homooligopeptide Chemoattrctants", *Biochem.* 23:698–704 (1984).

Torrini et al., "Synthesis and Properties of Chemotactic Peptide Analogs", *Int. J. Peptide Protein Res.* 38:495–504 (1991).

Verma, R. C. et al., "Receptor Mediated Selective Radiolabeling of Neurophils", Abstract, *J. Nucl. Med.* 24(5):P7 (1983).

Williams, L.T., et al., "Specific receptor sites for chemotactic peptides on human polymorphonuclear leukocytes", *Proc. Natl. Acad. Sci. USA* 74:1204–1208 (1977).

Wukich, D. K., et al., "Diagnosis Infection by Preoperative Scintigraphy with Indium–Labeled White Blood Cells", *The Journal of Bone and Joint Surgery, Inc.* 69–A(9)24:1353–1360 (1987).

Zalcberg, J. R., "Tumor localization using radiolabeled monoclonal antibodies", *Am. J. Clin. Onco.* (CCT) 8:481–489 (October 1985).

Zoghbi et al., "Selective Cell Labeling: A Potential Radioactive Agent for Labeling Human Neotrophiles", *J. Nucl. Med.* 22:32 (1981).

Opitz and Fruchtmann, "Acylierte Tripeptide als Chemotaxinationantagonisten", *Hoppe–Seyler's Physiol. Chem.* 362:1037–1041 (1981).

Translation of Opitz and Fruchtmann, ("Acylierte Tripeptide als Chemotaxinationantagonisten", *Hoppe–Seyer's Physiol. Chem.* 362:1037–1041 (1981), Acylated Tripeptides as Chemotactic Factor Antagonists.

| | EC$_{50}$ |
|---|---|
| ForMLF | 100 |
| Hexapeptide | 100 |
| HP2 | 12 |
| HP3 | 40 |
| HP4 | 60 |
| HP1 | 500 |
| ForNLF | 320 |

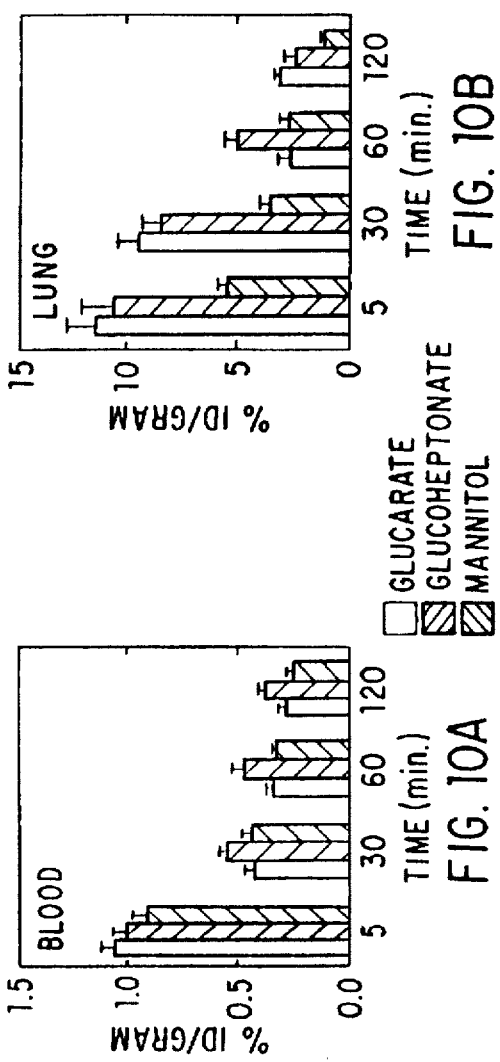
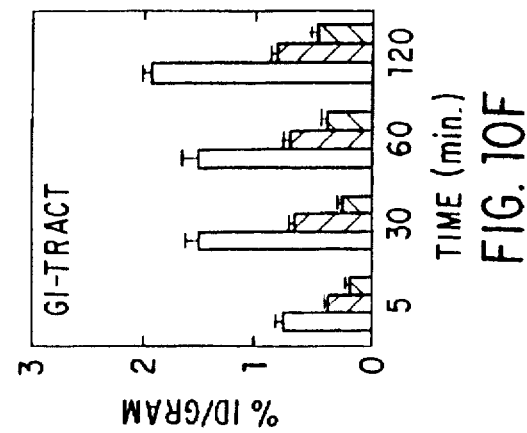
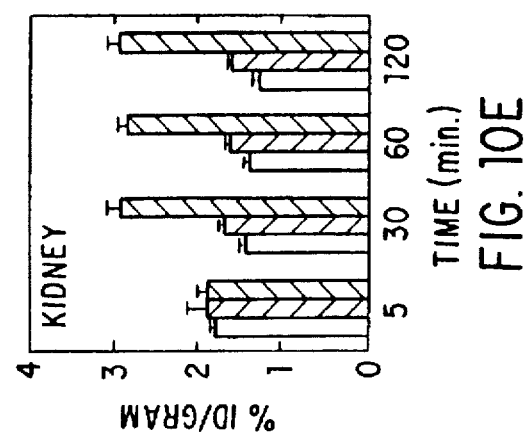
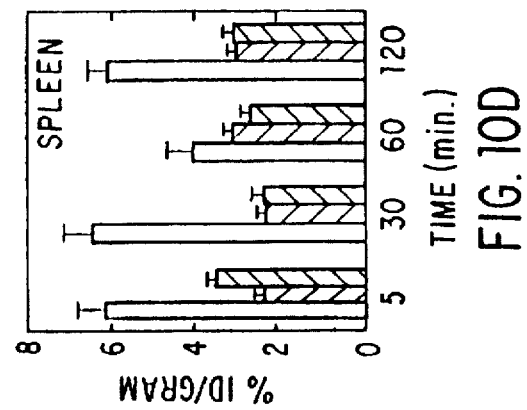
FIG. 10A  FIG. 10B  FIG. 10C
FIG. 10D  FIG. 10E  FIG. 10F

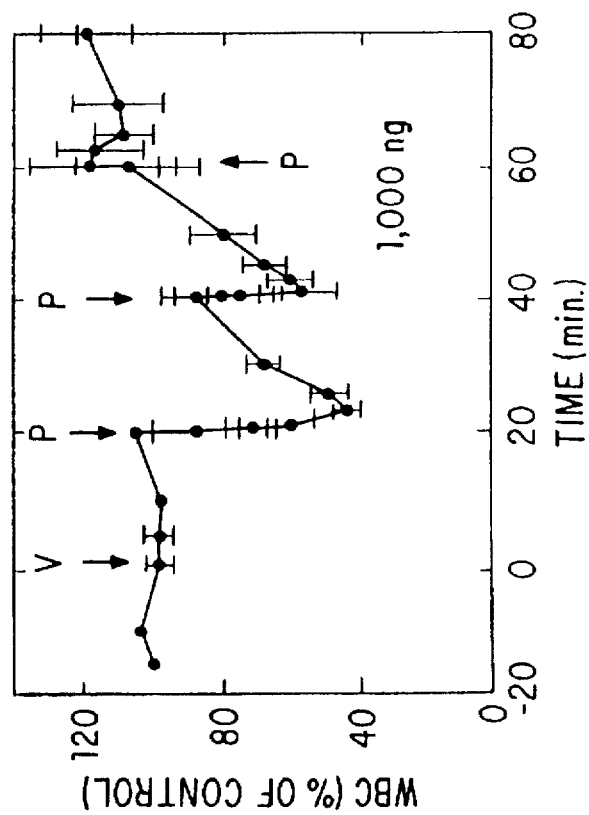
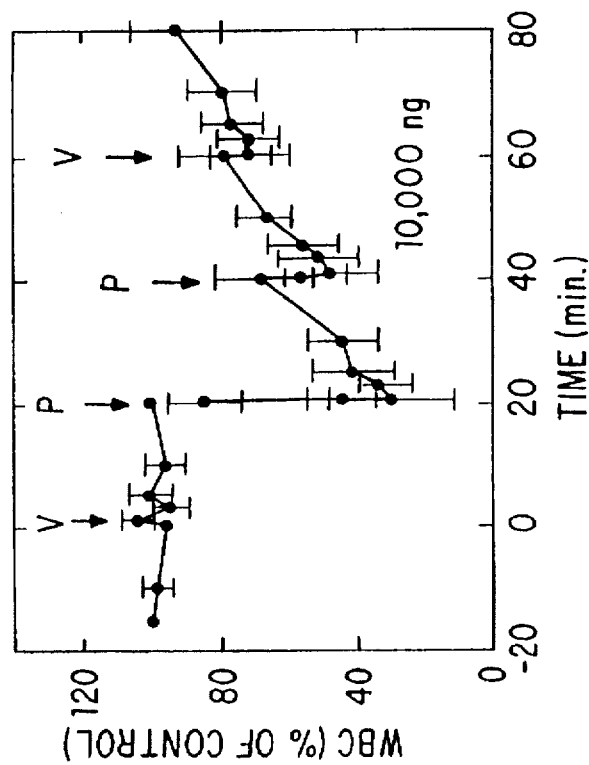
FIG. 12B
FIG. 12A $^{99m}$Tc-Peptide
$^{111}$In-WBC's
Early
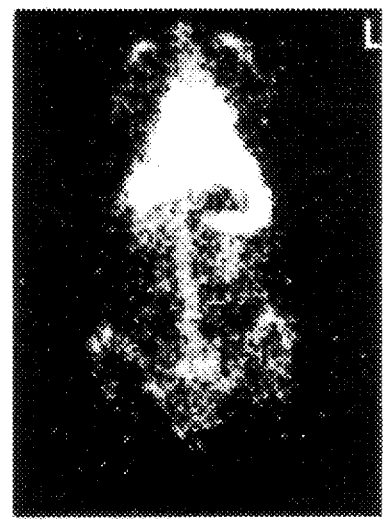
Late
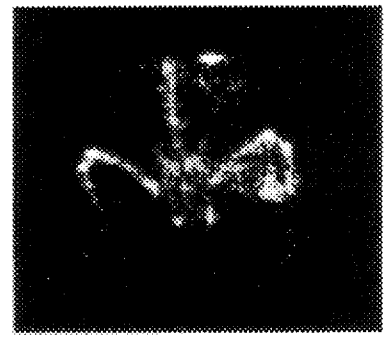
FIG. 14A
FIG. 14B

LABELED CHEMOTACTIC PEPTIDES TO IMAGE FOCAL SITES OF INFECTION OR INFLAMMATION

CROSS-REFERENCES TO RELATED APPLICATIONS

This application is:

A. a continuation-in-part of U.S. application Ser. No. 08/056,950, filed May 5, 1993, abandoned, which is a continuation of U.S. application Ser. No. 07/349,186, filed May 4, 1989, now abandoned; and B. a continuation-in-part of U.S. application Ser. No.08/055,312, filed May 3, 1993, now U.S. Pat. No. 5,350,837.

BACKGROUND OF THE INVENTION

1. Field of the Invention

This invention is directed to chemotactic peptides and their use in detecting sites of infection and inflammation in an individual and treating tissue damage.

2. Description of Related Art

Inflammation occurs in response to various forms of tissue damage. This tissue damage can result from microbial invasion, auto-immune processes, tissue or organ allograft rejection, or such injurious external influences as heat, cold, radiant energy, electrical or chemical stimuli, or mechanical trauma. Whatever the cause or body site, the ensuing inflammatory response is quite similar, consisting of a complicated set of functional and cellular adjustments, involving changes in microcirculation, movement of fluids, and influx and activation of inflammatory cells (leukocytes). This response pattern constitutes an important part of innate host defense mechanisms against infection, and although it carries the "cost" of additional tissue damage resulting from the inflammatory process itself, it ultimately promotes the subsequent repair process.

Upon microbial infection, or following certain forms of tissue damage, soluble chemical substances are elaborated that initiate the inflammatory response cascade, consisting of a complex series of events. Blood flow in the inflammatory site is increased, and in response to increased capillary permeability, there is an efflux of fluid from the blood. This localized exudation of fluid at the site of injury includes plasma proteins that normally leave the capillaries at a relatively low rate. Leukocytes also enter the inflammation site via the capillaries, both by passive and active processes. The inflammatory cellular exudate initially consists primarily of polymorphonuclear (PMN) leukocytes (also termed neutrophils or granulocytes). Subsequently, monocytes, lymphocytes, and plasma cells can be found in the inflammatory infiltrate.

The identification and characterization of the sites of infection and inflammation are important for clinical diagnosis in human and veterinary medicine. In the case of early localized infections, it is frequently necessary to search for "hidden sites of inflammation" in individuals who present clinical syndromes no more specific than fever and weight loss. Similarly, in patients with autoimmune diseases, such as rheumatoid arthritis, or in recipients rejecting tissue or organ allografts, the capacity to identify inflammatory sites, define their extent, and monitor changes following initiation of therapy is important for effective clinical care.

Not surprisingly, then, much effort has been expended and many techniques developed in an attempt to identify the site(s) and assess the extent of the inflammatory process. These techniques include conventional x-ray techniques, CAT scanning, and a variety of radionuclide scans. (Sutton, A Textbook of Radiology and Imaging, 3rd Ed., Churchill Livingston (1980); Maysey et al., Clinical Nuclear Medicine Ed., W. B. Sanders (1983). Examples of techniques for radionuclide scans that have been utilized include:

1. $^{67}$Gallium, which binds to the plasma protein, transferrin, after injection and tends to localize at sites of chronic inflammation;
2. $^{111}$Indium-labeled granulocytes, which, when reinjected into the host, will accumulate at the site of inflammation;
3. Radiolabeled chelates, which pass into the extracellular fluid and can then accumulate at sites of fluid accumulation; and
4. Thallium scans or so-called first pass radionuclide angiograms to assess areas of increased blood flow.

Conventional nuclear medicine techniques make use of the following radiopharmaceuticals for infection inflammation imaging: $^{67}$Ga citrate, $^{111}$In labeled leukocytes, $^{99m}$Tc labeled leukocytes, and $^{111}$In labeled human polyclonal IgG. Although each of these agents can yield useful results in specific situations, considerable room for improvement remains.

$^{67}$Ga citrate can be mechanistically categorized along with $^{111}$In-IgG (MW: 150 kD) as a labeled protein, since, after intravenous injection, $^{67}$Ga citrate readily transchelates to circulating transferrin (MW: 100 kD) and lactoferrin (MW: ~100 kD) in plasma. Inflammation imaging with labeled proteins is the result of differences in rates of accumulation within the site of inflammation and clearance from normal tissues (Juweid, M., et al., Eur. J. Nucl. Med. 19:159–165 (1992)). With these reagents, optimal lesion detection typically occurs at ≧24 hours after injection because of preferential wash-out from normal tissues and blood clearance.

Thakur et al., have extensively analyzed and discussed methods based on neutrophil labeling in vitro (Sem. Mucl. Med. 14:107–117 (1984)). In this approach, an individual's neutrophils are labeled with a gamma emitting radionuclide, $^{111}$In being the nuclide of choice. Such labeled neutrophils could be used for in vivo kinetic studies and for imaging of inflammatory foci. One disadvantage of this technique is the need to remove and isolate neutrophils prior to their labeling in vitro.

Leukocytes produce a variety of mediators that control the extent and duration of the inflammatory response, and bear on their surface a variety of receptors that can bind and respond to the chemical mediators and other proteins present in the inflammatory fluid. Such receptor-mediator interactions are important in controlling leukocyte function within the inflammatory site. Among the inflammatory mediators are the chemotactic factors, also called chemoattractants, which have the capacity to induce the directed migration and activation of PMN's and macrophages (see for general review and discussion: Roitt et al., Immunology, Gower Medical Pub., London (1985)).

$^{111}$In labeled leukocytes have been a highly successful imaging agent, but significant preparation time and blood handling are required. Study times are further prolonged because radiolabeled cells require several hours to localize after injection since they must detect the chemoattractant signal, then migrate to the site of inflammation. Also, dosimetric considerations limit the amount of radioactivity that can be administered, frequently resulting in poor quality images. Although much higher doses of $^{99m}$Tc labeled leukocytes can be used, general applicability is limited by accumulation of radioactivity in nontarget organs.

The time between injection and lesion detection could be significantly reduced by the development of low molecular weight radiopharmaceuticals that bind to circulating inflammatory cells as well as to cells already present at the site of inflammation. Candidate molecules with these characteristics include: IL-8 (Baggiolini, M., et al., *J. Clin. Invest.* 84(4):1045–1049 (1989)), platelet factor-4 (Deuel, T. F., et al., *Proc. Natl. Acad. Sci. USA* 78(1):4584–4587 (1981)) and the peptide, N-formyl-methionyl-leucyl-phenylalanine (For-MLF) (MW 437) (Showell, H. J., et al., *J. Exper. Med.* 143:1154–1169 (1976); Schiffmann, E., et al., *Proc. Natl. Acad. Sci. USA* 72:1059–1062 (1975); Williams, L. T., et al., *Proc. Nat. Acad. Sci. USA* 74:1204–1208 (1977)).

For-MLF is a bacterial product that initiates leukocyte chemotaxis by binding to high affinity receptors on the white blood cell membranes (Williams, L. T., et al., *Proc. Nat. Acad. Sci. USA* 74:1204–1208 (1977); Showell, H. J., et al., *J. Exper. Med.* 143:1154–1169 (1976); Schiffmann, E., et al., *Proc. Natl. Acad. Sci. USA* 72:1059–1062 (1975)). These receptors are present on both PMN's and mononuclear phagocytes. Although numerous in vitro structure-activity studies have demonstrated that many synthetic analogs of these small, N-formyl-methionyl peptides bind to neutrophils and macrophages with equal or greater affinity compared to the native peptide (Niedel, J., et al., *J. Biol. Chem.* 255:7063–7066 (1980); O'Flaherty, J. T., et al., *J. Immunol.* 120:1326–1332 (1978); Rot, A., et al., *Proc. Natl. Acad. Sci. USA* 84:7967–7971 (1987); Iqbal, M., et al., *FEBS* 165:171–174 (1984)), in vivo biodistribution and biological activity studies have been relatively limited. As granulocytes respond to the chemoattractant gradient, the affinity of the receptors decreases as additional receptors are expressed, until the cell reaches the site of inflammation, where the concentration of chemoattractant is greatest (Snyderman, R., et al., *Rev. Infect. Dis.* 9:S562–S569 (1987); Fletcher, M. P., *J. Immunol.* 128:941–948 (1988); Niedel, J., et al., *J. Biol. Chem.* 10:700–710 (1979)). Due to the very small size of For-MLF (MW 437), its molecular structure can be readily manipulated to design an optimal imaging agent.

Many species of bacteria can produce one or more types of chemotactic molecules, either small peptides, larger proteins, or lipids (Klein, J., *Immunology: The Science of Self-Nonsef Discrimination*, Wiley Interscience, New York (1982)). For example, *E. coli* bacteria are known to produce potent chemotactic molecules having as their active components small, heterogenous peptides with blocked amino groups. Such peptides have been synthesized and shown to be potent chemoattractants for PMN's. The best known of these chemotactic peptides are For-MLF and some related tetrapeptides (Schiffman et al., *Proc. Natl. Acad. Sci. USA* 72:1059–1062 (1975); Schiffmann et al., U.S. Pat. No. 4,427,660 (1984)). Structure-function studies of these peptides suggested the presence of stereo-specific receptors on the surface of target cells (Becker, E. L., *Am. J. Pathol.* 85:385–394 (1976)); such receptors were subsequently detected using radiolabeled formyl peptides as ligands (Williams et al., *Proc. Natl. Acad. Sci. USA* 74:1204–1208 (1977)).

Subsequently, a chemotactic peptide was synthesized with the structure N-Formyl-Nle-Leu-Phe-Nle-Tyr-Lys, which could be labeled to a higher specific radioactivity with $^{125}$I at the Tyr residue, and was shown to bind strongly to receptors on human neutrophils (Niedel et al., *J. Biol. Chem.* 254:10700–10706 (1979)).

Bacterial cells can also induce host cells to produce chemotactic factors, e.g., by activating components of the host's complement system, giving rise to the local production of the chemotactic molecules, C5a and C5b67. Once an immune response ensues in the host, IgG antibody molecules can also act as chemotactic factors, as can molecules produced by activated T lymphocytes. Different chemotactic molecules have selectivity for various PMN's (e.g., neutrophils, basophils, eosinophils), mast cells, monocytes/ macrophages, or lymphocytes, based on the presence of the appropriate receptors on the inflammatory cell type.

Chemotactic peptides have been the focus of numerous structure-activity studies directed at determining the specific features of the molecule that are responsible for receptor binding and activation (Deuel, T. F., et al., *Proc. Natl. Acad. Sci. USA* 78(1):4584–4587 (1981); O'Flaherty, J. T., et al., *J. Immunol.* 120:1326–1332 (1978); Rot, A., et al., *Pro. Natl. Acad. Sci. USA* 84:7967–7971 (1987); Iqbal, M., et al., *FEBS* 165:171–174 (1984)). Most of these studies have concentrated on substitutions of natural amino acids in the For-MLF sequence; however, there have been reports of extended peptides and highly negatively charged peptides (Fischman, A. J., *J. Nucl. Med.* 32:483–491 (1991); Toniolo, C., et al., *Biochem.* 23:698–704 (1984)) that have $EC_{50}$'s, for receptor binding and activation that are less than or equal to those of the native peptide. In general, the results of these structure-activity studies have established that, although modification at the N-terminus has a profound negative effect on receptor binding and activation, C-terminal modifications have minimal effects (Spisani, S., et al., *Inflammation* 10:363–369 (1986)). In addition, receptor binding and biological activity are highly correlated (Deuel, T. F., et al., *Proc. Natl. Acad. Sci. USA* 78(1):4584–4587 (1981); Schiffmann, E., et al., *Proc. Natl. Acad. Sci. USA* 72:1059–1062 (1975)). Based on these data, a model for the conformation of the receptor-peptide complex has been proposed in which only the N-terminal four amino acid residues interact with the receptor (Freer, R. J., et al., *Biochem.* 21:257–263 (1982)).

It has been demonstrated that synthetic analogs of For-MLF, modified at the C-terminus, bind to neutrophils and macrophages with equal or greater affinity compared to the native peptide (Deuel, T.F., et al., *Proc. Natl. Acad. Sci. USA* 78(1):4584–4587 (1981); Schiffmann, E., et al., *Proc. Natl. Acad. Sci. USA* 72:1059–1062 (1975); Niedel, J., et al., *J. Biol. Chem.* 255:7063–7066 (1980)). Thus inclusion of a labeling moiety at the C-terminus permits the preparation of radiolabeled analogs with preserved receptor binding.

This approach to infection imaging has several theoretical advantages over currently used radiopharmaceuticals. The interval between injection and lesion detection could be substantially reduced by the ability of these small molecules to bind to circulating granulocytes, as well as to leukocytes already present at the site of inflammation. The low molecular weight of the peptide (<1,000 daltons) allows more rapid diffusion into areas of infection and inflammation compared to labeled proteins and leukocytes. In addition, radiolabeling of granulocytes in situ eliminates the alteration of cellular function that is associated with conventional labeling procedure and eliminates blood handling with its inherent dangers to personnel and patients.

Zoghbi et al., *J. Nuc. Med.* 22:32 (1981) labeled For-MLF with $^{111}$In using the protein transferrin coupled to the peptide and suggested that this reagent had promise for selectively labeling human neutrophils. While this approach provides a potential solution for the problem of specificity of labeling, it does not suggest a solution for the complication of removing cells from an individual, manipulating them in vitro, and then reinfusing them.

One report describes an attempt to localize sterile abscesses in vivo by direct injection of $^{125}$I-labeled N-Formyl-Nle-Leu-Phe-Nle-Tyr-Lys into rabbits (Jiang et al., *Nucl. Med.* 21:110–113 (1982)). While achieving effective labeling ratios (abscess-to-muscle), use of this agent caused transient neutropenia followed by rebound neutrophilia. The authors recognized that further development was needed to avoid the side effects of neutropenia/neutrophilia and make this method clinically useful. Further, $^{125}$I does not image well and this reference does not disclose or suggest better imaging isotopes, such as, $^{123}$I, $^{111}$In, or $^{99m}$Tc.

Morgan et al. in U.S. Pat. No. 4,986,979 disclosed a method of enhancing the amount of label accumulating at tissue sites of inflammation. Advantage was taken of the up-regulation of surface antigenic markers on leukocytes upon activation thereof. A method of imaging utilizing a chemotactic peptide containing an affinity label and a radionuclide label conjugated to leukocytes was described, as well as imaging applications relating to the enhancement. These authors failed to disclose any synthetic methods for the synthesis of antagonists or that such antagonists could be useful for avoiding the neutropenic response.

Whereas the above techniques may provide useful information, they may also result in an unacceptably high frequency of both false positive and false negative results, require an unacceptable amount of handling and processing, or be accompanied by unacceptable side effects. Thus, there is a recognized continuing need in the art for more direct, more sensitive, and more specific methods for detecting and localizing sites of infection or inflammation, particularly techniques that could be performed serially to assess the response to therapy over time.

SUMMARY OF THE INVENTION

The present invention relates to a substantially non-invasive method for imaging infection or inflammation sites based upon the discovery that detectably labeled chemotactic peptides injected systemically into animals accumulate at sites of local infection.

More particularly, the present invention relates to a method of detecting a site of infection or inflammation in an individual which comprises:

a. administering to the individual a diagnostically effective amount of a detectably labeled chemotactic peptide

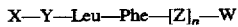

wherein:
X is an amino-protecting group,
Y is an amino acid residue,
Z is a spacer sequence,
n is 0 or 1, and
W is a labeling or attachment substituent of the structure

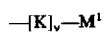

wherein:
K is an intermediary functional group,
v is 0 or 1, and
M$^1$ is a diagnostically detectable label; and
wherein the chemotactic peptide substantially accumulates at the site of infection or inflammation and does not substantially accumulate at a site that is not infected or inflamed; and b. detecting the chemotactic peptide.

In a preferred embodiment, the present invention relates to a method of detecting a site of infection or inflammation in an individual which comprises:

a. administering to the individual a diagnostically effective amount of a detectably labeled chemotactic peptide

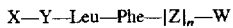

wherein:
X is an amino protecting group.
Y is

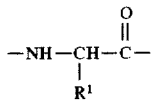

where
R$^1$ is benzyl, alkyl, or —CH$_2$—CH$_2$—R$^2$—CH$_3$ and

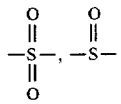

Z is a spacer sequence,
n is 0 or 1, and
W is a labeling or attachment substituent of the structure

wherein:
K is an intermediary functional group,
v is 0 or 1, and
M$^1$ is a diagnostically detectable label; and
wherein the chemotactic peptide substantially accumulates at the site of infection or inflammation and does not substantially accumulate at a site that is not infected or inflamed; and b. detecting the chemotactic peptide.

In another embodiment, the present invention relates to a detectably labeled chemotactic peptide

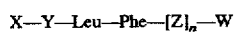

wherein:
X is an amino protecting group of the structure

where R$^3$ is selected from the group consisting of hydrogen, alkyl, alkenyl, alkynyl, alkoxy, aralkoxy, and amino and R$^4$ is oxygen or sulfur.
Y is an amino acid residue,
Z is a spacer sequence selected from the group consisting of aliphatic diamines of 1 to 6 carbon atoms, [R$^6$]$_m$, and mixtures thereof, wherein R$^6$ is an amino acid residue and m is an integer greater than or equal to 1,
n is 0 or 1, and
W is a labeling or attachment substituent of the structure

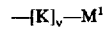

wherein:
K is DTPA, EDTA, or HYNIC,
v is 1, and $M^1$ is $^{111}$In or $^{99m}$Tc; and wherein the chemotactic peptide substantially accumulates at the site of infection or inflammation and does not substantially accumulate at a site that is not infected or inflamed.

Therapeutic compositions comprising such chemotactic peptides are also within the scope of the present invention, although for such compositions, inclusion of a detectable moiety will not usually be required. More particularly, the present invention relates to a therapeutic composition comprising a chemotactic peptide

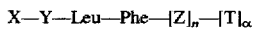

wherein:

X is an amino protecting group of the structure

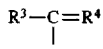

where $R^3$ is selected from the group consisting of hydrogen, alkyl, alkenyl, alkynyl, alkoxy, aralkoxy, and amino and $R^4$ is oxygen or sulfur, Y is an amino acid residue, Z is a spacer sequence selected from the group consisting of aliphatic diamines of 1 to 6 carbon atoms, $|R^6|_m$, and mixtures thereof, wherein $R^6$ is an amino acid residue and m is an integer greater than or equal to 1, n is 0 or 1, T is a therapeutic agent, and α is 0 or 1;

and wherein the chemotactic peptide substantially accumulates at the site of infection or inflammation and does not substantially accumulate at a site that is not infected or inflamed.

The present invention thus relates to an in vivo method of detecting a site or sites of infection or inflammation in an individual. This method comprises administering to the individual a detectably labeled chemotactic peptide wherein the peptide substantially accumulates at the site of infection or inflammation, but does not accumulate at uninfected, non-inflamed sites.

The invention also includes the various chemotactic peptides to which appropriate chelating molecules and detectable labels have been conjugated.

% of maximal superoxide production =E/M×100 where E is the amount of superoxide produced in the presence of an indicated concentration of peptide and M is the maximal amount of superoxide produced by the peptide.

For-NleLFK-HYNIC: HP1; For-MLFK-HYNIC: HP2; For-MLFNH(CH$_2$)$_6$NH-HYNIC: HP3; For-MLF-(D)K-HYNIC: HP4.

Figure 4:
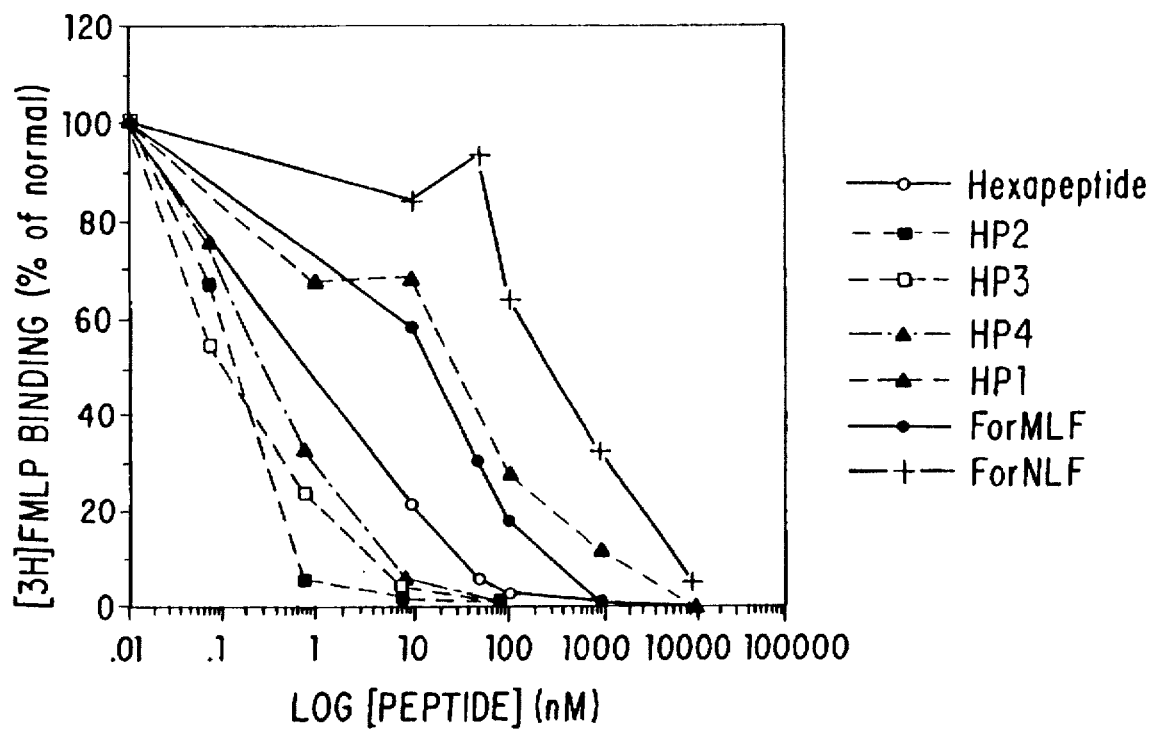

FIG. 4 Effect of chemotactic peptide analogs on For-ML |$^3$H|F binding to human PMN's. Intact human PMN's (8×10$^5$) were incubated with incubation buffer or the indicated concentration of peptide in the presence of 15 nM For-ML|$^3$H|F for 45 min at 24° C., following which the specific For-ML|$^3$H|F binding was determined.

% of maximal For-ML|$^3$H|F binding =E/C×100 where E is the specific cpm bound in the presence of the indicated concentration of unlabeled peptide and C is the specific cpm bound of For-ML|$^3$H|F in the presence of buffer alone. For-NleLFK-HYNIC: HP1; For-MLFK-HYNIC: HP2; For-MLFNH(CH$_2$)$_6$NH-HYNIC: HP3; For-MLF-(D)K-HYNIC: HP4.

Figure 5:
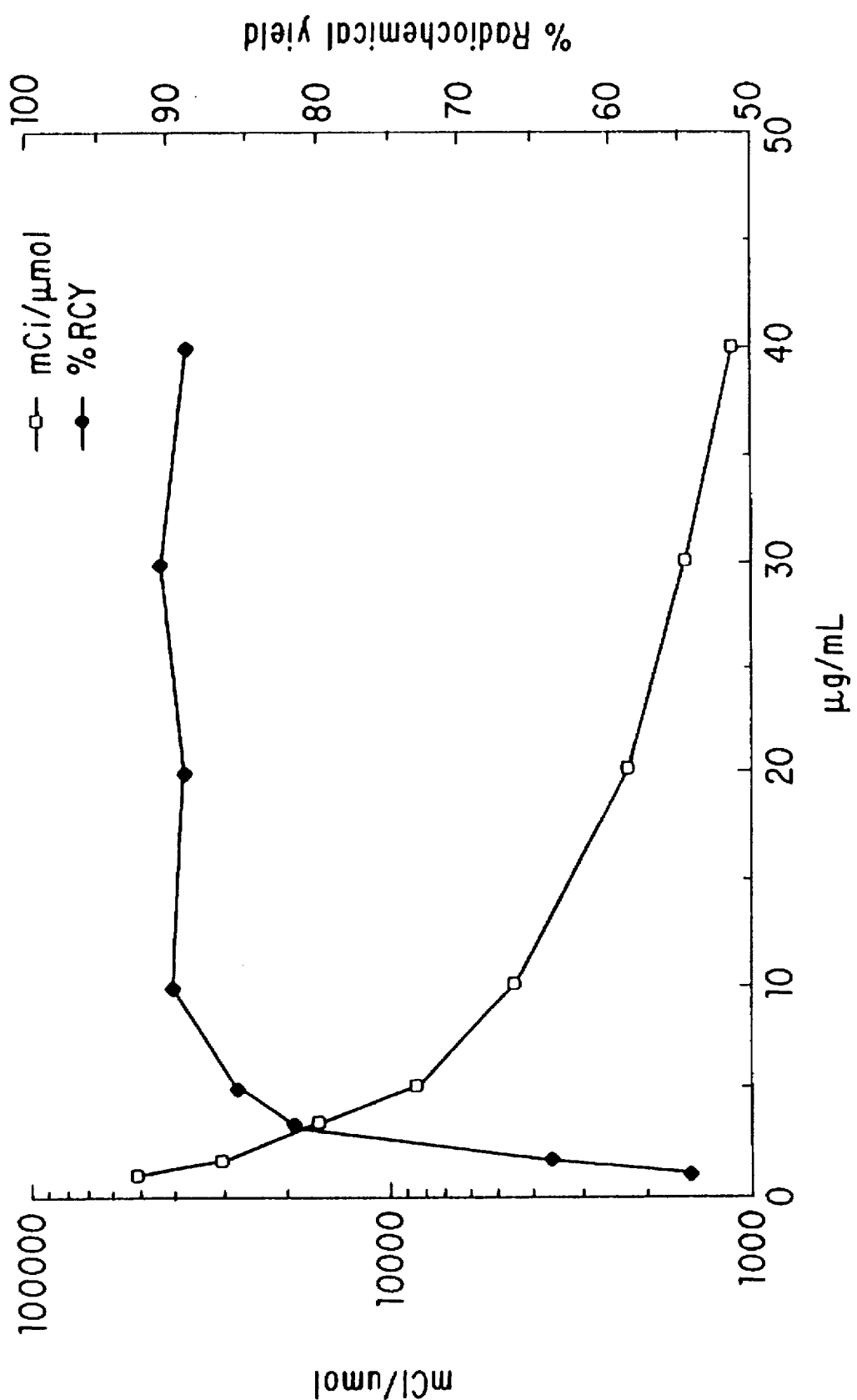

FIG. 5 Effect of peptide concentration on radiochemical yield (%) and specific activity (mCi/Mole). Data are shown for For-MLF-(D)K-HYNIC. Similar results were obtained with all peptides tested.

Figure 6:
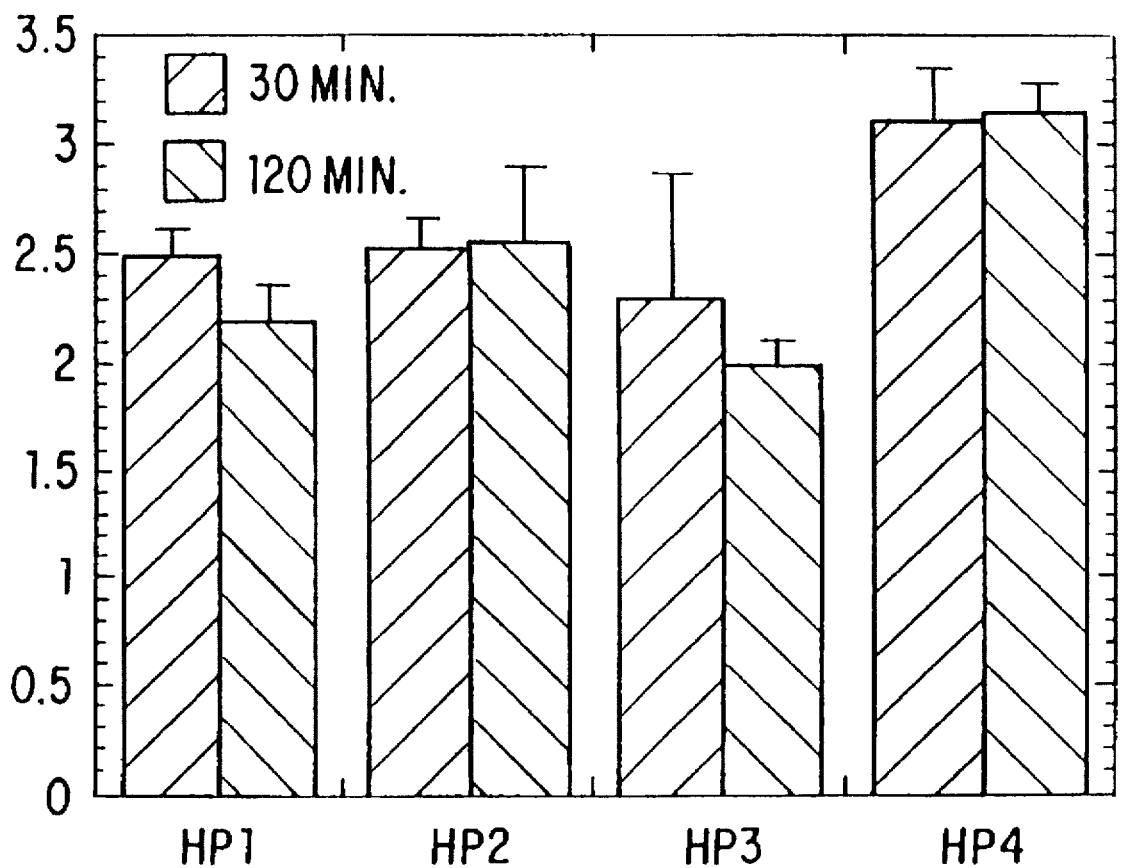

FIG. 6 Target-to-Background (T/B) ratios for $^{99m}$Tc labeled peptides in rats with E. coli infections. The data were calculated by dividing the %ID/gram in infected muscle by the corresponding value in contralateral normal muscle. In all cases, infections were established 24 hours prior to injection. Each point is the mean ± standard error of the mean (SEM) for 5 to 6 animals.

Figure 7:

FIG. 7 Representative gamma camera image of a rabbit with E. coli infection of the thigh after injection of a $^{99m}$Tc-labeled chemotactic peptide analog. The image was acquired at 17 hours after injection of approximately 1 mCi of $^{99m}$Tc labeled HP2. The infection was produced 24 hours prior to injection.

Figure 8:
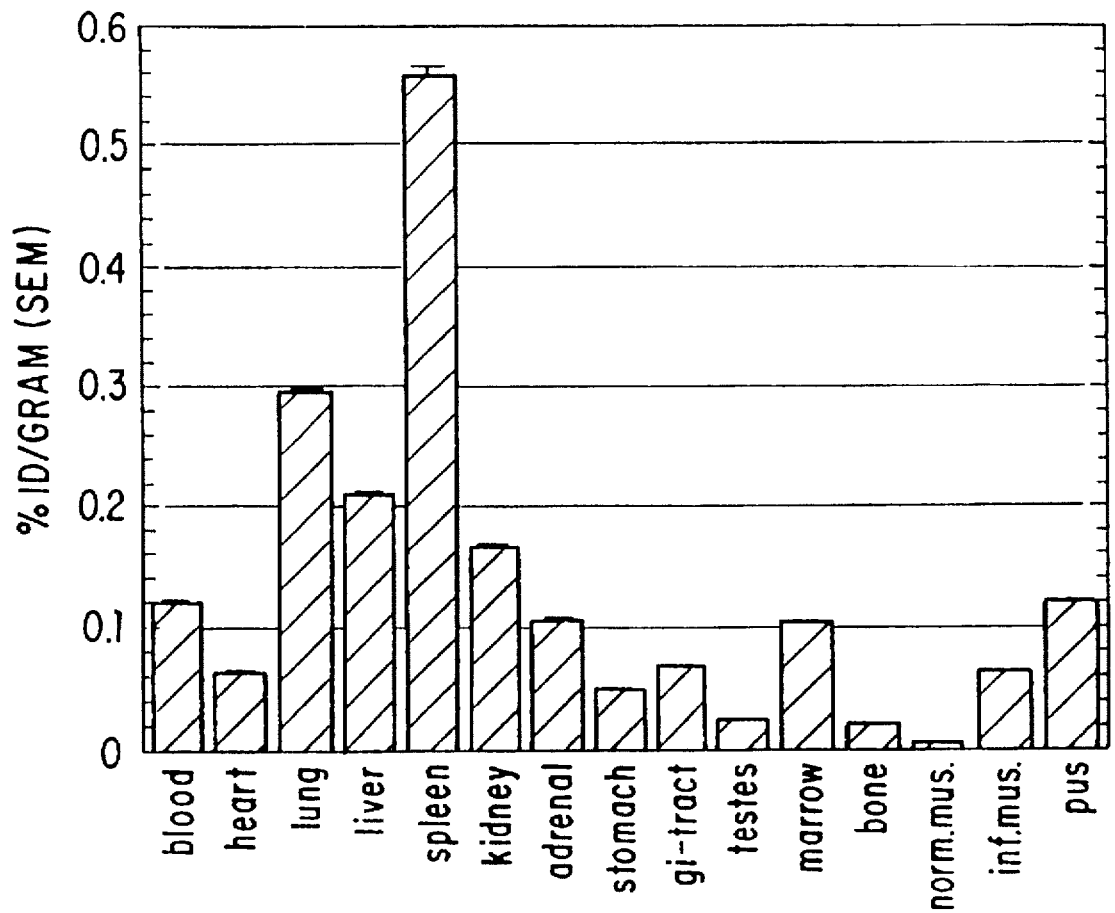

FIG. 8 Biodistribution in rabbits with an E. coli infection of the thigh 17 hours after injection of $^{99m}$Tc-labeled HP2. The data are presented as mean % injected dose/gram tissue. Error bars indicate SEM. The infection was produced 24 hours prior to injection of $^{99m}$Tc-labeled HP2.

Figure 9:
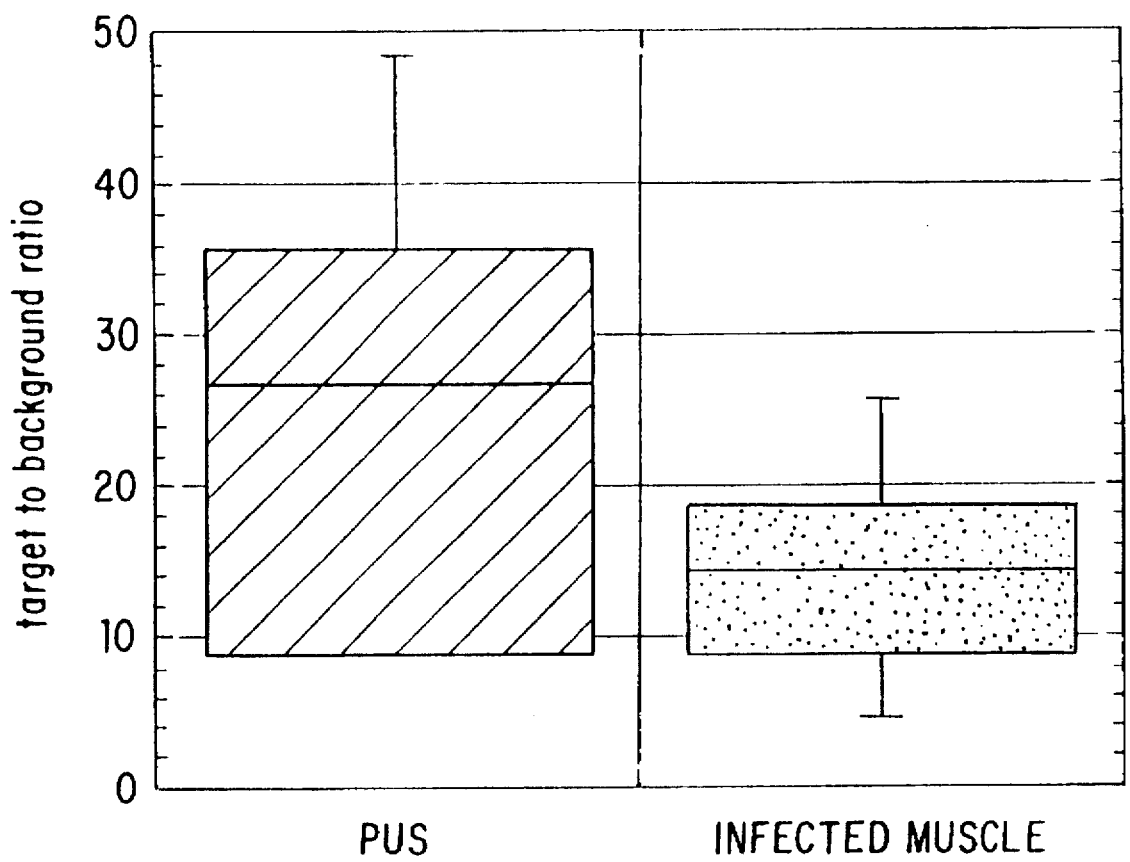

FIG. 9 Target-to-Background (T/B) ratios for $^{99m}$Tc-labeled HP4 in rabbits with E. coli infection 17 hours after injection. The data were calculated by dividing the % ID/gram in infected muscle or pus by the corresponding value in contralateral normal muscle. In all cases, infections were established 24 hours prior to injection. For infected muscle, the data comprise 28 samples from 6 animals. For pus, the data are 6 samples from 6 animals.

FIG. 10 The % injected dose/gram is shown for four preparations of HP3 in blood, lung, liver, spleen, kidney, and GI-tract at four time points after injection.

Figure 11:
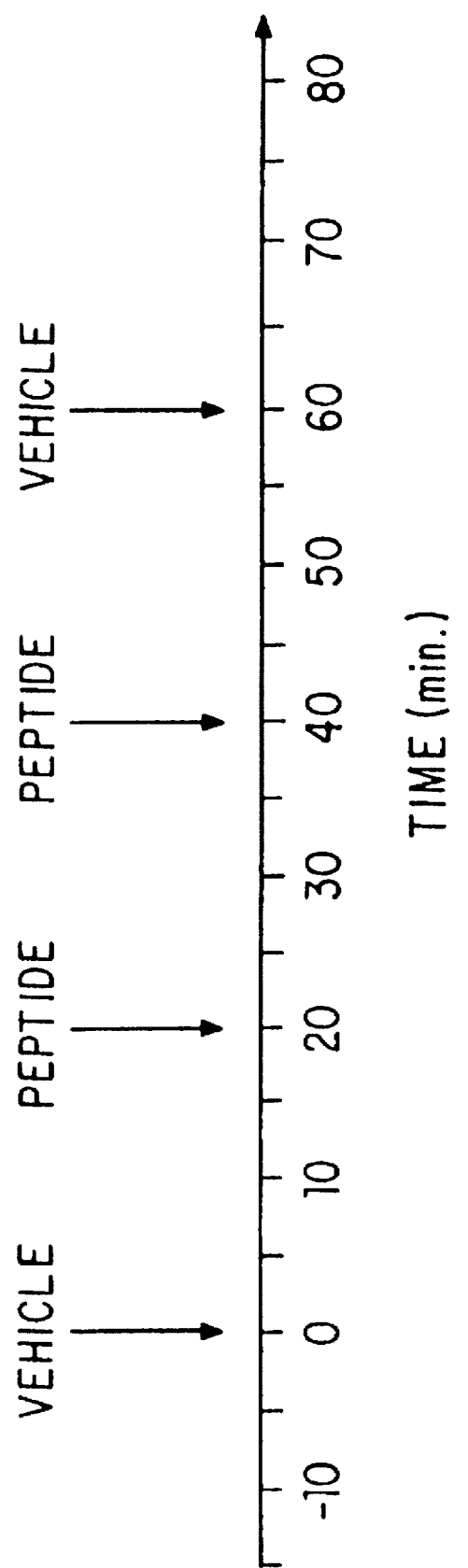

FIG. 11 This is a schematic diagram of the experimental protocol of Example 85, infra. Blood samples were collected for hematological measurements at −15, and −5 minutes and at 0.25, 0.50, 1, 3, 5, 10, and 20 minutes after the injections.

Figure 12D:
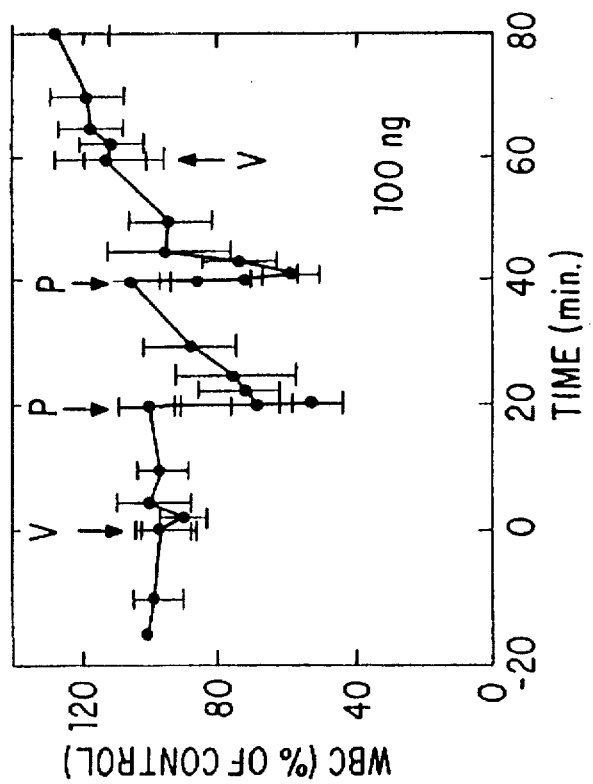
Figure 12C:
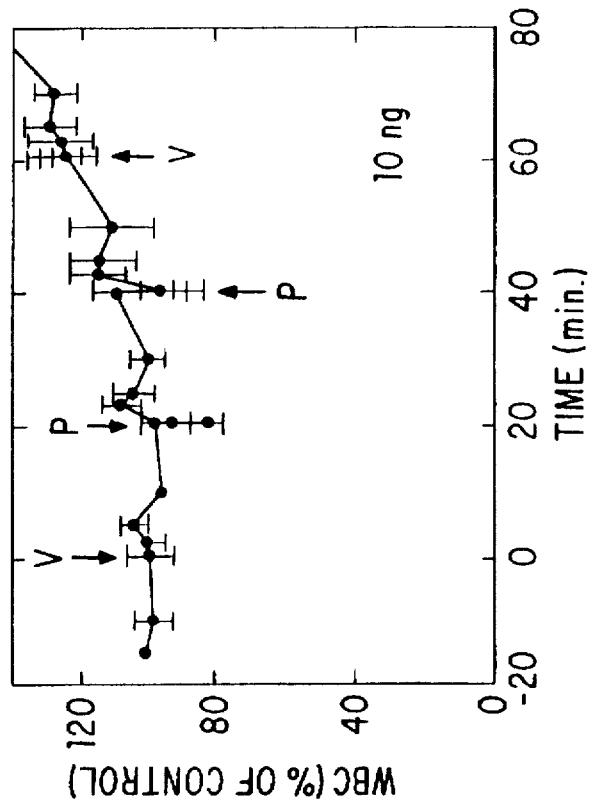

FIG. 12 Effect of ForNleLFNleYK-DTPA on peripheral WBC levels in monkeys. Total peripheral WBC count is expressed as percentage of the baseline level. Four doses of peptide (ng/kg) were used. P: peptide injection; V: vehicle injection.

Figure 13A:
Figure 13B:
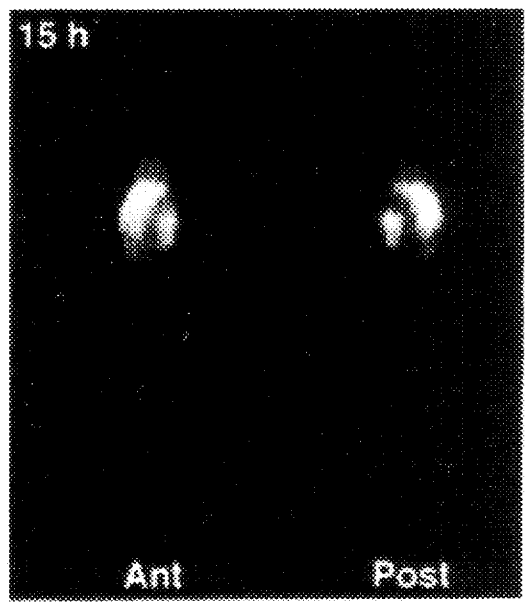

FIG. 13 Gamma camera images of a female Rhesus monkey with thigh inflammation at 3 and 12 hours after injection of $^{99m}$Tc-labeled (For-Met-Leu-Phe-NH-(CH$_2$)$_6$-NH-HYNIC. All images are normalized to the brightest pixel.

FIG. 14 Gamma camera images of a rabbit with an E. coli deep thigh infection at 6 and 18 hours after coinjection of $^{99m}$Tc-HP and $^{111}$In labeled leukocytes. The $^{99m}$Tc images were corrected for $^{111}$In photons in the $^{99m}$Tc window. All images were normalized to the total number of counts in the early $^{99m}$Tc-HP image. Infections were established 24 hours prior to injection.

Figure 15:
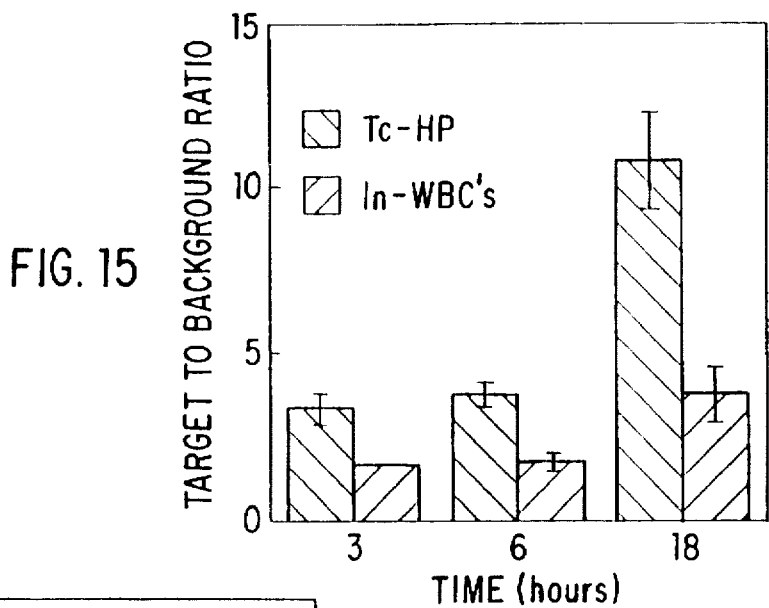

FIG. 15 Target-to-Background ratios of $^{99m}$Tc-HP and $^{111}$In-WBC's from ROI analysis of scintigraphs at 3, 6, and 18 hours after injection. Each point is the mean ± SEM for 6 animals. In all cases, the animals were infected 24 hours prior to injection of radiotracers.

Figure 16:
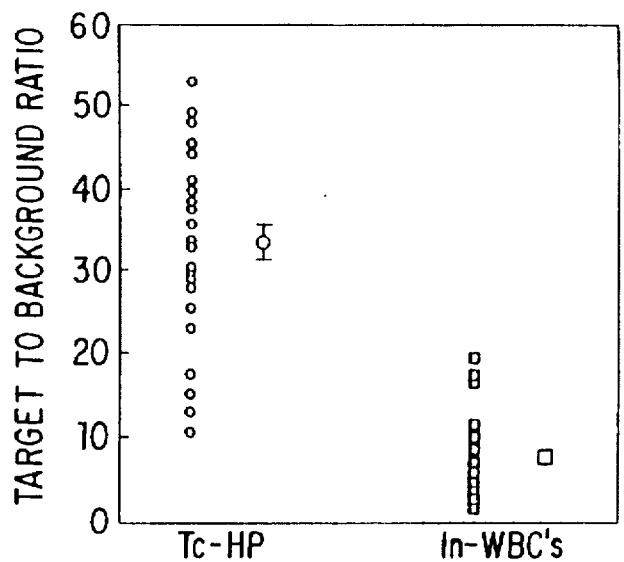

FIG. 16 Target-to-Background ratios for $^{99m}$Tc-Hp and $^{111}$In-WBC's determined by direct radioactivity measurements on samples of excised tissues at 18 hours after injection. Small circles represent all values (30 samples from 6 animals) for $^{99m}$Tc-HP, the large circle is the mean ± SEM. Small squares represent all values (30 samples from 6 animals) for $^{111}$In-WBC's, the large square is the mean ± SEM. In all cases, the animals were infected 24 hours prior to injection.

Figure 17:
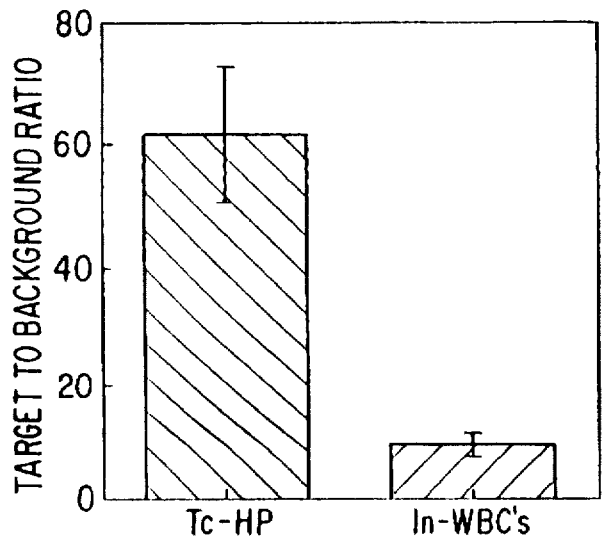

FIG. 17 Pus to normal muscle ratios for $^{99m}$Tc-HP and $^{111}$In-WBC's determined by direct radioactivity measurements on samples of excised tissues at 18 hours after injection. Each point is the mean ± SEM of 6 animals. In all cases, the animals were infected 24 hours prior to injection.

DESCRIPTION OF THE PREFERRED EMBODIMENTS

The terms "inflammation" and "site of inflammation" are used to denote conditions and their locations that occur in an individual due to tissue damage, regardless of the underlying cause or etiology. This tissue damage can result form microbial invasion, autoimmune processes, tissue or organ allograft rejection, or such injurious external influences as heat, cold, radiant energy, electrical or chemical stimuli, or mechanical trauma. Whatever the cause or body site, the ensuing inflammatory response is quite similar, consisting of a complicated set of functional and cellular adjustments, involving the changes in microcirculation, movement of fluids, and influx and activation of inflammatory cells (leukocytes).

The term "infection" denotes invasion by bacteria, viruses, fungi, protozoa, and other microorganisms.

The term "individual" is meant to include animals, e.g. mammals, particularly humans.

The term "agonist" as used herein is a chemotactic peptide that binds to a receptor and stimulates the receptor's function.

The term "antagonist" as used herein is a chemotactic peptide that prevents receptor stimulation. A chemotactic peptide that is an antagonist has an affinity for a cell receptor and, by binding to it, prevents the cell from responding.

The term "diagnostically effective" as applied herein to dosage means that the amount of detectably labeled chemotactic peptide administered is sufficient to enable detection of a site of infection or inflammation over and above any background signal.

Generally, the dosage of detectably labeled chemotactic peptide for diagnosis will vary depending on considerations such as age, condition, sex, and extent of disease in the patient, counterindications, if any, and other variables, and will be adjusted by the physician in attendance. Dosage can vary from about 0.01 µg/kg to about 2,000 µg/kg, preferably about 0.1 µg/kg to about 1,000 µg/kg.

The term "terminal-modified chemotactic peptide" is meant to include, but is not limited to, molecules having the following general structure:

wherein:

X is an amino-protecting group,

Y is an amino acid residue,

Z is a spacer sequence, n is 0 or 1, and

W is a labeling or attachment substituent.

In the above general structure, X is an amino-protecting group, that is, a group that protects amino groups, and may be any of the many groups known to those skilled in the art to be useful for this purpose. The following schematic diagram illustrates several useful synthetic routes by which amino-protecting groups may be added onto a chemotactic peptide:

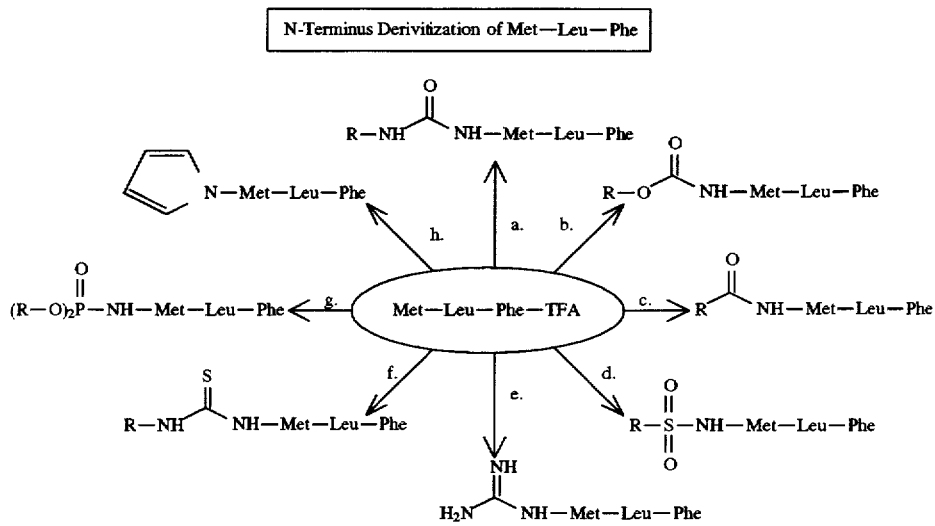

-continued a. 1. RNCO, Et₃N, DMF; 2. H₃O⁺
b. 1. ROCOCl, Et₃N, DMF; 2. H₃O⁺
c. 1. RCOCl, Et₃N, DMF; 2. H₃O⁺
d. 1. RSO₂Cl, Et₃N, DMF; 2. H₃O⁺
e. 1.1-pyrazole-1-carboxamide-hydrochloride, Et₃N, DMF; 2. H₃O⁺
f. RNCS, Et₃N, DMF; 2. H₃O⁺
g. 1.(RO)₂POCl, Et₃N, DMF; 2. H₃O⁺
h. 2,5-dimethoxytetrahydrofuran, NaOAc, AcOH Generally, when conceptualizing the amino-protecting group, i.e., the N-terminus protecting group, on a chemotactic peptide ("CP"), it may be most accurate to view the moiety as a singular unit rather than a "bulky" group separated from the CP by a "spacer". It is likely that both of these portions of the protecting group interact with the receptor via steric, electrostatic, and hydrophobic interactions. Hence, the composition of the protecting group as a whole will ultimately determine the activity of the CP. This concept is supported, for example, by the observation that an n-butyl carbamate protected CP is nearly 10-fold less active than the corresponding n-butyl urea protected CP. These two protecting groups have identical aliphatic side chains, but different bond angles, degrees of rotation, and electrostatic characteristics.

Upon switching the CP N-protection from carbamate (urethane) to a urea, it is likely that the overall shape of the N-terminus will be changed. The urea will have different bond angles and significantly less freedom of rotation (there is less rotation about a carbonyl-N bond than a carbonyl-O bond). These effects may have some effect on the overall fit into the CP-receptor.

The electrostatic behavior of the N-terminus end of the CP will be changed with the incorporation of a urea. These electrostatic differences may lead to changes in hydrogen bonding interactions within the receptor.

The overall size of a urea will not be significantly different from that of a carbamate. Once again, however, there is the possible exception that the hindered rotation of the urea may lock it into a specific conformation that has a marked effect on its fit into the receptor. This relates more to shape than overall size.

Perhaps the most rational reason for equipping the N-terminus of a CP with a urea protecting group is that the urea is more stable to a wider range of conditions than is a carbamate. Hence, its stability under highly acidic conditions permits a wider range of chemical transformations on the linker moiety on the C-terminus.

Other related amino-protecting groups are also within the scope of the invention, such as: ureas containing a heteroatom, thioureas, sulfonamides, phosphonamides, guanidines, and sulfonyl ureas.

The literature discloses a number of other amino-protecting groups, e.g., t-butyloxycarbonyl, acetyl, benzyloxycarbonyl, formyl, thioformyl, cyanoamidine and methoxycarbonyl.

Effective chemotactic agents (be they agonists or antagonists) can also be produced by protecting their amino termini with i-butyloxycarbonyl and alkyl ($C_3$–$C_6$ both branched and cyclic) carbamoyl.

A number of amino-protecting groups suitable for chemotactic peptides are listed below. The synthetic procedures for the protecting groups are referenced in "Protecting Groups In Organic synthesis"; John Wiley & Sons: New York, 1981; Chapter 6.

a. Carbamates:
Cyclopropylmethyl carbamate
1-Methyl-1-cyclopropylmethyl carbamate
Diisopropylmethyl carbamate
2-Methylthioethyl carbamate
1,1-Dimethylpropynyl carbamate
t-Amyl carbamate
Cyclopentyl carbamate
Cyclohexyl carbamate
9-Fluorenylmethyl carbamate
1-Adamantyl carbamate
1,1-Dimethyl-2-2-trichloroethyl carbamate
2,2,2-Trichloroethyl carbamate
1-Methyl-1-phenylethyl carbamate
2,4-Dichlorobenzyl carbamate b. Carboxamides and their corresponding thiocarboxamides
Thiophene carboxamide
Adamantyl carboxamide
4-Bromobutyryl carboxamide
Cinnamyl carboxamide
Nicotinoyl carboxamide c. Ureas, their corresponding thioureas and their corresponding cyano guanidine derivatives
Benzyl urea
2,4-Difluorophenyl urea
1-Naphthyl urea
Phenyl urea
Diphenyl urea
Propyl urea
Heteroureas d. Sulfonamides
Benzenesulfonamide
Dimethoxybenzene sulfonamide
Toluenesulfonamide
Benzylsulfonamide
Trifluoromethylsulfonamide e. Phosphonamides
Benzenephosphonamide
Dimethoxybenzene phosphonamide
Toluenephosphonamide
Benzylphosphonamide
Trifluoromethylphosphonamide In a preferred embodiment of the present invention, X is $$R^3-\underset{|}{C}=R^4$$

where $R^3$ is selected from the group consisting of hydrogen, alkyl, alkenyl, alkynyl, alkoxy, aralkoxy, and amino and $R^4$ is a chalcogen, preferably, oxygen or sulfur.

Where $R^3$ is alkyl, it is preferred that it be an alkyl of 1–6 carbon atoms, more preferably, 3–6 carbon atoms, i.e., methyl, ethyl, propyl, butyl, pentyl, hexyl, or isomers thereof, e.g., isopropyl, isobutyl, sec-butyl, tert-butyl, neopentyl, 2-ethylbutyl, and the like. Isobutyl and t-butyl groups are most preferred.

Where $R^3$ is alkenyl, it is preferred that it be an alkenyl of 2–6 carbon atoms, more preferably 2–4 carbon atoms, i.e., ethenyl, propenyl, butenyl, pentenyl, hexenyl, and isomers thereof, e.g., isopropenyl, isobutenyl, sec-butenyl, tert-butenyl, neopentenyl, 2-ethylbutenyl, and the like.

Where $R^3$ is alkynyl, it is preferred that it be an alkynyl of 2–6 carbon atoms, more preferably 2–4 carbon atoms, i.e., ethynyl, propynyl, butynyl, pentynyl, hexynyl, and isomers thereof, e.g., isopropynyl, isobutynyl, sec-butynyl, tert-butynyl, neopentynyl, 2-ethylbutynyl, and the like.

Where $R^3$ is alkoxy, it is preferred that it be an alkoxy of 1–6 carbon atoms, more preferably, 3–6 carbon atoms, i.e., methoxy, ethoxy, propoxy, butoxy, pentoxy, hexoxy, or isomers thereof.

Where $R^3$ is aralkoxy, it is preferably benzoxy, i.e., $\Phi$—$CH_2$—O—, wherein the phenyl group ($\Phi$) may be substituted or unsubstituted.

Where $R^3$ is amino, it is preferably of the structure —N(H)$R^5$, where $R^5$ is selected from the group consisting of hydrogen, alkyl, cycloalkyl, and aryl.

Where $R^5$ is alkyl, it is preferably an alkyl of 1–4 carbon atoms, more preferably, 3–4 carbon atoms, i.e., methyl, ethyl, propyl, butyl, or isomers thereof, e.g., isopropyl, isobutyl, sec-butyl, tert-butyl.

Where $R^5$ is cycloalkyl or aryl, it is preferably cyclopentyl, cyclohexyl, adamantyl, phenyl, or diphenyl, more preferably, cyclohexyl or phenyl, which groups may be substituted or unsubstituted.

Y in the above described general structure is an amino acid residue and can be any such residue useful for the purpose. In a preferred embodiment of the present invention, Y is

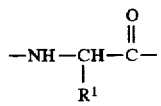

where $R^1$ is benzyl, alkyl, or —$CH_2$—$CH_2$—$R^2$—$CH_3$ and

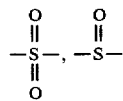

Where $R^1$ is alkyl, it is preferred that it be an alkyl of 1–6 carbon atoms, i.e., methyl, ethyl, propyl, butyl, pentyl, hexyl, or isomers thereof, e.g., isopropyl, isobutyl, sec-butyl, tert-butyl, neopentyl, 2-ethylbutyl, and the like. More preferably, $R^1$, where it is alkyl, is an alkyl of 3–4 carbon atoms.

In another preferred embodiment of the present invention, Y is 4-aminotetrahydropyran-4-carboxylic acid (Thp). Thp yielded an analog that was a chemoattractant agent to human neutrophils, but did not stimulate superoxide production. The peptide that was prepared and tested was formyl-Thp-Leu-Phe-OMe.

In the above general structure, Z is a spacer sequence of any useful length. It may or may not be present, depending upon whether n is 0 or 1. Where n is 1, Z is present and is preferably an aliphatic diamine or $[R^6]_m$, where $R^6$ is an amino acid residue and m is an integer greater than or equal to 1, preferably an integer of from 1 to 3. Z may also be a combination of an aliphatic diamine and $[R^6]_m$.

Where Z is an aliphatic diamine, it is preferably an aliphatic diamine of from 1 to 6 carbon atoms, e.g., methylene diamine, ethylene diamine, propylene diamine, tetramethylene diamine, pentamethylene diamine, and hexamethylene diamine. More preferably, where Z is an aliphatic diamine, it will be one having from 4 to 6 carbon atoms, e.g., tetramethylene diamine (also known as cadaverine), pentamethylene diamine (also known as putrescine, hereinafter Pu), and hexamethylene diamine.

Where Z is $[R^6]_m$, there will be one or more amino acid residues, depending upon the value of m. Where two or more residues are present, they may be the same or different. The amino acid(s) of which the spacer sequence is comprised may be any of those well-known to those skilled in the art, either essential or non-essential. For example, $R^6$ may be, either alone or in combination, arginine, glutamic acid, lysine, aspartic acid, valine, cysteine, leucine, isoleucine, norleucine, methionine, histidine, proline, tryptophan, tyrosine, asparagine, glutamine, serine, threonine, alanine, glycine, or phenylalanine. Preferred amino acid residues for use as a spacer sequence in the practice of the present invention are, either alone or in combination, norleucine, tyrosine, aspartic acid, lysine, leucine, and phenylalanine.

As stated above, W is a labeling or attachment substituent. W represents a moiety by which the chemotactic peptide employed in the practice of the present invention may be detectably labeled. The term "detectably labeled" means that the chemotactic peptide has attached to it a diagnostically detectable label.

There are many different labels and methods of labeling known to those skilled in the art. Examples of the types of labels that can be used in the present invention include radioactive isotopes, paramagnetic isotopes, and compounds that can be imaged by positron emission tomography (PET). Those skilled in the art will know of other suitable labels for binding to the chemotactic peptides used in the invention, or will be able to ascertain such using routine experimentation. Furthermore, the binding of these labels to the chemotactic peptide can be done using standard techniques common to those skilled in the art.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention.

Another important factor in selecting a radionuclide for in vivo diagnosis is that its half-life be long enough that it is still detectable at the time of maximum uptake by the target tissue, but short enough that deleterious radiation of the host is minimized. In one preferred embodiment, a radionuclide used for in vivo imaging does not emit particles, but produces a large number of photons in a 140–200 keV range, which may be readily detected by conventional gamma cameras.

For in vivo diagnosis, radionuclides can be bound to chemotactic peptides either directly or indirectly by means of an intermediary functional group. Intermediary functional groups that are often used to bind metal ion radioisotopes to chemotactic peptides are the chelating agents, diethylene triamine pentaacetic acid (DTPA) (Hnatowich, D. J., *Int. J. Appl. Radiat. Isot.*, 33:327–332, (1982)) and ethylene diamine tetraacetic acid (EDTA). Other common chelating groups for linking Tc to peptides include dioxime ligands (1), functionalized cyclams (2), $N_2S_2$ ligands (3), and $N_3S$ ligands (4). Alternatively, a reactive thiol can be attached to a lysine residue via iminothiolane (5) or thiol residues can be conjugated to a peptide using an amino acid sequence containing one or more cys residues.

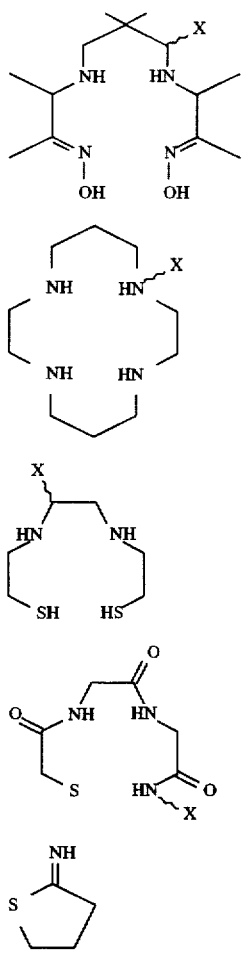

Examples of metallic ions that can be bound to chemotactic peptides are $^{99m}$Tc, $^{123}$I, $^{131}$I, $^{97}$Ru, $^{67}$Cu, $^{67}$Ga, $^{125}$I, $^{68}$Ga, $^{72}$As, $^{89}$Zr, and $^{201}$Tl. $^{99m}$Tc and $^{111}$In are preferred.

$^{111}$In-labeled chemotactic peptides are effective agents for the external imaging of focal sites of infection in rats (Fischman, A. J.J. Nucl. Med. 32:483–491 (1991)). However, the short biological half-time of the peptides reduces the usefulness of $^{111}$In ($t_{1/2}$: 67.9 h) for imaging. Owing to its short physical halflife, high specific activity, excellent imaging properties, low cost, and widespread availability, $^{99m}$Tc is the ideal radionuclide for labeling chemotactic peptides. Although numerous techniques have been used for $^{99m}$Tc labeling, the hydrazino nicotinamide group (HYNIC) has been especially promising. The active succinimidyl ester of hydrazinonicotinic acid (SHNH) has been successfully used to derivatize the epsilon amino groups of lysine residues in proteins. Incubation of these conjugates with simple complexes possessing the Tc(V) oxo core such as $^{99m}$Tc-glucoheptonate results in quantitative labeling (Abrams, M. J., et al., J. Nucl. Med. 31:2022–2028 (1990)).

The labelling of macromolecules with $^{99m}$Tc can be classified into three principal methods: direct labelling, bifunctional chelates, and preformed chelates. The currently preferred method for labeling using the HYNIC (SHNH) linker is the use of an ancillary ligand, for example, reduction of pertechnetate ion in the presence of a chelating precursor to form the labile $^{99m}$Tc-precursor complex, referred to herein as an "ancillary ligand", which, in turn, reacts with the metal binding group of a bifunctionally modified CP to form a $^{99m}$Tc-CP conjugate. As stated above, $^{99m}$Tc-glucoheptonate ancillary ligand can be used to radiolabel proteins that have been modified with SHNH groups (Schwartz, D. A., et al., Bioconjugate Chem. 2:333–336 (1991)). However, this requires a sixty minute incubation and specific activities greater than 25 mCi/mg to achieve radiolabelling yields greater than 90%. The polyhydroxyamino acid tricine can be used as a more efficient and facile labelling precursor for $^{99m}$Tc labelling of SHNH modified polypeptides and proteins.

Tricine, tris(hydroxymethyl)methylglycine, and analogues thereof, can be formulated in aqueous solutions, pH 6–8, with stannous chloride reducing agent for the spontaneous formation of $^{99m}$Tc precursors. Analysis for the formation of "Tc-tricine" ancillary ligands is performed on ITLC-SG strips, similar to $^{99m}$Tc-glucoheptonate analysis, using saline for the quantitation of TcSn colloid at the origin and methylethylketone for the quantitation of pertechnetate at the solvent front. Solutions of "Tc-tricine" (36 mg/ml precursor, 50 µg/ml stannous chloride, pH 6.0), under similar conditions to $^{99m}$Tc-glucoheptonate, radiolabelled SHNH modified IgG to greater than 90% in minutes at room temperature. Additionally, solutions of "Tc-tricine" can achieve >90% radiolabelling of IgG-SHNH at specific activities greater than 150 mCi/mg protein as compared to Tc-glucoheptonate. The utility of quantitative radiolabelling at high specific activities is more important in the labelling of SHNH modified small molecules, e.g., CP's.

HYNIC modified peptides can be labelled by the following general procedure:

Generator eluted $^{99m}$TcO$_4^-$ (30 mCi/ml) is added in equal volume with stirring to a freshly prepared solution of Sn/tricine (72 mg/ml tricine, pH 7.0–7.2, 100 µg/ml SnCl$_2$.2H$_2$O). The production of $^{99m}$Tc-tricine is determined by ITLC-SG 1×8 cm strips using saline or methylethylketone eluants for the determination of colloid or pertechnetate, respectively. The $^{99m}$Tc-tricine is added without waiting for a peptide solution. A 1 mg/ml solution of the peptide, e.g., an ibocMLF-HYNIC hydrazone, can be prepared by dissolving 1 mg of peptide in 600 µL of ethanol and adding 400 µL of slightly acidic water. Upon standing for thirty minutes to deprotect the hydrazone, the peptide is diluted 1:10 with acetate buffer pH 5.2. The $^{99m}$Tc-peptide conjugate is prepared by mixing 100 µL of $^{99m}$Tc-tricine with 15 µL of peptide solution. After incubating for one hour, the percent yield of $^{99m}$Tc-peptide is determined by ITLC-SG 1×8 cm strips using 25% w/w NaCl solution as eluant, where the $^{99m}$Tc-peptide remains at the origin and all other species elute to the solvent front.

Examples of suitable chemotactic peptides include, without limitation:

N-For-Nle-Leu-Phe-Nle-Tyr-Lys-DTPA

N-For-Met-Leu-Phe-Pu-DTPA

N-For-Nle-Leu-Phe-Lys-DTPA

N-For-Nle-Leu-Phe-Lys(NH$_2$)-DTPA

N-For-Met-Leu-Phe-Lys-DTPA

N-For-Met-Leu-Phe-D-Lys (NH$_2$)-DTPA

N-Ac-Nle-Leu-Phe-Lys(NH$_2$)-DTPA

N-Carbobenzoxy-Met-Leu-Phe-Methyl Ester

IBOC -L-Methionyl(sulfoxide)-L-Leu-L-Phe-L-lysinamide

IBOC-L-Norleucyl-L-Leu-L-Phe-L-lysinamide

N-For-L-Methionyl (sulfoxide)-L-Leu-L-Phe-DTPA-L-Lys

N-For-L-Methionyl (sulfone)-L-Leu-L-Phe-N-DTPA-L-Lys

N-Isobutylurea-Met-Leu-Phe-carboxylate

Isobutyloxycarbonyl-Met-Leu-Phe-N-DTPA-Lys

N-For-(D)-Met-Leu-Phe-Lys Amide Solvated t-BOC-Nle-Leu-Phe-Lys Solvated

N-For-Methionyl-Sulfoxide-Leu-Phe-Lys Amide Solvated

N-For-Methionyl-Sulfone-Leu-Phe-Lys Amide Solvated

N-Carbamyl-Met-Leu-Phe-Lys Amide Solvated

N-Trimethylacetyl-Met-Leu-Phe-Lys Amide Solvated

Isobutyloxycarbonyl-Met-Leu-Phe-Lys Amide Solvated

N-For-Nle-Leu-Phe-Nle-Tyr-$N^6$-DTPA-Lys

Isopropylurea-Met-Leu-Phe-Lys-SHNH-BOC

Isopropylurea-Met-Leu-Phe-n-propyldiamine-Asp-SHNH HBr

Isopropylurea-Met-Leu-Phe-Lys-Asp-SHNH HBr

Isopropylurea-Met-Leu-Phe-Lys-SHNH HBr

N-Phenylurea-Met-Leu-Phe

Isopropylurea-Met-Leu-Phe-Propane diamine-SHNH

N-n-Butyl-thiourea-Met-Leu-Phe

N-n-butylurea-Phe-Leu-Phe-Leu-Phe

N-isopropylurea-Phe-Leu-Phe-Leu-Phe—COOH iBOC-Met-Leu-Phe—COOH iBOC-Met-Leu-Phe|amido(propylamido)carboxy[(propyl) carboxy)]-(amido propanol SPNH) ester N-isobutylurea-Met-Leu-Phe-Carboxylate N-n-Propyl-urea-Met-Leu-Phe N-t-Butyl-urea-Met-Leu-Phe N-n-Butyl-urea-Met-Leu-Phe iBOC-Met-Leu-Phe-(amido ethoxy ethyl [3-amido]-6-propenal hydrazone)-pyridine N-iBOC-Met-Leu-Phe-SPNH-thioester N-isopropylurea-Met-Leu-Phe N-iBOC-Met-Leu-Phe-Propylene diamine-SPNH Cyclohexyl-urea-Met-Leu-Phe—COOH N-n-Butyl carbamate-Met-Leu-Phe-Methyl ester N-iBOC-Met-Leu-Phe-Methyl ester N-Methyl carbamate-Met-Leu-Phe-Methyl ester N-Adamantylurea-Met-Leu-Phe N-Cinnamoyl-Met-Leu-Phe P-Tolylurea-Met-Leu-Phe M-Tolylurea-Met-Leu-Phe N-Cinnamoyl-Phe-Leu-Phe-Leu-Phe In addition to identifying and characterizing sites of local infection and inflammation, the method of the invention can be used to monitor the course of inflammation in an individual. Thus, by measuring the increase or decrease in the size or number of inflammation sites, it is possible to determine whether a particular therapeutic regimen aimed at ameliorating an infection or other cause of the inflammatory process, or directed to the inflammatory process itself, is effective.

In another embodiment, the invention is used for diagnosing the specific underlying cause of the inflammation at the site. In this method an individual suspected of having an inflammatory site is first given a diagnostically effective amount of chemotactic peptide, as previously described, and then photographically imaged to determine the presence and location of the site.

The chemotactic peptides employed in the practice of the present invention can be agonists or antagonists. In some cases, a given peptide may be both, depending upon the concentration at which it is used.

The peptides iBoc-MLFK and iBoc-MLFK-DTPA antagonize the ForMLF stimulated release of free radicals from neutrophils, as well as the adhesion of the activated neutrophils to vascular endothelial cells in vitro. Antagonist activity is retained with modification of the C-terminus with the $^{111}$Indium linker DTPA. These peptides do not demonstrate any agonist activity.

An in vivo imaging study was conducted comparing the agonist peptide formyl-norleucyl-leucyl-phenylalanyl-norleucyl-tyrosyl-lysine-DTPA (For-NleLFNleYK-DTPA) and the antagonist peptide iBoc-MLFK-DTPA. The $^{111}$In-labeled peptides localized to the infection site rapidly. The localization was confirmed both by gamma camera images and by tissue biodistribution. The major difference between the two peptides was that the agonist peptide localized to areas such as lung, spleen, and bone marrow, indicative of cell activation and margination, while the antagonist peptide did not. The agonist peptide induced a transient drop in the white blood cell count (neutropenia), whereas the antagonist peptide had no significant effect. These results are as expected for an agonist versus an antagonist. The agonist peptide demonstrated an improving target to background ratio over 5 hours, whereas the antagonist peptide was maximally effective at 1 hour. This suggests that a higher binding affinity, as with the agonist peptide, may result in improved target to background ratios as well as having a therapeutic advantage. These results are also of interest because it had not previously been known whether or not an antagonist would exhibit imaging capability. Such capability was not obvious to those skilled in the art because there was a possibility that activation via an agonist might be required for binding and imaging. It was discovered that this was not the case.

The antagonist peptide t-Boc-Phe-Leu-Phe-Leu-Phe inhibits neutrophil mediated lysosomal enzyme release. In addition, other urethane N-terminal blocking groups do not convert peptides to antagonists, but rather to agonists (methoxycarbonyl and carbobenzoxy). The N-terminal iBoc protecting group also is suitable for an antagonist peptide and an iBoc peptide modified by DTPA at the C-terminal lysine maintains appropriate biological activity.

The present invention advances the art by showing that the disease-related neutrophil functions of adhesion to endothelium and release of free radicals are inhibited by the antagonist iBoc-MLFK. This peptide also localizes the diseased site in vivo. In addition, it does this without altering white blood cell number. These results are consistent with the use of an adhesion cascade-blocking antagonist peptide, and potentially other antagonists, as therapeutic and diagnostic agents for infection/inflammation diseases.

PEPTIDE BACKBONE MODIFICATIONS

It is also within the scope of the present invention to substitute other compounds for one of the Leu or Phe moieties of the above-described general structure.

a. Leucine

Replacement of the leucine residue with dipropylglycine (Dpg), yielded an analog that was a chemoattractant agent to human neutrophils. The peptide that was prepared and tested was formyl-Met-Dpg-Phe—OH Replacement of the leucine residue with 1-aminocyclohexanecarboxylic acid ($Acc^6$) yielded an analog that was a potent inducer of lysozyme release in rabbit neutrophils. The peptide that was prepared and tested was formyl-Met-Acc$^6$-Phe—OH.

b. Phenylalanine

Replacement of the phenylalanine residue with z-dehydrophenylalanine (z-Phe), yielded an analog that stimulated superoxide production by rabbit neutrophils. The compound that was prepared and tested was formyl-Met-Leu-z-Phe-OMe.

Literature references for the preparation of replacement amino acids for backbone modification are listed below:

a) 4-aminotetrahydrothiopyran-4-carboxylic acid (methionine replacement) is disclosed in Torrini et al., *Indian Journal of Peptide Protein Research* 38:495–504 (1991);

b) dipropylglycine and 1-aminocyclohexanecarboxylic acid (leucine replacements) are disclosed in Dentino et al., *The Journal of Biological Chemistry* 28:18460–18468 (1991);

c) z-dehydrophenylalanine (phenylalanine replacement) was prepared using the method described in Chauhan et al., *Tetrahedron* 44:2359–2366 (1988);

d) 2-aminoindanone-2-carboxylic acid (phenylalanine replacement) was disclosed in Gavuzzo et al., *Indian Journal of Peptide Protein Research* 37:268–276 (1991); and e) anilinoglycine (phenylalanine replacement) was prepared as described in Kraus et al., *European Journal of Medicinal Chemistry* 27:19–26 (1992).

In another embodiment of the invention, the chemotactic peptides can be "therapeutically conjugated" and used to deliver a therapeutic agent to the site of infection or inflammation. The term "therapeutically conjugated" means that the chemotactic peptide is conjugated to a therapeutic agent. Therapeutic agents used in this manner are directed either to the underlying cause of the inflammation, for example, the infectious organisms or a tumor, or to components of the inflammatory process themselves. Examples of agents used to treat inflammation are the steroidal and non-steroidal anti-inflammatory drugs. Many of the non-steroidal anti-inflammatory drugs inhibit prostaglandin synthesis.

Other therapeutic agents that can be coupled to the chemotactic peptides according to the method of the invention are drugs, radioisotopes, lectins, toxins, and antimicrobial agents. The therapeutic dosage administered is an amount that is therapeutically effective and will be readily determinable by those skilled in the art. The dosage is also dependent upon the age, health, and weight of the recipient, kind of concurrent treatment, if any, frequency of treatment, and the nature of the effect desired, such as, for example, anti-inflammatory effects or anti-bacterial effects.

Lectins are proteins, often derived from plants, that bind to carbohydrates. Many lectins are also able to agglutinate cells and several stimulate lymphocytes. Ricin is a toxic lectin that has been used therapeutically by binding the alpha-chain, which is responsible for toxicity, to an antibody molecule to enable site-specific delivery of the toxic effect. In an embodiment of this invention, ricin alpha-chain is conjugated to a chemotactic peptide.

Toxins are poisonous substances produced by plants, animals, and microorganisms that, in sufficient dosage, can be lethal. Diphtheria toxin, a protein produced by *Corynebacterium diphtheriae*, consists of separable alpha and beta subunits. The toxic component can be bound to a chemotactic peptide and used for site-specific delivery to the site of an infection or inflammatory response.

Examples of radioisotopes than can be bound to the chemotactic peptide for therapeutic purposes, used according to the method of the invention, are $^{125}$I, $^{131}$I, $^{90}$Y, $^{67}$Cu, $^{217}$Bi, $^{211}$At, $^{212}$Pb, $^{47}$Sc, $^{186}$Re, $^{188}$Re, $^{105}$Rh, $^{153}$Sm, and $^{109}$Pd.

Anti-microbials useful in the practice of the present invention are substances that inhibit infectious microorganisms, such as bacteria, viruses, fungi, and parasites (Goodman, A. G. et al., 1985 supra), and can be any of those known to persons skilled in the art.

Other therapeutic agents that can be coupled to the chemotactic peptides or specific antibodies used according to the method of the invention are also known, or can be easily ascertained, by those skilled in the art.

Preparations of the imaging chemotactic peptides or therapeutically-conjugated chemotactic peptides for parenteral administration include sterile aqueous or non-aqueous solutions, suspensions, and emulsions. Examples of non-aqueous solvents are propyleneglycol, polyethyleneglycol, vegetable oil, such as olive oil, and injectable organic esters, such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also present, such as, for example, antimicrobials, anti-oxidants, chelating agents, and inert gases. See, generally, *Remington's Pharmaceutical Science*, 16th ed., Mac Eds. 1980.

Preparations of the imaging chemotactic peptides or therapeutically-conjugated chemotactic peptides of the present invention may be administered by any means that achieve their intended purpose. For example, administration may be by parenteral, including subcutaneous, intravenous, intramuscular, intraperitoneal, transdermal, or buccal, routes. Alternatively, or concurrently, oral administration may be employed. A preferred route of administration of the detectably labeled chemotactic peptides for imaging is the intravenous route. The chemotactic peptide can be administered in a single bolus, or by gradual perfusion, which is preferably intravenous, using peristaltic means to accomplish the gradual perfusion.

This invention can be utilized to detect infection or inflammation at a wide variety of body sites including, but not limited to, muscle, vascular walls, abdomen, pelvis, bone, joint, or lung.

This invention can be utilized to diagnose infection by any of a number of microorganisms, or inflammation caused by such infection, or by trauma, autoimmune process, or tumors.

The invention is also useful as a means to evaluate the efficacy of, and responses to, therapeutic treatment of infection or inflammation.

The above disclosure generally describes the present invention. A more complete understanding can be obtained by reference to the following specific examples, which are provided herein for purposes of illustration only and are not intended to be limiting unless otherwise specified.

EXAMPLE 1

Imaging of Focal Sites of Experimental Bacterial Infection

The chemotactic peptide N-formyl-Nle-Leu-Phe-Nle-Tyr-Lys was synthesized using standard solid phase methods well-known in the art (Merrifield, R. B., *J. Am. Chem. Soc.* 15:2149–2154 (1963); Stewart, J. M., and Young, J. D., *Solid Phase Peptide Synthesis*, W. H. Freeman & Company, San Francisco, Calif. (1969)). The epsilon amino group of the C-terminal lysine was modified with DTPA using a cyclic anhydride. The $EC_{50}$ of the nascent peptide and the DTPA derivative were nearly identical, approximately $10^{-9}M$, indicating that the derivatization with DTPA did not affect the biological activity of the peptide. (Similar results were obtained with all peptides tested.) This result was very surprising, since one would expect that introducing the highly negatively charged DTPA group would markedly alter the properties of such small peptides. The peptide was readily radiolabeled with $^{111}In$.

Six Sprague-Dawley rats were experimentally infected by the injection of $10^8$ viable *E. coli* into their left thighs. Approximately 100 μCi of the labeled peptide (5–10 μg) was injected 24 hours after infection. Serial gamma camera images revealed localization of radioactivity at the site of infection with peak accumulation occurring at 1 hour (target-to-background ratio was about 4.0). By 2 hours, the level of activity had decreased in intensity and by 24 hours, the lesion was barely discernible.

These results establish the utility of this new agent for imaging focal sites of inflammation in an animal model of infection.

EXAMPLE 2

Figure 1:
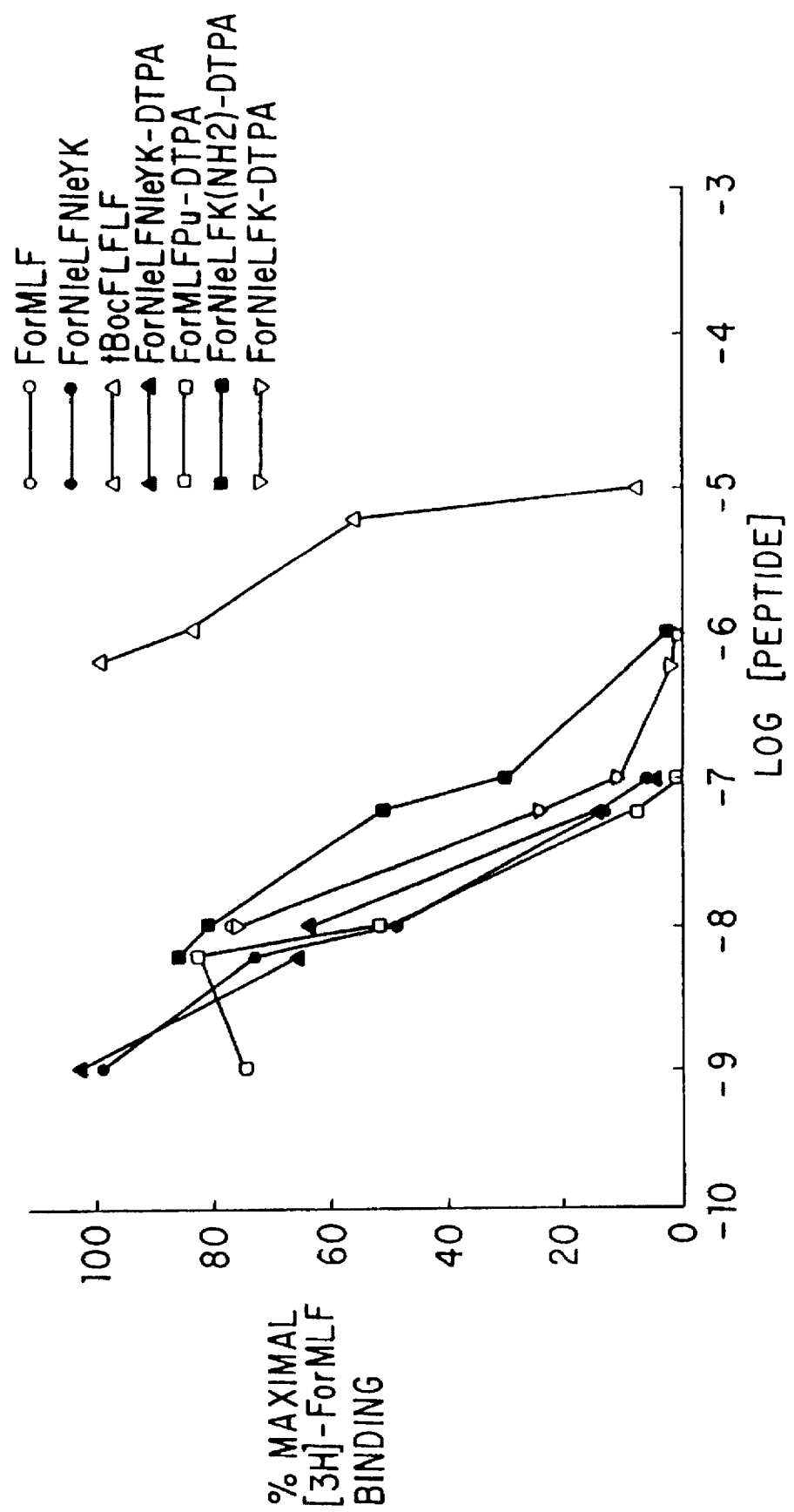
FIG. 1 is a graph demonstrating the results of an assay of the binding of four chemotactic peptides, conjugated with DTPA, to human neutrophils. The assay is a competitive binding assay in which [$^3$H]For-MLF is displaced by increasing concentrations of unlabeled peptide.

Biodistribution of Leukocyte Binding and Bioactivity of Chemotactic Peptides Leukocytic Binding: Four chemotactic peptides conjugated with DTPA were assayed for binding to human neutrophils by a competitive binding assay in which [$^3H$]For-MLF was displaced by increasing concentrations of unlabeled peptide (Babior, B. M. et al., *J. Clin. Invest.* 52:741 (1973)). The results are shown in FIG. 1. Three non-DTPA derivatized peptides were included in the assay for comparison.

Figure 2:
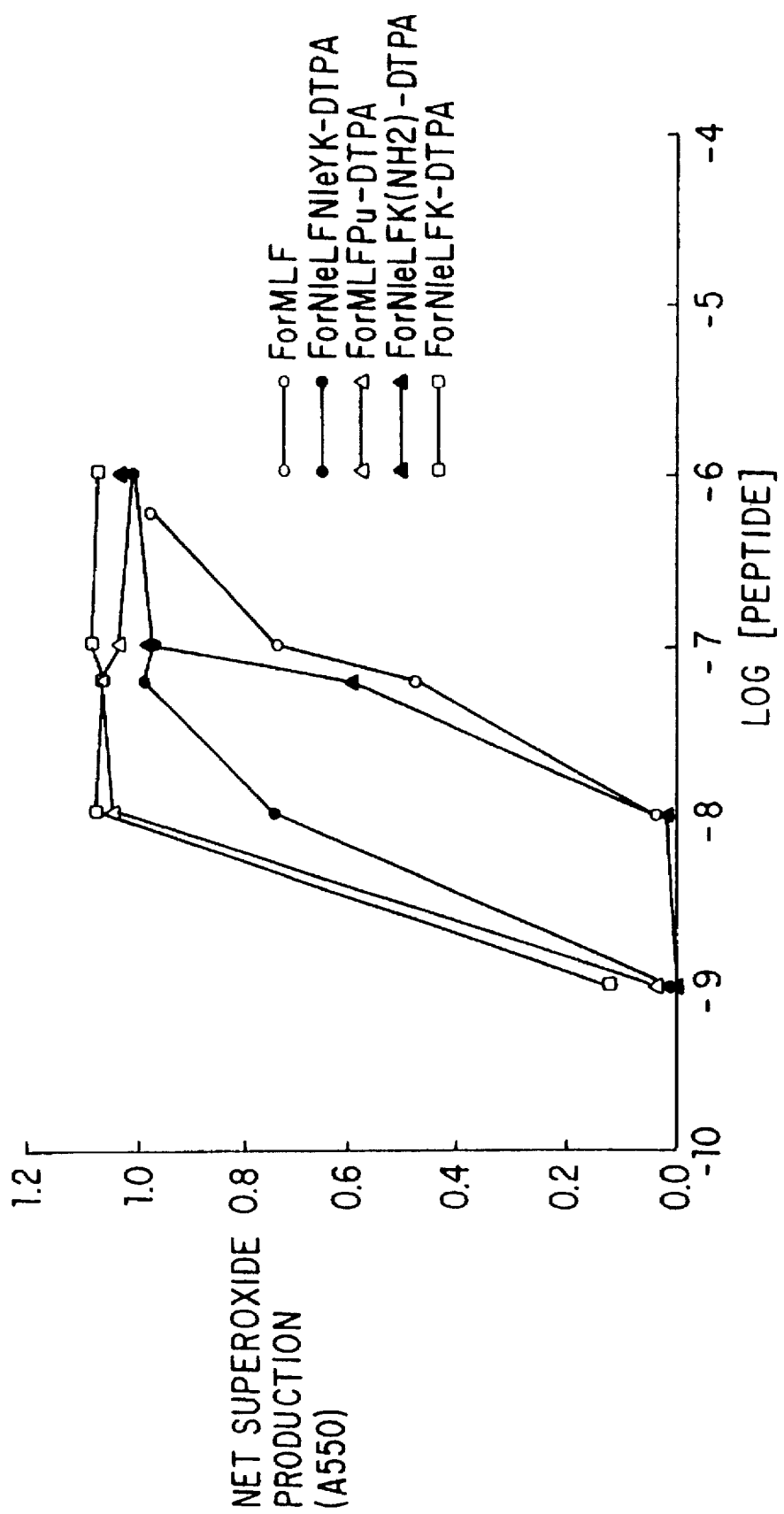
FIG. 2 is a graph demonstrating the results of an assay of four chemotactic peptides, conjugated to DTPA, for stimulation of superoxide production by human neutrophils. MLF was included in the assay for comparison.

SOD Production: Four chemotactic peptides conjugated with DTPA were assayed for stimulation of superoxide production by human neutrophils (Pike, M. C. et al., *Methods in Enzymol.* 162:236 (1988)). These results are shown in FIG. 2. MLF was included in the assay for comparison purposes.

In Vivo Neutropenia: Two chemotactic peptides conjugated with DTPA were administered to rats at a dose approximately 10-fold higher than the standard imaging dose. Peripheral blood was collected (via tail vein) at 5 min pre-injection and at 1, 2, 5, 10, 15, and 30 minutes post-injection. In all animals studied, there was no significant induction of neutropenia.

EXAMPLES 3–5

The following Examples 3–5 show that the peptide isobutyloxycarbonyl-methionyl-leucyl-phenylalanyl-N-diethylenetriaminepentacetyl-lysine (iBoc-MLFK-DTPA) is an antagonist of neutrophil activation by ForMLF that localizes to sites of focal infection in vivo. Localization occurs without altering white blood cell number.

EXAMPLE 3

Isolated human neutrophils ($2.5 \times 10^5$) were preincubated for 10 min with 1 μM iBoc-MLFK-DTPA prior to stimulation with 10 nM ForMLF in the presence of 2.8 μM luminol as the amplifying agent for free radical dependent chemiluminescence. The response was completely inhibited under these assay conditions. A subsequent study demonstrated the inhibition to be dose dependent with an $IC_{50}$ of 0.2 μM.

EXAMPLE 4

The peptide antagonist iBoc-MLFK-DTPA was compared to the peptide agonist formyl-norleucyl-leucyl-phenylalanyl-norleucyl-tyrosyl-lysine-DTPA (ForNleLFNleYK-DTPA) in a rabbit model of focal infection. A focal infection was induced in the hindleg of each rabbit (2–3 kg) using *E. coli*. For procedure, see Example 100 B. After 24 hours, one group of rabbits (n=3) received the antagonist peptide iBoc-MLFK-DTPA while a second group (n=3) received the agonist peptide ForNleLFNleYK-DTPA. The peptides were radiolabeled with $^{111}$Indium to a specific activity of approximately 400 μCi/μg peptide. Each rabbit was anesthetized with Ketamine-Xylazine and 100 μCi or 0.25 μg peptide was injected through the marginal ear vein. The following parameters were measured at 5, 15, 30, and 60 minutes: white blood cell count, whole body images, and, at the 60 minute point, animals were sacrificed for determination of tissue biodistribution. The agonist peptide induced a transient drop in white blood cell number whereas the antagonist did not. The focal infection site was detectable as early as 10 minutes after injection of the agonist or antagonist. Biodistribution showed higher accumulation of the agonist peptide in spleen and liver compared to the antagonist peptide. Both peptides were rapidly accumulated in kidney. Blood levels were slightly higher for the antagonist, which might indicate a longer biological half-life for this peptide. Infected muscle ratios ranged from 4:1 to 7:1 indicating significant uptake into the infected muscle site. The agonist peptide target to background ratio improved over 5 hours, whereas the antagonist peptide ratio was maximal at 1 hour. This may reflect the higher binding affinity of the agonist. The foregoing demonstrates that an antagonist chemotactic peptide is capable of rapidly localizing to a site of focal infection and thus has utility for diagnostic imaging of infected or inflamed sites. In addition, these data indicate the potential use of a peptide antagonist for treating disease involving this specific receptor.

EXAMPLE 5

The unconjugated peptide iBoc-MLFK was evaluated in a neutrophil-endothelial cell adhesion assay. In this assay, neutrophils ($5 \times 10^5$) labeled with 5-carboxyfluorescein diacetate were added into wells of a 48 well dish containing confluent human umbilical vein endothelial cells. The iBoc-MLFK peptide was added at a concentration of 10 μM 10 min prior to stimulation of neutrophils with 30 nM ForMLF. Percent adhesion was determined by washing off unattached neutrophils after an incubation period of 25 minutes. This peptide inhibited adhesion by 66% at this concentration. Subsequently, concentrations between 0.1–3.0 μM were examined. This peptide dose-dependently inhibited neutrophil adhesion to endothelial cells with an $IC_{50}$ of approximately 14 μM. Inhibition of adhesion would reduce the infiltration of leukocytes, such as neutrophils, to a diseased site, thereby limiting the tissue damage associated with inflammation. These data provide further evidence to support the use of peptide antagonists for treating diseases associated with activated leukocytes.

EXAMPLES 6–98

The procedure of Example 5 was repeated for additional CP's within the scope of the present invention. The results are shown in Table I. In the table, MPO is myeloperoxidase assay, a "−" sign means there was no effect at 30 μM, a "+" sign means there was a positive effect at 30 μM, and "N.T." means "Not Tested."

TABLE I

Cell Biology Data

| Example | Sequence | Binding $EC_{50}$, μM | Free Radicals Agonist $EC_{50}$, μM | Free Radicals Antagonist $IC_{50}$, μM | MPO Release $EC_{50}$, μM | Adhesion Agonist $EC_{50}$, μM | Adhesion Antagonist $IC_{50}$, μM |
|---|---|---|---|---|---|---|---|
| 6 | N(N-tosylurea)-MLF | .45 | − | 2.5 | | − | 3.1 |
| 7 | N-adamantylurea-MLF | .87 | − | 1.8 | | − | .68 |
| 8 | Leu—Ala—SHNH—Boc | >100 | − | — | | | — |
| 9 | tBoc—Phe—Leu—Phe | 5.6 | − | 7.1 | | | 5—17 |
| 10 | N(N-isopropylurea)-FLF | .61 | − | 3.1 | | | 6.7 N = 2 |
| 11 | FMOC-Leucine | 7.8 | − | 15.5 | | | 20 |
| 12 | N(vinyl carbamate)-MLF | <10e-12 | .015 | — | | .006 | — |
| 13 | N-propyl-thiourea-MLF | 2.0 | − | 5.6 | | | 12.6 |
| 14 | Phenyl-thiourea-MLF | .4 | − | 5.7 | | | 5.1 |
| 15 | FMOC—MLF | .48 | − | 5.1 | | | 25.8 |
| 16 | tBoc—M(D)LF | >80 | − | — | | | |
| 17 | tBoc—MAc(5)cF | 8.8 | − | 48 | | | 6.5 N = 2 |
| 18 | Isopropylurea-FLFLF—Lys—Lys—SHNH | 15.7 | − | 29.5 | | | |
| 19 | Formyl-MLF—Lys—SHNH | 4e-12 N = 1 | .05 | — | | | |
| 20 | N—N-isopropylurea-FLFLF | .59 | − | 2.6 | | | |
| 21 | Furoic-MLF | 1.8 | − | 17.5 | | | 7.4 N = 1 |
| 22 | Isopropylurea M-Ac5c-F | 13.5 | − | 5.1–50 | | | 20.2 |
| 23 | N-Cinnamoyl-MLF | .04 | .005 | 75.5 | | .004 | — |
| 24 | N—N-Isopropylurea-M—L-Hexahydro-F | .31 | − | 5.6 | | − | 3.7 |
| 25 | Pyrrole-M—L—F | 1.7 | − | 9 | | | 6.2 |
| 26 | Hynic | >100 | >100 | — | | − | N.T. |
| 27 | N-butlyurea-MLF—Lys—SHNH | .11 | .17 | N.T. | | .039 | — |
| 28 | i-propylurea-MLF—Lys—SHNH | 8.5 | >100 | — | 2.2 | 1.5 | >30 |
| 29 | i-proplyurea-MLF—Lys—Asp—SHNH | 4 | >100 | — | .25 | .73 | >30 |
| 30 | N-i-propylurea-MLF-propanediamine-SHNH | 9 | >100 | — | 2.2 | —* | >30* |
| 31 | i-propylurea-MLF-n-propyldiamine-Asp—SHNH | 4.5 | 2 | — | .4 | 1.1 | >30 |
| 32 | i-propylurea-MLF—Lys—SHNH—Boc | .03 | .12 | N.T. | | .013 | |
| 33 | i-propylurea-FLFLF—Lys—SHNH | 2.5 | − | 14.5 | | − | 7.82 |
| 34 | N(N-phenylurea-ML-hexa-F | .02 | − | 1.9 | | + N = 1 | — |
| 35 | Cyclohexylurea-MLF—Lys—SHNH | 1.9 | >100 | — | | 2.2 | N.T. |
| 36 | Formyl-MLF—Lys—SHNH | .17 | .35 | — | | | |
| 37 | iBoc—MLF—SPNH | 0.15–5 | − | 10–30 | | N.T. | >30 |
| 38 | iBoc—MLF—O—SPNH | 0.15–5 | − | 5–6 | .4 pH5 | + (variable) | >30 |
| 39 | iBoc—MLF—S—SPNH | 0.6–22 | − | 3–3.5 | | N.T. | >30 |
| 40 | iBoc—MLF-cleavable conj. | 0.12 | + | >10 | | 1.6 | — |
| 41 | iBoc—MLFK | 20 | − | 10 | | − | 16 |
| 42 | iBoc—MLFK—DTPA | 4.5 | − | | | − | |
| 43 | trimethylacetyl-MLFK | >10 | − | N.T. | | N.T. | — |
| 44 | N-carbamyl-MLFK | >10 | 10 | N.T. | | N.T. | — |
| 45 | For—M(02)—LFK | 1 | + | N.T. | | 0.6 | — |
| 46 | For—M(O)—LFK | 5–10 | + | N.T. | | 2 | — |
| 47 | tBoc—Nle—LFK | — | − | N.T. | | N.T. | — |
| 48 | For—(D)M—LFK | — | − | N.T. | | N.T. | — |
| 49 | iBoc—Nle—LFK | ? — | − | N.T. | | N.T. | — |
| 50 | iBoc—M(O)—LFK | ? — | − | N.T. | | N.T. | — |
| 51 | MeOCO—MLF—COOMe | 2.4 | 3.8 | N.T. | | + | 7.6 |
| 52 | nBoc—MLF—COOMe | 3 | 5.8 | N.T. | | + | 4.5 |
| 53 | iBoc—MLF—COOMe | 7.5 | − | N.T. | | − | 7 |
| 54 | iBoc—MLF—OH | 0.3 | | | | − | 6.3 |
| 55 | CBZ—MLF—COOMe | >10 | − | N.T. | | N.T. | — |
| 56 | tBoc—MLF | 3 | − | 15 | | N.T. | 3.9 |
| 57 | tBoc—NleLF | 3 | − | 15 | | N.T. | 2.5 |
| 58 | tBoc—F(D)LF(D)LF | 5 | N.T. | N.T. | | − | 1.3 |
| 59 | ForMLF | 0.025–0.06 | | | | .007 | |
| 60 | ForMLFK | 0.007 | | | | .014 | |
| 61 | Isopropylurea-MLF A3 Multimer | 1.2 | − | 6.7 N = 1 | | + (variable) | —* |
| 62 | Isopropylurea-MLF A2 Multimer | .4 | 3 | 90 N = 1 | | .333 | — |
| 63 | N-methylurea-MLF | 3.4 | − | 4.8 N = 1 | | − | 6.3 |

TABLE I-continued

Cell Biology Data

| Example | Sequence | Binding $EC_{50}$, μM | Free Radicals Agonist $EC_{50}$, μM | Free Radicals Antagonist $IC_{50}$, μM | MPO Release $EC_{50}$, μM | Adhesion Agonist $EC_{50}$, μM | Adhesion Antagonist $IC_{50}$, μM |
|---|---|---|---|---|---|---|---|
| 64 | N-ethylurea-MLF | 1.2 | – | 9 N = 1 | – | – | 2.5 |
| 65 | N-butylurea-MLF | 0.34 | – | 0.58 | – | + (variable) | — |
| 66 | i-butylurea-MLF | 1.5 | – | 3.5 | N.T. | – | 21.5 |
| 67 | t-butylurea-MLF | 3.3 | – | 1.8 | N.T. | – | 9.4 |
| 68 | N—N-butylthiourea-MLF | .5 | – | 5.0 | – | – | 4.4 |
| 69 | N-butylurea-FLFLF | 0.2 | – | 0.63 | – | – | 2.2 |
| 70 | N-propylurea-MLF | 2.5 | – | 2.8 | N.T. | – | 13 |
| 71 | isopropylurea-MLF | 2.25 | – | 5.4 | N.T. | – | 15.4 |
| 72 | isopropylurea-FLFLF | 0.25 | – | 0.48 | – | – | 1.6 .44 |
| 73 | i-propylurea-MLF—Lys | 16.8 | >100 | 100 N = 1 | – | – | >30 |
| 74 | i-propylurea-MLF-n-propyldiamine acetate | 2.3 | – | 30 N = 1 | – | – | — |
| 75 | cyclohexylurea-MLF | — | – | — | – | N.T. | — |
| 76 | N-phenylurea-MLF | .05/.02 | .15/.15 | —/— | – | .02/.05 | — |
| 77 | N-benzylurea-MLF | .8 | – | 2.6 N = 1 | – | – | 12.6 |
| 78 | N-benzoyl-MLF | 2.4 | – | 32 N = 1 | – | – | 8.8 |
| 79 | n-butyl-amidyl-MLF | .12–7 variable | – | 20 N = 1 | – | – | 9.6 |
| 80 | mesyl-MLF | 24 | – | 70 N = 1 | – | – | >100 |
| 81 | n-butyl-sulfonamidyl-MLF | 1.9 | – | 12 N = 1 | – | – | 1.8 |
| 82 | benzene-sulfonamidyl-MLF | 2.1 | – | 7 N = 1 | – | – | 8.6 N = 2 |
| 83 | ibutyrylamide-M(s=o)LF | 30.3 | – | >100 N = 1 | – | – | >100 |
| 84 | ibutyrylamide-MLF | 2.0 | – | 3.6 | – | – | 6.1 |
| 85 | N—N-4-chlorophenylurea-MLF | 7e-6 N = 1 | <.01 | — | – | <.001 N = 1 | — |
| 86 | P-methoxy-benzylurea-MLF | <.01 N = 1 | .01 | — | – | + | — |
| 87 | P-tolylurea-MLF | <.01 | 7e-4 N = 1 | — | – | .003 | — |
| 88 | M-tolylurea-MLF | .09 | – | 1.2 | – | – | 4.5 |
| 89 | N(N-phenylsulfonylurea)-MLF | 1.5 | – | 9.5 | – | – | >100 N = 2 |
| 90 | 4-carboxy-2-oxo-thiazolidine-MLF | 21.7 | – | 44 | – | – | >100 N = 2 |
| 91 | 4-carboxy-thiazoidine-MLF | 5.5 | – | 26 | – | – | >30 N = 2 |
| 92 | 4-carboxy-2-thioxo—thiazolidine-MLF | 1.6 | 10/>100 | — | – | + N = 1 | — |
| 93 | 1-naphthoyl-amide-MLF | .65 | – | 2.6 | – | – | 11.6 |
| 94 | N(N-isopropylurea-FLFLF-Propanediamine-SPNH | .42 | – | 5.0 | – | – N = 1 | — |
| 95 | N-cinnamoyl-FLFLF | .002 | – | .038 | – | – | 1.5 |
| 96 | N—N-allylurea-MLF | .26 | >100 | 4.9 N = 4 | – | .064 N = 2 | — |
| 97 | N(guanidine)-MLF | 5.9 | – | — | – | Solubility | problems |
| 98 | N-hydrourea-MLF | 1.9 | 2.9 | — | – | .62 N = 1 | — |

*Solubility problems.

EXAMPLE 99

In the following Example, Met-Leu-Phe hydrochloride was synthesized by conventional solution phase methods (Bodansky, M. and Bodansky, A., 1984, "The Practice of Peptide Synthesis", Springer Verlag, N.Y.). The isocyanates were obtained from Aldrich, where available. Isocyanates that were unavailable were prepared by the standard reaction of the desired amine with triphos from Aldrich. All $^1$H NMR spectra were recorded on a Bruker 30 MHz instrument in DMSO $d^6$ or MeOH $d^3$ and are reported relative to TMS internal standard.

N-terminal urea-protected peptides were conveniently prepared in good yield by reaction of the free aminopeptides with the appropriate isocyanate. An example synthesis of N-n-butyl-N'-methionyl-leucyl-phenylalanine-urea is described as follows. 1.0 g Met-Leu-Phe-hydrochloride (2.2 mMol) was suspended in 10 mL dry DMF and 2.2 eq. (0.70 mL, 5.0 mMol) dry triethylamine was added, followed by 1.25 eq (0.31 mL, 2.8 mMol) n-butyl-isocyanate. The reaction mixture was stirred at room temperature for 16 h, after which the DMF was removed on a rotoevaporator. The resulting residue was dissolved in 1 mL methanol, and 15 mL 1N HCl was added with rapid stirring. The resulting white solid (0.81 g, 71%) was filtered, washed with water, and dried overnight in vacuo. FABMS calculated for $C_{25}H_{40}N_4O_5S$ found 509 (M+1). $^1$H NMR (MeOH, $d^6$):δ 8.12 (d, J=8 Hz., 1H), 8.01 (d, J=8 Hz., 1H), 7.21 (m, 5H), 4.62 (m, 1H), 4.30 (m, 1H), 4.25 (m, 1H), 3.17 (m, 4H), 2.45 (t, J=7 Hz, 2H), 1.95 (m, 1H), 1.77 (m, 2H), 1.40 (m, 6H), 0.92 (m, 9H)

EXAMPLE 100

This Example demonstrates that $^{99m}$Tc-labeled chemotactic peptide analogues are effective agents for the external imaging of focal sites of infection.

Four hydrazino nicotinamide (HYNIC) derivatized chemotactic peptide analogues, For-NleLFK-HYNIC (HP1), For-MLFK-HYNIC (HP2), For-MLFNH($CH_2$)$_6$NH-HYNIC (HP3), and For MLF-(D)K-HYNIC (HP4), were synthesized and evaluated for in vitro bioactivity and receptor binding.

Materials and Methods
Peptide Synthesis And Characterization
N-For-Norleucyl-Leucyl-Phenylalanyl-Lysine-$NH_2$,
N-For-Methionyl-Leucyl-Phenylalanyl-Lysine, N-For- Methionyl-Leucyl-Phenylalanyl-diaminohexyl amide, and N-For-Methionyl-Leucyl-Phenylalanyl-D-Lysine-NH2 were synthesized and purified by standard solid phase techniques (Merrifield, R. B., *J. Am. Chem. Soc.* 15:2149–2154 (1963); Stewart, J. M., and Young, J. D., *Solid Phase Peptide Synthesis*, W. H. Freeman & Company, San Francisco, Calif. (1969)) as described by Fischman, A. J., *J. Nucl. Med.* 32:483–491 (1991). All reagents were obtained as the highest available grade from commercial sources. The nicotinyl hydrazine conjugation of these compounds was performed as described below for HP3.

To 186 mg of N-For-Met-Leu-Phe-diaminohexyl amide was added 2 mL of dimethylformamide (DMF) and 60 µL diisopropylethylamine, followed by 154 mg succinamidyl-6-t-Boc-hydrazinopyridine-3-carboxylic acid (Abrams, M. J., et al., *J. Nucl. Med.* 31:2022–2028 (1990)) in 1 mL DMF. The mixture became yellow and the peptide dissolved within a short time. After 2 hours, ether-pet ether was added to the reaction mixture and the upper layer was discarded. Water was added to the oily residue causing a solid to form. The solid was washed with 5% sodium bicarbonate, water, and ethyl acetate yielding a product weighing 183 mg. The t-BOC protecting group was removed by stirring the crude product for 15 minutes at 20° C. with 5 mL of trifluoroacetic acid (TFA) containing 0.1 mL p-cresol. Prolonged treatment with TFA resulted in increased levels of a side product. The TFA was removed by rotary evaporation and ether was added to the residue to precipitate the deprotected peptide. The product was purified by reverse phase HPLC on a 2.5×50 cm Whatman ODS-3 column eluted with a gradient of acetonitrile in 0.1% TFA. Fractions containing the major component were combined and the solvent removed to yield the desired product. The peptides were characterized by UV and mass spectroscopy, as well as by amino acid analysis.

Cell Preparation

Human peripheral blood polymorphonuclear leukocytes (PMN's) were isolated by sedimentation in 3% Dextran (Pharmacia, Nutley, N.J.) followed by gradient centrifugation on Lymphoprep (Organon Teknika, Durham, N.C.). Cell preparations contained >95% PMN's as assessed by light microscopy of Wright stained specimens.

For-MLF Receptor Binding Assay

N-formyl-methionyl-leucyl-phenylalanine (For-MLF), N-formyl-norleucyl-leucyl-phenylalanine (For-NleLF) and N-formyl-norleucyl-leucyl-phenylalanyl-norleucyl-tyrosyl-lysine (For-NleLFNleYK) were obtained from Sigma (St. Louis, Mo.). For-ML[$^3$H]F (60 Ci/mmol) was obtained from New England Nuclear (Boston, Mass.).

Isolated human PMN's (obtained from healthy volunteers), 8×10$^5$, were incubated in phosphate buffered saline containing 1.7 mM KH$_2$PO$_4$, 8.0 mM Na$_2$HPO$_4$, 0.117M NaCl, 0.15 mM CaCl$_2$, 0.5 mM MgCl$_2$, and 1.0 mM PMSF pH 7.4 (incubation buffer) at 24° C. for 45 min in a total volume of 0.15 mL in the presence and absence of varying concentrations of derivatized peptide and 15 nM For-ML[$^3$H]F (Deuel, T. F., et al., *Proc. Natl. Acad. Sci. USA* 78(1):4584–4587 (1981); Fischman, A. J., et al., *J. Nucl. Med.* 32:483–491 (1991); Pike M. C., et al., *Methods Enzymol.* 162:236–245 (1988)). Following incubation, the cells were filtered onto glass fiber discs (Whatman GF/C; Whatman, Inc., Clifton, N.J.) which were then washed with 20 mL of ice cold incubation buffer. The filters were placed in scintillation vials with 10 mL of Safety-Solve (Research Products International Corp., Mt. Prospect, Ill.) and radioactivity was measured by liquid scintillation spectroscopy. Specific binding is defined as total binding minus nonspecific binding. Nonspecific binding is the amount of residual bound radioactivity in the presence of 10 µM unlabeled For-MLF. Nonspecific binding was approximately 10% of total binding.

To determine the effect of radiolabeling with $^{99m}$Tc on binding affinity, isolated human PMN's (2×10$^6$ cells) were incubated in HBSS/BSA at 4° C. for 60 min in the presence and absence of varying concentrations of For-NleLFNleYK or the corresponding unlabeled peptide and a fixed amount of the $^{99m}$Tc-labeled peptide, in a total volume of 0.15 mL. Following incubation, a well mixed aliquot (0.1 mL) of the cell suspension was layered over 0.2 mL of HBSS/BSA:Lymphoprep (1:1) in a 0.4 mL microcentrifuge tube and the contents centrifuged for 4 minutes at 15,000 rpm (Microfuge E, Beckman, Columbia, Md.). The tubes were frozen in liquid nitrogen and the cell pellets isolated. Radioactivity was measured by gamma counting. Nonspecific binding is the amount of residual bound radioactivity in the presence of 5 µM unlabeled For-NleLFNleYK or the corresponding unlabeled peptide. Nonspecific binding was approximately 10% of total binding.

Assay Of Superoxide Production

Phorbol myristate acetate (PMA) and cytochalasin B were obtained from Sigma (St. Louis, Mo.). Superoxide release was assayed by monitoring the superoxide dismutase-inhibitable reduction of ferricytochrome C using an extinction coefficient of 29.5/mmol/L/cm. Briefly, isolated human neutrophils were incubated with Hank's balanced salt solution (HBSS) (GIBCO, Grand Island, N.Y.). HBSS alone or with increasing concentrations of peptide (HP1, HP2, HP3, HP4, For-NleLF, For-MLF or For-NleLFNleYK) ranging from 1 nM to 1 µM in the presence of 10 µM cytochalasin B plus or minus superoxide dismutase (50 µg/mL) at 37° C. for 10 min. The reduction of ferricytochrome C was measured spectrophotometrically.

$^{99m}$Tc Labeling Of HYNIC Derivatized Chemotactic Peptides $^{99m}$Tc-pertechnetate ($^{99}$Mo/$^{99m}$Tc-generator) and stannousglucoheptonate (Glucoscan) were obtained from New England Nuclear (Boston, Mass.). $^{99m}$Tc-glucoheptonate was used to provide the necessary Tc(V) oxo species for radiolabeling the hydrazinonicotinamide conjugated peptides. To the freeze-dried kit was added approximately 2.5 mL of $^{99m}$Tc pertechnetate in 0.9% NaCl. The final radioactive concentration was 5–10 mCi/mL and radiochemical purity of the product was determined by instant thin-layer silica gel chromatography (ITLC-sg) using both acetone and 0.9% NaCl as mobile phase solvents.

The following procedure was used to radiolabel the chemotactic peptide analogs with $^{99m}$Tc. Approximately 0.2 mg peptide was dissolved in 50 µl dimethylsulfoxide and the solution was diluted to a final concentration of 0.1 mg/mL with 0.1M acetate buffer pH 5.2. One half milliliter of peptide solution was placed in a clean glass vial and 0.5 mL of $^{99m}$Tc-glucoheptonate was added. The mixture was vortexed briefly and allowed to stand at room temperature for 1 hour. Radiochemical purity was determined by ITLC-sg in three solvent systems: acetone, 0.9% NaCl, and acetone:water (9:1).

The $^{99m}$Tc labeled peptide analogs were also analyzed by reverse phase HPLC using two systems. System A employed a Beckman C$_{18}$ reverse phase column (5µ, 4.5×46 mm, Beckman, Columbia, Md.) with the following elution conditions: Solvent A: 5% acetonitrile in 50 mM acetate, pH 5.2; solvent B: 50% acetonitrile in 50 mM acetate, pH 5.2; gradient: 0% B to 100% B over 20 minutes; flow rate 2 mL/minute. System B employed a Vydac C$_{18}$ reverse phase column (300 Å, 5µ, 4.5 mm×25 cm, Vydac) with the following elution conditions: Solvent A: 0.1% trifluoroacetic acid in water; solvent B: 0.1% trifluoroacetic acid in acetonitrile; gradient: 0% B to 100% B over 10 minutes; flow rate 2 mL/minute. UV absorption was monitored with a Milton-Roy/LDC flow-through spectrophotometer and radioactivity was monitored using a Beckman 170 (Beckman, Columbia Md.). The outputs from both detectors were recorded and analysed using a dual channel integrator (Waters Model 746 Data Module, Waters, Marlboro, Mass.).

Maximization Of Specific Activity

To avoid the neutropenic effects associated with pharmacological doses of chemotactic peptide analogs, specific activity of the $^{99m}$Tc-labeled chemotactic peptides was maximized so that for an imaging dose of $^{99m}$Tc, the final mass of administered peptide is well below the known $EC_{50}$ concentration (~20 nM) of activation.

A $^{99m}$Tc generator was eluted five hours after a previous elution in an attempt to minimize the proportion of $^{99}$Tc while maintaining a $^{99m}$Tc eluant >300 mCi. The mass of the Tc and the relative proportion of $^{99}$Tc and $^{99m}$Tc were calculated using generator kinetics equations in conjunction with the known history of the $^{99}$Mo/$^{99m}$Tc generator used. $^{99m}$Tc-glucoheptonate (Tc-GH) was prepared as described above. Approximately 180 μg of the chemotactic peptide, (MW: 720), was dissolved in 50 μL of DMSO and diluted to a final concentration of 100 μg/mL with 0.1M acetate buffer, pH 5.2. Aliquots of the peptide solution were serially diluted with acetate buffer to yield a range of concentrations from 2 to 80 μg/mL. Peptide labelling was initiated by adding 0.5 mL of $^{99m}$Tc-GH to an equal volume of peptide in acetate buffer. The solution was vortexed briefly and incubated at room temperature for 1 hour. The extent of peptide labelling was determined by ITLC-sg using three separate solvent systems; acetone, 0.9% NaCl, and acetone:water (9:1). Specific activity of radiolabeled peptide was calculated using the relation: (%RCY×mCi present)/μMoles of peptide×100).

In-Vivo Studies

Three studies were performed in animals: A) To define the in vivo distribution of the radiolabeled peptide analogs in healthy animals, biodistribution studies were performed with each analog; B) To determine the ability of radiolabeled peptide analogs to localize at focal sites of inflammation, tissue radioactivity measurements were performed in rats with *E. coli* infection; and C) To evaluate the infection imaging properties of the radiolabeled peptides, gamma camera imaging was performed in *E. coli* infected rabbits.

A. Biodistribution In Normal Rats

Groups of twenty-four normal male Sprague-Dawley rats weighing approximately 150 g (Charles River Breeding Laboratories, Burlington Mass.) were injected with approximately 5 μCi of each $^{99m}$Tc labeled peptide to determine the biodistribution at 5, 30, 60, and 120 minutes (each peptide was evaluated in 6 animals at each time point). Samples of blood, heart, lung, liver, spleen, stomach, kidney, GI tract, skeletal muscle, testes, and bone were weighed and radioactivity was measured with a well type gamma counter (LKB model #1282, Wallac Oy, Finland). To correct for radioactive decay, aliquots of the injected doses were counted simultaneously. The results were expressed as percent injected dose per gram.

B. Studies With Infected Rats

A single clinical isolate of *E. coli* was employed to produce focal infection. The bacteria were incubated overnight on trypticase soy agar plates at 37° C. and individual colonies were diluted with sterile 0.9% NaCl to produce a turbid suspension containing approximately $2\times10^9$ organisms/mL. Male Sprague-Dawley rats, weighing approximately 150 grams (Charles River Breeding Laboratories, Burlington Mass.) were anesthetized with ketamine and injected intramuscularly in their left posterior thigh with 0.1 mL of a suspension containing approximately $2\times10^8$ organisms.

Twenty-four hours after bacterial inoculation, animals with gross swelling of the infected thigh were injected with approximately 5 μCi (3 pMoles) of $^{99m}$Tc labeled peptide via the lateral tail vein. At 30 and 120 minutes post injection, groups of five animals were sacrificed by cervical dislocation. Tissue sampling, radioactivity measurements, and calculation of results were performed as described above.

C. Imaging Infected Rabbits

In order to determine the feasibility of using radiolabeled chemotactic peptides for infection localization in animals that are sensitive to the neutropenic effects of these agents, imaging studies were performed in rabbits with focal *E. coli* infections. High specific activity $^{99m}$Tc-labeled chemotactic peptide was used in these studies. Six male New Zealand white rabbits weighing 2–3 kg were anesthetized with ketamine and xylazine (15.0 and 1.5 mg/kg) and injected in the left posterior thigh muscle with a 1.0 mL suspension of approximately $2\times10^9$ *E. coli*. Twenty-four hours after inoculation, rabbits with gross swelling in the infected thigh were injected via the lateral ear vein with 600–1000 μCi of HPLC purified $^{99m}$Tc-labeled-HP2 (specific activity >10,000 mCi/μMole, separated from unlabeled peptide by HPLC as described above). The animals were anesthetized with ketamine and xylazine (15.0 and 1.5 mg/kg) and serial scintigrams were acquired at 0 to 3 hours and 16 to 17 hours post injection using a large field of view gamma camera (Technicare Omega 500, Solon, Ohio) equipped with a high resolution parallel hole collimator and interfaced to a dedicated computer (Technicare 560, Solon, Ohio). Images were recorded for a preset time of 5 minutes/view with a 15% window centered to include the 140 KeV photopeak of $^{99m}$Tc. To characterize the localization of labeled peptide, region-of-interest (ROI) analysis was performed, comparing the infected thigh to the contralateral normal thigh muscle as a function of time.

After acquiring the final images, the animals were sacrificed by pentobarbital overdose and samples of blood, heart, lung, liver, spleen, kidney, stomach, intestine, testes, bone, marrow, normal skeletal muscle, infected skeletal muscle, and pus were weighed and radioactivity was measured as described above. To correct for radioactive decay, aliquots of the injected doses were counted simultaneously. The results were expressed as percent injected dose per gram. To determine the amount of cell bound activity in circulation, blood was centrifuged and cells and plasma separated. The cells were washed with 0.9% NaCl and the residual radioactivity in the cells and supernatant measured. To determine the amount of cell bound activity at the site of infection, the pus was washed twice using 0.9% NaCl and the residual radioactivity in the cellular and soluble fractions was measured.

Statistical Methods

The results of the imaging and biodistribution studies were evaluated by analysis of variance (ANOVA) with a linear model in which organ and time were the classification variables; %ID/g or %ID/organ=Organ+Time +Organ× Time. Post-hoc comparison of peptide concentration was performed by Duncan's new multiple range test (Duncan, D. B., *Biometrics* 11:1–42 (1955)). The first subscript of each F value is the number of degrees of freedom for the first classification variable (n−1), the second classification variable (m−1), or the interaction (n−1)×(m−1). The second subscript is the number of residual degrees of freedom (Total number of observations −n×m). All results are expressed as mean ± SEM.

RESULTS

Peptide Synthesis

All four HYNIC derivatized chemotactic peptide analogs were prepared in good yield and purity. UV analysis showed maximum absorption at 268 and 315 nm. characteristic of the HYNIC group, for all 4 peptides. Mass spectroscopy and amino acid analysis were found to be in agreement with the expected conjugated peptide products.

Biological Activity Of Chemotactic Peptide Analogs

Figure 3:
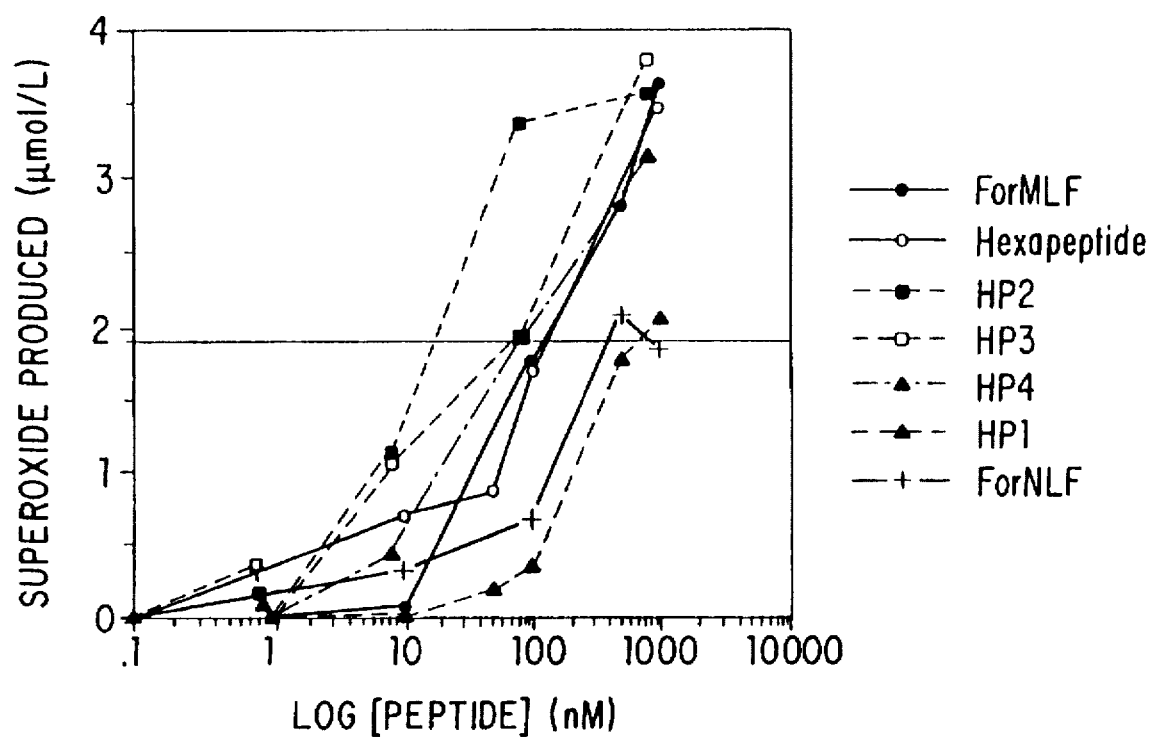
FIG. 3 Superoxide production by chemotactic peptide analogs. Human PMN's were incubated with HBSS alone or the indicated concentration of peptide for 10 min at 37° C., following which the reduction of ferricytochrome was measured.

The results of the superoxide production assay are shown in FIG. 3. The concentrations of peptides that produced 50% of a maximal response ($EC_{50}$) are given in Table II. Peptides HP2, HP3, and HP4 had potencies that were equal to or greater than For-MLF (100 nM). The potency of HP1 was at least an order of magnitude lower. Hence, the order of potency for superoxide production was HP2>HP3>HP4>>HP1.

TABLE II $EC_{50}$'s For Superoxide Production and Binding Affinity of Chemotactic Peptide Analogs

| Peptide | Superoxide Production nM | Binding Affinity nM |
| --- | --- | --- |
| HP1 | 500 | 40 |
| HP2 | 12 | 0.18 |
| HP3 | 40 | 0.12 |
| HP4 | 60 | 0.35 |
| For-MLF | 100 | 20 |
| For-NleLF | 320 | 300 |
| For-NleLFNleYK | 100 | 1 |

The efficacy of the peptides, defined as the maximal amount of superoxide anion produced, was similar for all peptides tested and ranged from 2.07 to 3.80 mol $O_2^-$ produced/$10^6$ cells/10 min. The efficacy of all the peptides was less than that of phorbol myristate acetate (PMA), an unrelated activator of the PMN oxidative burst, which yields maximal response of 22.9 nmol $O_2^-$ produced/$10^6$ cells/10 min at a concentration of 0.1 µM.

Binding of Chemotactic Peptide Analogs to Chemoattractant Receptor

FIG. 4 shows that the HYNIC derivatized chemotactic peptide analogs inhibit binding of For-ML[$^3$H]F to intact human PMN's with an order of potency similar to that for production of superoxide anion. The concentrations of peptide required to produce a 50% inhibition of For-ML[$^3$H]F binding to human PMN's ($EC_{50}$) are given in Table II. Peptides HP2, HP3, and HP4 had $EC_{50}$ values similar to that of the hexapeptide For-NleLFNleYK. The affinity of HP1 for the chemoattractant receptor, while approximately 100-fold lower than the other HYNIC derivatized peptides in this series, was only a factor of 2 lower in potency than For-MLF. The tripeptide For-NleLF had over 100-fold lower potency than both the hexapeptide and For-MLF. Hence, the order of affinity for the chemoattractant receptor was HP3>HP2>HP4>>HP1. The $EC_{50}$ for $^{99m}$Tc-HP2 was <10 nM.

To determine the effect of $^{99m}$Tc labeling on receptor binding, the ability of unlabeled HYNIC-peptide to displace $^{99m}$Tc labeled peptide was evaluated using the assay conditions described above. The results of these experiments demonstrate that the concentration of unlabeled peptide required to displace 50% of the neutrophil binding of the $^{99m}$Tc labeled peptide is approximately 10 fold higher than when For-ML[$^3$H]F is used as the tracer. This increase in binding avidity could be explained if the radiolabeled species contains more than one peptide unit per Tc-glucoheptonate and binding is cooperative.

Radiolabeling With $^{99m}$Tc

The Rf values for $^{99m}$Tc labeled peptide and $^{99m}$Tc-glucoheptonate on instant thin layer chromatography-silica gel strips in the solvent systems used to monitor radiolabeling were: 0.9% NaCl—$^{99m}$Tc-peptide=0.0, $^{99m}$Tc-glucoheptonate=1.0; acetone—$^{99m}$Tc-peptide=1.0, $^{99m}$Tc-glucoheptonate=0.0; and acetone: water (9:1)—$^{99m}$Tc-peptide=1.0, $^{99m}$Tc-glucoheptonate=0.0. The third system minimized peak trailing, yielding sharper $^{99m}$Tc-peptide bands, compared with acetone alone. For all $^{99m}$Tc-peptide preparations ITLC demonstrated that >90% of the radioactivity was associated with the peptide, after 1 hour of incubation. Analysis of the labeled peptides using HPLC system A demonstrated major radioactive peaks for $^{99m}$Tc-glucoheptonate, $^{99m}$Tc-HP1, $^{99m}$Tc-HP2, $^{99m}$Tc-HP3, and $^{99m}$Tc-HP4 with retention times of 0.3–0.5, 14.37, 11.25, 15.11, and 12.96 minutes, respectively.

Maximization of Specific Activity

The $^{99}$Mo/$^{99m}$Tc generator elution yielded a total activity of 456 mCi. The total amount of Tc was 3.4 nMoles, with a $^{99}$Tc to $^{99m}$Tc ratio of 1.53:1 and the specific activity of the $^{99m}$Tc was calculated to be 134,000 mCi/micromole. $^{99m}$Tc-glucoheptonate (Tc-GH) was prepared as described above; final radioactive concentration >150 mCi/mL at the time of preparation. Radiochemical purity of $^{99m}$Tc-GH was determined to be >95% by instant thin-layer chromatography using both acetone and 0.9% NaCl.

The pharmacological potency of the chemotactic peptide agonist analogs requires high specific activity radiolabeling to reduce the absolute amount of peptide present in the injected solution. Ideally, this level of specific activity should be achievable without the need for purification. FIG. 5 summarizes the effect of peptide concentration on labeling yield. From these data, it is clear that the final peptide concentration of the reaction mixture has a significant influence on radiochemical yield; at peptide concentrations below 10 µg/mL poor labeling yields are obtained. When the results are expressed relative to the peptide-to-Tc molar ratio in the reaction mixture, it is apparent that as this ratio increases, % radiochemical yield increases and specific activity decreases.

Using this procedure it is possible to achieve specific activities of >10,000 mCi/Mole; however, the radiochemical yield decreases substantially below peptide concentrations of 10 µg/mL. At peptide concentrations of <10 µg/mL a purification step to remove unbound $^{99m}$Tc is required. Removal of unreacted $^{99m}$Tc glucoheptonate and $^{99m}$TcO$_4^-$ can be achieved with reverse-phase Sep-Paks. A further increase in specific activity can be obtained by removing unreacted peptide by HPLC (using System B). Since the peaks corresponding to $^{99m}$Tc labeled peptide, unlabeled peptide, and $^{99m}$Tc-glucoheptonate are well resolved with this HPLC system, carrier-free radiolabeled peptide can be isolated. Under these circumstances, the specific activity of the radiolabeled peptide is limited only by the specific activity of the eluate from the $^{99m}$Tc generator.

Biodistribution of $^{99m}$Tc Chemotactic Peptides in Normal Rats

The biodistributions of the four $^{99m}$Tc labeled chemotactic peptide analogs are shown in Table III. In all in vivo experiments, the animals tolerated intravenous administration of the radiolabeled chemotactic peptide analogs without apparent ill effects. With the exception of kidney, stomach, and the GI tract, the tissue concentrations of all peptides decreased with time.

ANOVA demonstrated a significant main effect of peptide ($F_{0,63}$=431.00, p<0.0001) and a significant peptide by time interaction ($F_{9,63}$=4.64, p<0.0001). In this organ, the main effect of time was not significant. The order of concentra-

TABLE III

Biodistribution of $^{99m}$Tc Labeled Chemotactic Peptide Analogs. Percent Injected Dose/Gram (Mean ± SEM)

| Organ | Time (min.) | HP1 | HP2 | HP3 | HP4 |
|---|---|---|---|---|---|
| Blood | 5 | 1.17 ± 0.070 | 1.18 ± 0.056 | 1.01 ± 0.056 | 0.78 ± 0.046 |
| | 30 | 0.82 ± 0.019 | 0.67 ± 0.036 | 0.55 ± 0.017 | 0.48 ± 0.052 |
| | 60 | 0.67 ± 0.016 | 0.57 ± 0.033 | 0.47 ± 0.035 | 0.36 ± 0.012 |
| | 120 | 0.52 ± 0.010 | 0.48 ± 0.015 | 0.39 ± 0.015 | 0.31 ± 0.010 |
| Heart | 5 | 0.75 ± 0.045 | 0.50 ± 0.019 | 0.72 ± 0.089 | 0.42 ± 0.027 |
| | 30 | 0.50 ± 0.010 | 0.32 ± 0.016 | 0.27 ± 0.021 | 0.22 ± 0.024 |
| | 60 | 0.40 ± 0.012 | 0.28 ± 0.018 | 0.29 ± 0.026 | 0.20 ± 0.013 |
| | 120 | 0.37 ± 0.028 | 0.26 ± 0.013 | 0.25 ± 0.024 | 0.16 ± 0.012 |
| Lung | 5 | 1.54 ± 0.122 | 0.85 ± 0.043 | 10.65 ± 1.473 | 1.11 ± 0.099 |
| | 30 | 0.63 ± 0.043 | 0.78 ± 0.032 | 8.45 ± 0.818 | 0.61 ± 0.071 |
| | 60 | 0.64 ± 0.039 | 0.46 ± 0.030 | 5.10 ± 0.449 | 0.49 ± 0.026 |
| | 120 | 0.46 ± 0.026 | 0.50 ± 0.025 | 2.44 ± 0.435 | 0.37 ± 0.027 |
| Liver | 5 | 0.76 ± 0.056 | 0.99 ± 0.023 | 5.72 ± 0.467 | 0.74 ± 0.091 |
| | 30 | 0.53 ± 0.012 | 0.62 ± 0.019 | 4.81 ± 0.205 | 0.52 ± 0.022 |
| | 60 | 0.45 ± 0.012 | 0.50 ± 0.022 | 4.60 ± 0.101 | 0.51 ± 0.010 |
| | 120 | 0.43 ± 0.016 | 0.58 ± 0.026 | 4.75 ± 0.175 | 0.46 ± 0.016 |
| Spleen | 5 | 0.34 ± 0.014 | 0.35 ± 0.023 | 2.27 ± 0.281 | 0.35 ± 0.041 |
| | 30 | 0.30 ± 0.012 | 0.39 ± 0.045 | 2.28 ± 0.231 | 0.27 ± 0.017 |
| | 60 | 0.26 ± 0.006 | 0.25 ± 0.013 | 3.11 ± 0.191 | 0.32 ± 0.017 |
| | 120 | 0.25 ± 0.007 | 0.29 ± 0.020 | 3.01 ± 0.220 | 0.27 ± 0.009 |
| Kidney | 5 | 3.08 ± 0.092 | 3.30 ± 0.173 | 1.90 ± 0.199 | 3.67 ± 0.436 |
| | 30 | 5.13 ± 0.282 | 4.82 ± 0.246 | 1.68 ± 0.064 | 5.22 ± 0.139 |
| | 60 | 5.16 ± 0.115 | 4.36 ± 0.213 | 1.63 ± 0.057 | 5.36 ± 0.178 |
| | 120 | 5.68 ± 0.143 | 4.17 ± 0.121 | 1.60 ± 0.030 | 4.74 ± 0.201 |
| Stomach | 5 | 0.17 ± 0.024 | 0.10 ± 0.004 | 0.38 ± 0.053 | 0.19 ± 0.011 |
| | 30 | 0.12 ± 0.012 | 0.15 ± 0.010 | 0.56 ± 0.029 | 0.09 ± 0.023 |
| | 60 | 0.15 ± 0.013 | 0.10 ± 0.005 | 0.51 ± 0.034 | 0.15 ± 0.017 |
| | 120 | 0.16 ± 0.015 | 0.11 ± 0.011 | 0.39 ± 0.008 | 0.15 ± 0.012 |
| GI Tract | 5 | 0.20 ± 0.013 | 0.25 ± 0.012 | 0.33 ± 0.038 | 0.16 ± 0.005 |
| | 30 | 0.32 ± 0.026 | 0.64 ± 0.074 | 0.64 ± 0.046 | 0.32 ± 0.039 |
| | 60 | 0.23 ± 0.020 | 0.64 ± 0.089 | 0.70 ± 0.050 | 0.39 ± 0.030 |
| | 120 | 0.32 ± 0.028 | 0.72 ± 0.055 | 0.81 ± 0.047 | 0.41 ± 0.035 |
| Testes | 5 | 0.15 ± 0.010 | 0.12 ± 0.008 | 0.12 ± 0.011 | 0.19 ± 0.006 |
| | 30 | 0.14 ± 0.005 | 0.11 ± 0.003 | 0.11 ± 0.006 | 0.14 ± 0.015 |
| | 60 | 0.13 ± 0.005 | 0.10 ± 0.006 | 0.11 ± 0.004 | 0.13 ± 0.008 |
| | 120 | 0.14 ± 0.003 | 0.10 ± 0.003 | 0.10 ± 0.005 | 0.11 ± 0.004 |
| Muscle | 5 | 0.32 ± 0.013 | 0.25 ± 0.020 | 0.23 ± 0.015 | 0.27 ± 0.017 |
| | 30 | 0.22 ± 0.004 | 0.17 ± 0.018 | 0.10 ± 0.005 | 0.17 ± 0.013 |
| | 60 | 0.19 ± 0.008 | 0.14 ± 0.016 | 0.12 ± 0.012 | 0.15 ± 0.009 |
| | 120 | 0.20 ± 0.012 | 0.15 ± 0.014 | 0.10 ± 0.007 | 0.12 ± 0.006 |
| Bone | 5 | 0.55 ± 0.026 | 0.39 ± 0.011 | 0.39 ± 0.023 | 0.37 ± 0.038 |
| | 30 | 0.41 ± 0.009 | 0.32 ± 0.013 | 0.26 ± 0.017 | 0.37 ± 0.019 |
| | 60 | 0.33 ± 0.007 | 0.30 ± 0.020 | 0.28 ± 0.023 | 0.34 ± 0.009 |
| | 120 | 0.32 ± 0.011 | 0.28 ± 0.012 | 0.24 ± 0.017 | 0.28 ± 0.009 |

In blood, ANOVA demonstrated significant main effects of peptides ($F_{3,70}$=56.79, p<0.0001) and time ($F_{3,70}$=252.01, p<0.0001); however, the peptide by time interaction was not significant. The order of concentrations of the peptides in blood was: HP1>HP2>HP3>HP4 (p<0.01). In cardiac tissue, ANOVA showed significant main effects of peptide ($F_{3,64}$=44.36, p<0.0001) and time ($F_{3,64}$=98.06, p<0.0001), and a significant peptide by time interaction ($F_{9,64}$=36.9, p<0.0001). In lung, ANOVA demonstrated significant main effects of peptide ($F_{3,6570}$=183.25, p<0.0001) and time ($F_{3,65}$=24.56, p<0.0001), and a significant peptide by time interaction ($F_{9,65}$=13.80, p<0.0001). The order of concentrations of the peptide was: HP3>>HP1=HP4=HP2 (p<0.01). In liver, ANOVA showed significant main effects of peptide ($F_{3,65}$=1000.00, p<0.0001) and time ($F_{3,65}$=12.80, p<0.0001); however, the peptide by time interaction was not significant. As in lung, the order of concentrations of the peptides was: HP3>>HP1=HP4>HP2 (p<0.01). In spleen, tions of the peptides was: HP3>>HP2=HP4=HP1 (p<0.01). In kidney, ANOVA showed significant main effects of peptide ($F_{3,69}$=291.58, p<0.0001) and time ($F_{3,69}$=40.14, p<0.0001), and a significant peptide by time interaction ($F_{9,69}$=10.94, p<0.0001). The order of concentrations of the peptides was: HP4=HP1>HP2>>HP3 (p<0.01). In stomach, ANOVA demonstrated significant main effects of peptide ($F_{3,53}$=202.98, p<0.0001) and time ($F_{3,53}$=3.10, p<0.05), and a significant peptide by time interaction ($F_{9,53}$=5.56, p<0.0001). The order of concentrations of the peptides was: HP3>HP4=HP2 (p<0.01). In the GI tract, ANOVA showed significant main effects of peptide ($F_{3,62}$=66.30, p<0.0001) and time ($F_{3,62}$=36.32, p<0.0001), and a significant peptide by time interaction ($F_{9,62}$=5.56, p<0.005). The order of concentrations of the peptides was: H P3=H P2>HP4=HP1 (p<0.01). In testis, ANOVA demonstrated significant main effects of peptide ($F_{3,67}$=26.97, p<0.0001) and time ($F_{3,67}$=14.94, p<0.0001), and a significant peptide by time interaction ($F_{9,67}$=477, p<0.001). The order of concentrations of the peptides was: HP4=HP1>HP3=HP2 (p<0.01). In skeletal muscle, ANOVA showed significant main effects of peptide ($F_{3,59}$=48.70, p<0.0001) and time ($F_{3,59}$=97.69, p<0.0001); however, peptide by time interaction was not significant. The order of concentrations of the peptides was: HP1>HP2=HP4>HP3 (p<0.01). In bone, ANOVA demonstrated significant main effects of peptide ($F_{3,68}$=30.15, p<0.0001) and time ($F_{3,68}$=52.84, p<0.0001), and a significant peptide by time interaction ($F_{3,68}$=5.15, p<0.0001). The order of concentrations of the peptides was: HP1>HP4=HP2=HP3 (p<0.01).

Localization of $^{99m}$Tc Chemotactic Peptides In Infected Rat Muscle

The tissue concentrations (%ID/gram) of the $^{99m}$Tc labeled chemotactic peptide analogs in normal and infected thigh muscle is shown in Table IV.

TABLE IV

Tissue Concentrations of $^{99m}$Tc-Labeled Chemotactic Peptides in Normal and Infected Rat Muscle
(% ID/gram tissue ± SEM)

| Tissue | TIME (min) | PEPTIDE | | | |
|---|---|---|---|---|---|
| | | HP1 | HP2 | HP3 | HP4 |
| Normal | 30 | 0.16 ± 0.009 | 0.11 ± 0.003 | 0.05 ± 0.009 | 0.13 ± 0.007 |
| | 120 | 0.10 ± 0.006 | 0.07 ± 0.004 | 0.05 ± 0.005 | 0.13 ± 0.1025 |
| Infected | 30 | 0.39 ± 0.013 | 0.28 ± 0.013 | 0.11 ± 0.007 | 0.42 ± 0.049 |
| | 120 | 0.21 ± 0.008 | 0.16 ± 0.007 | 0.10 ± 0.004 | 0.32 ± 0.019 |

ANOVA demonstrated significant main effects of peptide ($F_{3,25}$=56.51, p<0.0001) and time ($F_{3,25}$=59.45, p<0.0001) and a significant peptide by time interaction ($F_{3,25}$=6.74, p<0.005). In normal muscle, concentrations of HP1 (P<0.01) and HP2 (p<0.05) decreased with time, while concentrations of HP3 and HP4 remained unchanged. At 30 minutes after injection, the concentration of HP1 in normal muscle was greater (p<0.01) than the other peptides and the concentration of HP2 was greater (p<0.01) than HP3. At 120 minutes, the concentration of HP4 in normal muscle was greater (p<0.01) than HP2 and HP3; and the concentration of HP1 was greater (p<0.01) than HP3.

In infected muscle, the concentrations of HP1 (p<0.01), HP2 (p<0.01), and HP4 (p<0.05) decreased with time and the concentration of HP3 (which had the lowest level of accumulation at both times) remained unchanged. At 30 minutes after injection, the concentrations of HP1 and HP4 were greater (p<0.01) than the concentrations of HP2 and HP3; and the concentration of HP2 was greater (p<0.01) than HP3. At 120 minutes the concentration of HP4 was greater (p<0.01) than HP1, HP2, and HP3; and the concentration of HP1 was greater (p<0.01) than HP3.

The target-to-background (T/B) ratios, (% ID per gram infected muscle/%ID per gram normal muscle), are shown FIG. 6. ANOVA demonstrated a significant main effect of peptide ($F_{3,22}$=5.87, p<0.005). However, the main effect of time and peptide by time interaction were not significant. The T/B ratio for HP4 was significantly greater than for HP2 (p<0.05), HP1 (p<0.01), and HP3 (p<0.01). Thus, HP4 demonstrated not only the highest absolute concentration in infected tissue but also the highest T/B ratios at both times after injection. In contrast, HP3 had both the lowest absolute concentration in infected muscle and the lowest T/B ratio.

Imaging Of Focal Sites Of Infection In Rabbits

In the rabbit, high levels of $^{99m}$Tc-HP4 were detected in the lung, liver, and spleen immediately after injection. Lung activity decreased with time and at 1–3 hours after injection, focal accumulation of radioactivity was observed in the infected thigh. By 4 hours post injection the T/B ratio was ~4:1. At 16 hours after injection (FIG. 7) the average T/B ratio for the whole lesion increased to 10:1 with focal areas of >20:1. In addition some bowel accumulation was noted at later (>4 hours) time points. The percent residual circulating radioactivity that was cell associated at 16 hours post injection was determined to be approximately 25%. In contrast, fractionation of the pus demonstrated that approximately 90% of the radioactivity was associated with WBC's.

The tissue concentrations (%ID/gram) at 17 hours post injection, as determined by direct tissue counting, are summarized in FIG. 8. The highest concentrations were in spleen >lung>liver=kidney (at p<0.01). The T/B ratios, (% ID per gram infected muscle or pus/%ID per gram contralateral normal muscle), are shown in FIG. 9. The mean T/B ratios for pus and infected muscle were 25.78:1 (maximum 48.54:1 and minimum 8.84:1) and 14.17:1 (maximum 25.64:1, minimum 4.78:1), respectively.

Discussion

The foregoing demonstrates that HYNIC derivatized chemotactic peptide analogs can be readily labeled with $^{99m}$Tc at high activity using $^{99m}$Tc-glucoheptonate as the source of the Tc-(V) oxo core. Furthermore, $^{99m}$Tc labeled peptides are effective agents for the external imaging of focal sites of infection in experimental models of deep thigh infection.

Of the four HYNIC peptides synthesized, three (HP2, HP3, and HP4) had $EC_{50}$'s for receptor binding similar to the hexapeptide, For-NleLFNleYK, while HP1 was within a factor of 2 of For-MLF. All HYNIC conjugated peptides had an enhanced affinity for the chemoattractant receptor compared to For-MLF. The order of potency for receptor binding was HP3>HP2>HP4>For-NleLFNleYK>For-MLF>HP1>For-NleLF. Substituting Nle for Met in For-MLF resulted in a 10–15 fold decrease in affinity for receptor binding. However, further derivatization at the C-terminus with -Lys-HYNIC resulted in enhanced receptor binding.

The $EC_{50}$'s for superoxide production of HP2, HP3, and HP4 were enhanced relative to the hexapeptide and For-MLF by 2–8 fold. For-NleLF demonstrated threefold lower potency than For-MLF. In contrast to the effect of enhanced receptor binding of HP1 compared with For-NleLF, the $EC_{50}$'s for superoxide production were increased by a factor of 5 compared with For-MLF and For-NleLFNleYK.

When interpreted in light of the proposed model for peptide receptor interaction, these data suggest that HYNIC derivatization at the fourth amino acid residue may result in conformational perturbations that affect both receptor binding and superoxide generation. The most striking observation was the effect of substitution of Nle for Met at position 2, which resulted in a greater than 15 fold increase over For-MLF and a 300 fold increase over the hexapeptide in the $EC_{50}$ for receptor binding and a greater than 10 fold increase in the $EC_{50}$ for activation. This result is particularly significant, since for previously reported chemotactic peptide analogs, this substitution had minimal effect. The two fold increase in $EC_{50}$ for receptor binding and the 5 fold increase in the $EC_{50}$ for activation produced by substitution of D-Lys for L-Lys at position 4 also support this hypothesis. The substitution of 1,6 diamino hexane for L-Lys at this position resulted in only a slight decrease in the $EC_{50}$ for binding and a 3–4 fold increase in the $EC_{50}$ for activation. Labeling the HYNIC conjugated peptides with $^{99m}$Tc resulted in an apparent increase in affinity. The results of the $^{99m}$Tc-HYNIC-peptide binding assay experiments demonstrate that the concentration of unlabeled peptide required to displace 50% of the neutrophil binding of the $^{99m}$Tc peptide is approximately 210 fold higher than when ForML|$^3$H|F is used as the tracer. This increase in binding avidity could be explained if the radiolabeled species contains more than one peptide unit per Tc-glucoheptonate and binding is cooperative. A similar increase in binding has been reported with tetrameric chemotactic peptide analogs (Kraus, J. L., et al., *Biochem. Biophys. Res. Comm.* 124:945–949 (1984)). These results also demonstrate the robustness of the C-terminus toward derivatization.

These observations suggest that, in addition to being excellent radiopharmaceuticals for infection imaging, HYNIC peptides may also serve as model compounds for further elucidating the molecular interaction that accompanies the binding of For-MLF to its receptor.

In maximizing the specific activity of HYNIC derivatized chemotactic peptide analogs, the focus has primarily been on manipulating the source of radionuclide, the eluate of the $^{99}$Mo/$^{99m}$TC radionuclide generator. A potential problem with obtaining high specific activity $^{99m}$TcO$_4^-$ is the build up of the long lived $^{99}$Tc (ground state, $t_{1/2} \sim 10^5$ years). Since $^{99}$Tc is directly produced as a result of 87% of the decays of $^{99}$Mo and by 100% of the disintegrations of $^{99m}$Tc, there is always some amount of carrier available to compete in the labeling reaction. $^{99m}$Tc labeled chemotactic peptide analogs with specific activities of >10,000 mCi/µMole can be readily prepared, but a Sep-Pak separation of the labeled peptide from other $^{99m}$Tc species is required. If, in addition to optimizing the source of $^{99m}$Tc, the conditions for chromatographic purification of the radiolabeled peptide is also optimized, even higher specific activities can be achieved. With an HPLC system, the peaks corresponding to $^{99m}$Tc labeled peptide, unlabeled peptide, and $^{99m}$Tc-glucoheptonate can be well resolved and carrier-free radiolabeled peptide isolated. Under these circumstances, the specific activity of the radiolabeled peptide is limited only by the specific activity of the $^{99m}$Tc generator. Thus, based on the theoretical specific activity of $^{99m}$Tc, the maximum specific activity of $^{99m}$Tc labeled HYNIC derivatized chemotactic peptide analogs is approximately 500,000 mCi/µMole. Although achieving this level of specific activity in routine practice is unlikely, it should be possible to prepare radiolabeled peptides with specific activities similar to the $^{99m}$Tc-glucoheptonate that is used for labeling. Since $^{99m}$Tc-glucoheptonate with specific activity of >100,000 mCi/µMole can be prepared on a routine basis, peptides at this level of specific activity should be possible if HPLC purification is employed.

Since the HYNIC glucoheptonate ligand can occupy only two sites of the technetium coordination sphere, the labeled product most probably contains additional groups. It is believed that glucoheptonate serves this role by acting as a "coligand." Owing to the low molecular weight of the chemotactic peptides, the coligand used for technetium labeling could have profound effects on the biodistribution of these molecules. To evaluate this possibility, the biodistribution of $^{99m}$Tc labeled HP2 and HP3 radiolabeled using four different coligands—glucarate, glucoheptonate, mannitol, and glucosamine—was measured. The procedure for radiolabeling with the different ligands was identical to the method used with glucoheptonate. In all cases, HPLC analysis of the radiolabeled peptide showed a single peak.

FIG. 10 shows the % injected dose/gram for these four preparations of HP3 in blood, lung, liver, spleen, kidney, and GI-tract at four time points after injection. Although small differences in biodistribution were detected in most tissues, the most prominent differences (p<0.01) were observed in lung (glucarate, glucoheptonate>mannitol>>glucosamine); liver (glucarate, glucoheptonate, mannitol>>glucosamine); kidney (mannitol>glucarate, glucoheptonate, glucosamine); spleen (glucarate>>glucoheptonate, mannitol>>glucosamine); and GI tract (glucarate, glucosamine>>glucoheptonate>>mannitol). Similar results were obtained with HP2.

There have been several attempts at using radiolabeled chemotactic peptides for infection imaging (Fischman, A. J., *J. Nucl. Med.* 32:483–491 (1991); McAfee, J. G., et al., *Semin. Nucl. Med.* 14:83–106 (1984); Thakur, M. L., et al., *Semin. Nucl. Med.* 14:107–117 (1984); Zogbhi, S. S., et al.,*J. Nucl. Med.* 22:P32 (1981)). However, the radiolabeling methods available at the time of these studies yielded agents of relatively low specific activity, requiring pharmacological amounts of peptide for imaging. These doses of peptide were shown to produce profound transient neutropenia in rabbits (O'Flaherty, J. T., et al., *J. Immunol.* 118:1586–1589 (1977) ). With the radiolabeling techniques of the present invention, these potential adverse effects can be totally eliminated. In rabbits, a species that is highly sensitive to the neutropenic effects of chemotactic peptides, HPLC purified $^{99m}$TcHP4 localized at focal sites of *E. coli* infection within the first hour after injection and reached a maximal T/B ratio at 15 hours.

The HYNIC method of radiolabeling provides a unique and efficient means for preparing $^{99m}$Tc labeled peptides and proteins with extremely high specific activities.

At the high specific activities achieved, it should be possible to perform imaging experiments at peptide concentrations that are significantly below the EC$_{50}$ for the neutropenic response. For example, with SEP-PAK purified peptide (~10,000 mCi/µmole), an injected dose of 20 mCi contains approximately 2 nMoles of peptide. In a 70 kg subject, this represents an injected dose of <30 pMoles/kg. Based on studies with Rhesus monkeys, this amount of peptide is far below the dose that induces significant neutropenia. With HPLC purified material, the margin of safety should be increased approximately 10-fold.

EXAMPLE 101

This Example demonstrates that radiolabeled agonist chemotactic peptide analogs are effective agents for imaging sites of inflammation in monkeys. By radiolabeling at high specific activity, the neutropenic effect of these reagents can be avoided.

In vivo biological activity, biodistribution, and inflammation imaging properties of chemotactic peptide analogs were evaluated in non-human primates. In normal Rhesus monkeys, the dose dependence of the neutropenic response was evaluated. A $^{99m}$TC labeled hydrazino nicotinamide (HYNIC) derivatized chemotactic peptide analog was used to study biodistribution and inflammation imaging in monkeys.

The studies in normal animals demonstrated that the peptide induces a clear dose dependent neutropenia in the animals. The decrease in leukocyte number occurs almost immediately after injection and rapidly returns to baseline. Significant effects on differential WBC count, blood pressure, pulse rate, or respiration rate were not detected. At the lowest dose of peptide tested (10 ng/kg), the decrease in neutrophils was minimal. The HYNIC derivatized peptide was prepared in excellent yield and purity, had biological activity similar to the native peptide, and was readily labeled at specific activity of 20,000 mCi/μmole. When ~0.5 mCi (<2.0 ng/kg) of radiolabeled peptide was injected in monkeys with focal sites of sterile inflammation, a pattern of biodistribution similar to radiolabeled WBC's was observed and neutropenia was not detected. At three hours after injection, the site of inflammation was readily apparent with a T/B of ~3:1.

Materials

N-Formyl-methionyl-leucyl-phenylalanine (ForMLF), N-formyl-norleucyl-leucyl-phenylalanyl-norleucyl-tyrosyl-lysine (ForNleLFNleYK), phorbol myristate acetate (PMA), and cytochalasin B were obtained from Sigma (St. Louis, Mo.). ForML|$^3$H|F (60 Ci/mmol) and $^{99m}$Tc ($^{99}$Mo/$^{99m}$Tc-generator) were obtained from New England Nuclear (Boston, Mass.). Hank's balanced salt solution (HBSS) was from GIBCO (Grand Island, N.Y.).

Peptide Synthesis and Characterization

N-Formyl-Methionyl-Leucyl-Phenylalanyl-Lysine and N-Formyl-Norleucyl-Leucyl-Phenylalanyl-Norleucyl-Tyrosyl-Lysyl-DTPA, were synthesized and purified by standard solid phase techniques (Merrifield, R. B. *J. Am. Chem. Soc.* 15: 2149–2154 (1963); Stewart, J. M., et al., *Solid Phase Peptide Synthesis*, W. H. Freeman & Company, San Francisco, Calif. (1969)) as previously described (Fischman, A. J., et al., *J. Nucl. Med.* 32:483–491 (1991)) The nicotinyl hydrazine derivatized chemotactic peptide analog, N-formyl-met-leu-phe-lys-HYNIC, was prepared as described below.

Succinamidyl-6-t-Boc-hydrazinopyridine-3-carboxylic acid (154 mg, mMole) in 1.0 mL of dimethyformamide (DMF) containing 60 μL of diisopropylethylamine was added to a suspension of N-For-Met-Leu-Phe-Lys (186 mg, mMole) in 2 mL of DMF. The peptide dissolved rapidly and after two hours, ether-pet ether was added. The upper layer was discarded and addition of water to the residue caused a solid to form. The solid was washed with 5% sodium bicarbonate, water, and ethyl acetate. The yield of crude product was 183 mg. The protecting group was removed by stirring the crude product for 15 minutes at 20° C. with 5 mL of trifluoroacetic acid (TFA) containing 0.1 mL p-cresol. The TFA was removed by rotary evaporation and ether was added to precipitate the deprotected peptide. The product was purified by reverse phase HPLC on a 2.5×50 cm Whatman ODS-3 column eluted with a gradient of acetonitrile to 0.1% TFA. Fractions containing the major component were combined and the solvent removed to yield the desired product.

The chemical purity of the final product was evaluated by TLC, HPLC, UV spectroscopy, mass spectroscopy, and amino acid analysis. Determinations of the $EC_{50}$'s for binding to the chemoattractant receptor on human PMN's and superoxide generation were performed as described in Pike, M. C., and Snyderman, R., *Methods Enzymol.* 162:236–245 (1988); Pike, M. C., et al., *Blood* 67:909–913 (1986); and Fischman, A. J., et al., *J. Nucl. Med.* 32:483–491 (1991).

Radiolabeling with $^{99m}$Tc

To avoid the neutropenic effects associated with the administration of pharmacologic doses of chemotactic peptide analogs, the HYNIC derivative was radiolabeled with $^{99m}$Tc under conditions that maximize specific activity. By achieving a high specific activity imaging dose of $^{99m}$Tc, the injected mass of peptide was well below the $EC_{50}$ (~20 nM).

A $^{99}$Mo/$^{99m}$Tc generator was eluted five hours after a previous elution to yield a total activity of ~500 mCi. The mass of the Tc and the relative proportion of $^{99}$Tc to $^{99m}$Tc were calculated by the method of Lamson et at. *J. Nucl. Med.* 7:639–641 (1975). In a typical elution, the total amount of Tc was approximately 3 nMoles, the $^{99}$Tc to $^{99m}$Tc ratio was ~1.5:1 and the specific activity of the $^{99m}$Tc>100,000 mCi/μmole. $^{99m}$Tc-glucoheptonate (Tc-GH) was prepared from stannous glucoheptonate (Glucoscan, DuPont) to provide the Tc(V) oxo species for radiolabeling the hydrazinonicotinamide conjugated peptide (Pike, M. C., et al., *Blood* 67:909–913 (1986)). Approximately 2.5 mL of $^{99m}$Tc-pertechnetate in saline was added to the freeze-dried kit and the final concentration of radioactivity was 150 mCi/mL at the time of preparation. The radiochemical purity of the product was determined to be >95% by instant thin-layer silica gel chromatography (ITLC-sg) using both acetone and saline as mobile phase solvents.

Approximately 180 μg of the chemotactic peptide, For-Met-Leu-Phe-NH-$(CH_2)_6$-NH-HYNIC (MW: 720), was dissolved in 50 μL of DMSO and diluted to a final concentration of 10 μg/mL with 0.1N acetate buffer, pH 5.2. One half milliliter of peptide solution was placed in a clean glass vial and 0.5 mL of $^{99m}$Tc-glucoheptonate was added. The mixture was vortexed briefly and allowed to stand at room temperature for one hour. The extent of peptide labeling was monitored by ITLC-sg using three separate solvent systems: acetone, saline, and acetone:water (9:1). The $^{99m}$Tc labeled peptide was purified by reverse phase HPLC on a $C_{18}$ column (5μ, 4.5×46 mm, Beckman, Columbia, Md.) eluted with a binary gradient. The elution conditions were: Solvent A—5% acetonitrile in 50 mM acetate, pH 5.2; Solvent B—50% acetonitrile in 50 mM acetate, pH 5.2; Gradient: 0% to 100% B over 20 minutes; Flow rate 2 mL/minute. The specific activity of the radiolabeled peptide was calculated using the relation: (% recovery×mCi present)/(mMoles of peptide×100).

Animal Models

Four male Rhesus monkeys, weighing ~10 kg each were evaluated with four doses of ForNleLFNleYK-DTPA (10, 000; 1,000; 100; and 10 ng/kg) dissolved in 0.2 mL of non-pyrogenic saline. Each animal was treated with all four doses of peptide with a one week resting period between each dose level. The animals were anesthetized with ketamine/xylazine and serial 0.5 mL venous blood samples were collected over 80 minutes. Each experiment consisted of four injections—vehicle, peptide, peptide, vehicle. Baseline blood samples were drawn at 15 and 5 minutes prior to the first injection and at 0.25, 0.5, 1, 3, 5, 10, and 20 minutes after each injection. Immediately after collecting the 20 minute blood sample, the next injection was made. Blood pressure, pulse, and respiration rate were monitored throughout the experiment. The white blood cell count (CBC), differential white blood cell count, red blood cell count, and packed cell volume were measured on each blood sample. In addition, the animals were monitored for activity and appearance, food consumption, and body weight. A schematic summary of the experimental protocol is shown in FIG. 11.

Two adult female Rhesus monkeys weighing approximately 10 kg were used in the imaging experiments. Since these animals had been used previously in imaging experiments with other radiopharmaceuticals, they had received numerous intramuscular injections in the right posterior thigh during the induction of anesthesia. These injections resulted in a significant degree of sterile inflammation.

Imaging

Under light ketamine anesthesia (5.5 mg/kg), the animals were injected intravenously through a leg vein with approximately 0.5 mCi $^{99m}$-Tc-labeled peptide (<2.0 ng/kg). At 5 min, 30 min, 1 hr, and 19 hrs following injection of radiolabeled peptide, the animals were anesthetized with ketamine/xylazine (15.0 and 1.5 mg/kg) and whole body scintigrams were acquired using a large field of view gamma camera equipped with a parallel hole high resolution low energy collimator interfaced to a dedicated computer system (Technicare Gemini 700, Technicare 560, Solon, Ohio). All images were acquired at a scan rate of 10 cm/min with a 15% window centered on the $^{99m}$Tc photo-peak at 140 KeV. At 5 minutes prior to injection and 1, 3, 5, and 15 minutes after injection 0.5 mL samples of blood were collected and the CBC was measured.

Regions of interest were drawn over: the whole animal, cardiac blood pool, lung, liver, spleen, kidney, intestine, bone, normal muscle, and inflamed muscle; and count densities (CPM/pixel) were calculated. The results were expressed as tissue-to-blood pool, % injected dose/gram (%ID/g) and target to background ratios (inflamed thigh/contralateral thigh).

Statistical Methods

The results of the imaging studies were evaluated statistically by analysis of variance (ANOVA) followed by Duncan's new multiple range test (Duncan, D. B., *Biometrics* 11:1–42 (1955)).

Results

The HYNIC derivatized peptide was prepared in excellent yield and chemical purity. The final product showed single bands on TLC and HPLC. UV analysis showed maximum absorption at 268 and 315 nm. Mass spectroscopy gave a m/z at 671. Amino acid analysis was in agreement with the expected product (Met-1.00, Leu-1.00; Phe-0.97, Lys-1.00). The specific activity of the radiolabeled peptide was >20,000 mCi/μmole after HPLC purification. In vitro assays for binding to the chemoattractant receptor on human PMN's and superoxide generation yielded EC$_{50}$'s of 2.0 and 20 nM, respectively.

FIG. 12 demonstrates that ForNleLFNeYK-DTPA induces a clear dose dependent neutropenic response in monkeys. At the two highest doses of peptide (10,000 and 1,000 ng/kg), the leukocyte count decreased to approximately 40% of control almost immediately after injection and returned to 60 to 80% of control at the time of the second challenge with peptide. After the second injection of peptide, the leukocyte count decreased to 40 to 50% of control. With the highest dose, the leukocyte count returned to 80% of control at the time of the second injection of vehicle and achieved 90% of control at the end of the study—80 minutes after the first injection of vehicle. With the 1,000 ng/kg dose, the leukocyte count returned to 90% of control at the time of the second injection of vehicle and returned to baseline by the end of the study. After the 100 ng/kg dose, the leukocyte count decreased to approximately 70% of control almost immediately after injection and returned to baseline by the time of the second peptide challenge. At the time of the second injection of vehicle, the leukocyte level returned to baseline. With the lowest dose of peptide (10 ng/kg), the decrease in leukocyte was small and returned to baseline within three minutes after each injection of peptide.

None of the animals demonstrated apparent ill effects after injection of any dose of peptide. Significant effects on differential WBC count, blood pressure, pulse rate, or respiration rate were not detected.

FIG. 13 shows representative, anterior, and posterior images of a monkey at 3 and 15 hours after injection of approximately 1.0 mCi of $^{99m}$Tc labeled peptide. In the early image, there were high concentrations of radioactivity in lung, liver, spleen, and bone consistent with binding to white blood cells. High levels of radioactivity also concentrated in the kidneys and bladder. Lower concentrations were detected in muscle, and the GI tract. In addition, the site of inflammation was well visualized at this time (T/B~3:1). At this dose of peptide, there were no significant effects on WBC level.

At the later imaging time, pulmonary activity decreased, but the distribution of radioactivity in the other organs remained relatively constant. At 15 hours after injection, accumulation of radioactivity at the inflammation site decreased markedly. At both imaging times, a similar pattern of biodistribution was observed in the other animal.

Discussion

This Example establishes that, as in the rabbit (O'Flaherty, J. T., et al., *J. Immunol.* 118:1586–1589 (1977)), agonist chemotactic peptides induce significant transient neutropenia in monkeys. At peptide doses of less than 10 ng/kg, however, this effect is not significant. Some minimal margination of activated neutrophils may occur initially, as noted by the decrease in pulmonary activity with time. When a labeled HYNIC derivatized chemotactic peptide was injected in monkeys with mild sterile inflammatory lesions, the pattern of biodistribution closely paralleled that of radiolabeled white blood cells and the foci of inflammation were readily detectable within three hours after injection with target-to-background ratios of ~3:1. By radiolabeling at very high specific activity (>20,000 mCi/μmole), the total mass of peptide in an imaging dose of radiopharmaceutical could be reduced to a level that is below the neutropenic threshold; at 20,000 mCi/μmole, a 0.5 mCi injection in a 10 kg animal corresponds to a peptide dose of <2 ng/kg. Assuming blood volume to be 8% of body weight and the hematocrit to be 50%, this dose of peptide responds to an initial circulating concentration of 60 pM, which is more than two orders of magnitude below the EC$_{50}$ for receptor activation. As expected, this dose of peptide had no effect on peripheral leukocyte levels.

This Example establishes that radiolabeled chemotactic peptide analogs are effective inflammation imaging agents in animals that are sensitive to their neutropenic effects. Similar results were obtained when the infection imaging of characteristics of these peptides were studied in rabbits (Babich, J. W., et al., (submitted for publication)).

Although sites of sterile inflammation were highly conspicuous at 3 hours after injection, target-to-background ratio decreased dramatically by 12 hours after injection. This is in marked distinction from results in rabbits with focal sites of *E. coli* infection, where the T/B ratio was approximately 3:1 at 3 hours after injection and increased to as high as 20:1 at 12 hours. Possible explanations for this difference include differences in lesion intensity and the difference between bacterial infection and sterile inflammation. If future investigations confirm this difference in lesion kinetics, the utility of the reagents could be significantly increased, since differentiation between infection and sterile inflammation may be possible.

EXAMPLE 102

In this Example, the infection localizing properties of $^{99m}$Tc-labeled agonist chemotactic peptides with conventional $^{111}$In-labeled leukocytes in an animal model of acute bacterial infection are compared and contrasted. Rabbits were chosen because of their known sensitivity to the neutropenic effects of chemotactic peptides.

The biodistribution and infection imaging properties of $^{99m}$Tc-labeled Formyl-Methionyl-Leucyl-Phenylalanyl-Lysyl-hydrazininicotinamide ($^{99m}$Tc-HP) were compared with $^{111}$In-labeled leukocytes ($^{111}$In-WBC's) in rabbits with *E. coli* infections. Groups of 6 animals were injected with 1 mCi of $^{99m}$Tc-HP plus 0.05 mCi of $^{111}$In-WBC's and serial scintigrams were acquired from 3 to 6 hours and 18 hours post injection. After acquiring the final images, the animals were sacrificed and the biodistribution was determined.

At all imaging times, the distributions of $^{99m}$Tc-HP and $^{111}$In-WBC's were similar and the sites of infection were well visualized with both radiopharmaceuticals. The target (infected muscle) to background (contralateral normal muscle) ratios (T/B) were: 3.38±0.46, 3.80±0.37, and 10.875±1.44 for $^{99m}$Tc-HP and 1.71±0.04, 1.81±0.26, and 3.79±0.83 for $^{111}$In-WBC's, at 3, 6, and 18 hours post injection, respectively. The average ratio of T/B's ($^{99m}$Tc-HP to $^{111}$In-WBC's) was 2.99±1.88 with no value less than unity. T/B's calculated from direct tissue sampling were significantly higher for $^{99m}$Tc-HP than for $^{111}$In-WBC's (33.6:1 vs. 8.1:1, p<0.01). These differences were primarily due to increased absolute accumulation of $^{99m}$Tc-HP (0.102%I.D./g vs. 0.024%I.D./g, p<0.01) in infected muscle, rather than a difference in accumulation in normal skeletal muscle.

These results indicate that $^{99m}$Tc-HP yields target-to-background ratios greater than or equal to those achievable with $^{111}$In-WBC's most probably as a result of an increase in absolute accumulation at the site of infection.

Materials and Methods

All inorganic salts were obtained from Fisher Scientific Co. ITLC-silica gel chromatographic strips were obtained from Gelman Laboratories (Ann Arbor, Mich.). $^{111}$In-oxine was obtained from Amersham Inc. (Arlington Heights, Ill.). Stannous glucoheptonate kits (Glucoscan) and $^{99}$Mo/$^{99m}$Tc generators were obtained from DuPont radiopharmaceutical division (Billerica, Mass.). All other reagents here obtained as the highest available grade from commercial sources.

Peptide Synthesis

N-For-Methionyl-Leucyl-Phenylalanyl-Lysine was synthesized and purified by standard solid phase techniques. The nicotinyl hydrazine conjugation of thispeptide, N-For-Met-Leu-Phe-(N-epsilon-HYNIC) Lys (HP), was prepared as described by Babich, J. W., et al., *J. Nucl. Med.* 33:910 (1992). The product was purified by reverse phase HPLC on a 2.5×50 cm Whatman ODS-3 column eluted with a gradient of acetonitrile in 0.1% TFA. Fractions containing the major component were combined and the solvent removed to yield the desired product. The peptide was characterized by UV and mass spectroscopy as well as amino acid analysis.

$^{99m}$Tc Labeling of HYNIC Derivatized Chemotactic Peptides $^{99m}$Tc glucoheptonate was used to provide the necessary Tc(V) oxo species for radiolabeling the hydrazinonicotinamide (Abrams, M. J., et al., *J. Nucl. Med.* 31:2022–2028 (1990)) conjugated peptide. To the freeze-dried kit was added approximately 2.5 mL of $^{99m}$Tc-pertechnetate in 0.9% NaCl. The final radioactive concentration was 100 mCi/mL and radiochemical purity of product was determined by instant thin-layer silica gel chromatography (ITLC-sg) using both acetone and 0.9% NaCl as mobile phase solvents.

The following procedure was used to radiolabel the chemotactic peptide analog with $^{99m}$Tc. Five microliters of a 1 mg/mL peptide solution was transferred to a clean glass vial. 500 μL of 0.1M acetate buffer, pH 5.2, was added to the peptide solution followed by 500 μL $^{99m}$Tc-glucoheptonate.

The mixture was vortexed briefly and allowed to stand at room temperature for 1 hour. Radiochemical purity was determined by HPLC using a $C_{18}$-reverse phase column (300 Å, 5 μ, 4.5 mm×25 cm, Vydac) and the following elution conditions; Solvent A: 0.1% trifluoroacetic acid in water; solvent B: 0.1% trifluoroacetic acid in acetonitrile; Gradient: 0% B to 100% B over 10 minutes; Flow rate 2 mL/minute. UV absorption was monitored with a flow through spectrophotometer (Milton-Roy/LDC, Boca Raton, Fla.) and radioactivity was monitored using a radioisotope detector (Beckman 170, Beckman, Columbia, Md.). The outputs from both detectors were recorded and analyzed using a dual channel integrator (Waters Model 746 data module, Waters, Marlboro, Mass.).

Injectable solutions of $^{99m}$Tc-HP were prepared by isolating the $^{99m}$Tc-HP from the unlabeled HP using the HPLC system described above. The peptide solution was heated gently and dried under a stream of $N_2$. The residue was dissolved in isotonic saline for injection. A sample of the injectate was analyzed by HPLC.

$^{111}$In Labeled Leukocytes

Fifty mL of heparinized whole blood, collected from a donor rabbit that was infected as described below was diluted 1:1 with hetastarch (Hespan®, DuPont, Wilmington, Del.). $^{111}$In labeled leukocytes were prepared by the procedure described by McAfee, J. G., et al., *J. Nucl. Med.* 21:1059–1068 (1980) and McAfee, J. G., et al., *Semin. Nucl. Med.* 14:83–106 (1984) with the following modifications. Leukocyte rich plasma (LRP) was isolated by sedimenting the rabbit blood for 45 min. The LRP was centrifuged at 450×g for 5 min and the WBC pellet was resuspended in 10 mL of saline and allowed to stand for 60 min. The supernatant was drawn off and the cells were resuspended in 5 mL of saline. 500 μCi of $^{111}$In-oxine was added dropwise with agitation and the mixture was incubated for 60 min. at 37° C. with intermittent agitation. The cells were allowed to sediment and the pellet was resuspended in platelet poor plasma (PPP), centrifuged at 450×g for 5 min. and resuspended in PPP for injection. Cell labeling efficiency was calculated as the percent of the initial $^{111}$In-oxine activity added to the cell pellet that remained cell bound after one wash with PPP following separation from the labeling media.

Infection Model

Male New Zealand white rabbits weighing 2.2–3.0 kg were used in all studies. *E. coli* from a single clinical isolate were grown overnight on trypticase soy agar plates and individual colonies were diluted with sterile normal saline to produce a turbid suspension containing approximately $1\times10^{11}$ organisms/0.5 mL (determined with a spectrophotometer). A 0.5 mL inoculum of the bacterial suspension was injected deep in the left thigh muscle of the rabbits.

Twenty four hours after inoculation, rabbits with gross swelling in the infected thigh were injected with the radiopharmaceuticals through a lateral ear vein. Six animals were injected with a mixture of 1 mCi $^{99m}$Tc-HP (>5,000 mCi/μMole) and 0.05 mCi of $^{111}$In labeled white blood cells.

Imaging

At 3, 6, and 18 hours after injection of the radiolabeled reagents, the animals were anesthetized with ketamine/xylazine (15.0 and 1.5 mg/kg) and anterior whole body scintigrams were acquired using a large field of view gamma camera equipped with a parallel hole medium energy collimator interfaced to a dedicated computer system (Technicare Gemini 700, Technicare 560, Solon, Ohio). $^{111}$In and $^{99m}$Tc images were acquired simultaneously in dual photon mode with 15% windows centered on photopeaks at 140 KeV for $^{99m}$Tc and 247 KeV for $^{111}$In. At 3 and 6 hours after injection, two sets of images were acquired for a preset time of 5 minutes/view. At 18 hours after injection, the imaging time was extended to 10 minutes per view. Regions of interest were drawn over the area of infection and the contralateral normal muscle (background). The results were expressed as target-to-background ratios (infected thigh/contralateral thigh).

Direct Tissue Sampling

After acquiring the final images, the animals were sacrificed with an overdose of sodium pentobarbital and biodistribution was determined. Samples of blood, heart, lung, liver, spleen, kidney, adrenal, stomach, GI tract, testes, bone, bone marrow, normal muscle, infected muscle, and pus were weighed and radioactivity was measured with a well type gamma counter (LKB model #1282, Wallac Oy, Finland). To correct for radioactive decay and permit calculation of the concentration of radioactivity in each organ as a fraction of the administered dose, aliquots of the injected doses were counted simultaneously. The results were expressed as percent injected dose per gram (%I.D./g), infected to normal muscle ratios, and pus to normal muscle ratios.

To determine the nature of the radioactivity in the circulation and at the site of infection, the blood and pus samples were fractionated by gradient centrifugation on Lymphoprep. The plasma was further fractionated on a column of Sephadex G-100 (1.0×25 cm) eluted with PBS, pH 7.4. The column was calibrated using $^{111}$In-IgG, $^{111}$In-F(ab')$_2$, $^{125}$I-human albumin, and $^{99m}$Tc-DTPA.

Phantom Studies

Phantom studies were performed to calculate the amount of crossover of 174 KeV photons of $^{111}$In into the $^{99m}$Tc window and 140 KeV photons of $^{99m}$Tc into the $^{111}$In window. Briefly, at the time that the animals were injected, samples of $^{111}$In and $^{99m}$Tc in the same ratio as the injectate were thoroughly mixed with 250 mL of saline in standard infusion bags. The phantoms were placed 5 cm apart on the imaging table and images in both windows were acquired. From regions of interest drawn around each bag, crossover factors were calculated and used to correct the $^{99m}$Tc and $^{111}$In images.

Statistical Methods

The results of the imaging and biodistribution studies were evaluated statistically by analysis of variance (ANOVA) followed by Duncan's new multiple range test (Duncan, D. B., *Biometrics* 11:1–42 (1955)). For the imaging data, two-way ANOVA, with a linear model in which "time after injection" and "radiopharmaceutical" ($^{99m}$Tc-HP or $^{111}$In-WBC's) were the classification variables, was employed; T/B=Time+Radiopharmaceutical +Time× Radiopharmaceutical. For the biodistribution data, two way ANOVA, with a linear model in which organ and Radiopharmaceuticals were the classification variables, was employed; %I.D./gram=Organ+Radiopharmaceutical+ Organ×Radiopharmaceutical. In addition, the target to background ratios for $^{111}$In-WBC's vs $^{99m}$Tc-HP were compared by linear regression. All results were expressed as mean ±SEM.

Results

Peptide Synthesis

The hydrazinonicotinamide derivatized chemotactic peptide was prepared in good yield and purity. UV analysis showed maximum absorption at 268 and 315 nm. Mass spectroscopy and amino acid analysis (Met-1.00, Leu-1.00, Phe-0.97, Lys-1.00) were in agreement with the expected conjugated peptide product.

Radiopharmaceuticals

ITLC and HPLC analysis demonstrated that >90% of the radioactivity was associated with peptide after 1 hour of incubation. The specific activity of unpurified $^{99m}$Tc-HP was calculated to be >3,000 mCi/µMole. Using the purification procedure described above the specific activity increased to >10,000 mCi/µMole.

The $^{111}$In-leukocyte labeling method used in these experiments resulted in labeling efficiencies of approximately 70% prior to purification and a final radiochemical purity of >95%.

Phantom Studies

The phantom studies indicated that at 3 hours after injection of the radiopharmaceuticals, 5% of the photons detected in the $^{99m}$Tc window were contributed by $^{111}$In. At 18 hours after injection, 17% of the photons detected in the $^{99m}$Tc window were contributed by $^{111}$In. At both imaging times 2% of the photons detected in the $^{111}$In window were contributed by $^{99m}$Tc. All imaging data were corrected for these spillover effects.

Imaging

FIG. 14 shows representative, crossover corrected, anterior images of a rabbit at 6 and 18 hours after co-injection of $^{99m}$Tc-HP and $^{111}$In-WBC's. At both imaging times, the overall biodistributions of the two radiopharmaceuticals were nearly identical. High concentrations of both agents were detected in the lung, liver, spleen, and kidney. Concentrations of both tracers were lower in muscle and gastrointestinal tract.

From the imaging data, it is apparent that $^{99m}$Tc-HP localizes at sites of infection to a significant extent at both 6 and 18 hours after injection. The T/B ratio for both agents increased significantly with time (p<:0.01). At both imaging times, the T/B ratio for $^{99m}$Tc-HP was significantly greater (p<0.01) than for $^{111}$In-WBC's. The target to background ratios for both radiopharmaceuticals are summarized in FIG. 15. By 6 hours post injection, the T/B $^{99m}$Tc-HP was equivalent to that of $^{111}$In-WBC's at 18 hours post injection. The mean ratio of T/B's ($^{99m}$Tc-HP to $^{111}$In-WBC's) was 2.99±1.88, with no values below unity.

Direct Tissue Sampling

The biodistributions of $^{99m}$Tc-HP and $^{111}$In-labeled WBC's (%LD./g), determined by direct tissue radioactivity measurements at 18 h after injection, are shown in Table V.

TABLE V

Biodistribution Of $^{99m}$Tc And $^{111}$In-WBC's In The Rabbit
(% I.D.)./g Mean ± SEM)

| Organ | $^{99m}$Tc-HP | $^{111}$In-WBC's |
| --- | --- | --- |
| Blood | 0.037 ± 0.003 | 0.127 ± 0.029 |
| Heart | 0.043 ± 0.005 | 0.024 ± 0.004 |
| Lung | 0.192 ± 0.037 | 0.120 ± 0.007 |
| Liver | 0.207 ± 0.013 | 0.148 ± 0.020 |
| Spleen | 0.601 ± 0.025 | 2.080 ± 0.237 |
| Kidney | 0.136 ± 0.021 | 0.086 ± 0.016 |
| Adrenal | 0.103 ± 0.018 | 0.139 ± 0.026 |
| Stomach | 0.050 ± 0.008 | 0.013 ± 0.003 |
| GI Tract | 0.047 ± 0.005 | 0.018 ± 0.004 |
| Testes | 0.018 ± 0.001 | 0.028 ± 0.003 |
| Muscle | 0.003 ± 0.001 | 0.004 ± 0.001 |
| Marrow | 0.159 ± 0.013 | 0.358 ± 0.107 |
| Bone | 0.033 ± 0.004 | 0.039 ± 0.007 |
| Infected muscle | 0.101 ± 0.008 | 0.024 ± 0.002 |
| Pus | 0.188 ± 0.034 | 0.035 ± 0.008 |

At this time, significant differences in the concentration of these two tracers were found in several tissues. The $^{99m}$Tc-labeled chemotactic peptide had a greater accumulation in infected muscle, (p<0.01), pus (p<0.01), heart (p<0.05), liver (p<0.05), stomach (p<0.01), and GI tract (p<:0.01). Higher levels of $^{111}$In-WBC's were found in blood (p<0.05), spleen (p<:0.01), and testes (P<0.01). No significant differences were found in normal skeletal muscle, bone, marrow, lung, adrenal, or kidney.

The results of blood fractionation demonstrated that, at both time points, only ~25% of the circulating $^{99m}$Tc radioactivity was associated with leukocytes, while greater than 85% of the $^{111}$In radioactivity was bound to white cells. For both radionuclides, binding to red blood cells was minimal (<2%). In contrast, fractionation of the pus demonstrated that for both $^{99m}$Tc and $^{111}$In, approximately 90% of the radioactivity was associated with WBC's. Column chromatography of the plasma demonstrated that >95% of the $^{99m}$Tc radioactivity that was not bound to WBC's eluted with an apparent molecular weight of 150,000 (IgG fraction); no radioactivity was detected at the elution position of the free peptide. Radioactivity from the column was greater than 90%.

FIG. 16 shows a plot of the infected muscle to normal muscle ratios for $^{99m}$Tc-HP and $^{111}$In-WBC's determined by direct radioactivity measurements on samples of excised tissues at 18 hours after injection. The mean infected muscle to normal muscle ratios were significantly higher for $^{99m}$Tc-HP compared to $^{111}$In-WBC's (33.6:1 vs.8.1:1, p<0.01). This difference was due to an increase in the absolute accumulation in infected muscle of $^{99m}$Tc-HP (0.102%I.D./g) as compared to $^{111}$In-WBC's (0.024%I.D./g) rather than a difference in accumulation in normal skeletal muscle (0.003 I.D./g vs 0.004% I.D./g for $^{99m}$Tc-HP and $^{111}$In-WBC's, respectively). Regression analysis failed to demonstrated significant correlation between $^{99m}$Tc-HP and $^{111}$In-WBC accumulation ($r^2$=0.076).

The pus to contralateral normal muscle ratios, determined by direct radioactivity measurements at 18 hours after injection are summarized in FIG. 17. The mean pus to normal muscle ratio for $^{99m}$Tc-HP was 61.8±11.05 versus 9.32±2.50 for $^{111}$In-WBC's (p<0.01). The greater accumulation of $^{99m}$Tc-HP in pus (0.188±0.034%I.D./g) as compared to $^{111}$In-WBC's (0.035±0.008%I.D./g) was the major cause of the higher T/B ratio for $^{99m}$Tc-HP.

Discussion

This Example demonstrates that the $^{99m}$Tc-labeled chemotactic peptide is superior to $^{111}$In-WBC's for imaging bacterial infection in the rabbit. The absolute level of accumulation of $^{99m}$Tc-labeled chemotactic peptide (%I.D./gram) in infected muscle and pus was greater than that of $^{111}$In-WBC's. In addition, the target to background ratios are greater for $^{99m}$Tc-HP at all imaging times. By 6 hours post injection, the T/B ratio for $^{99m}$Tc-HP was equivalent to $^{111}$In-WBC's at 18 hours post injection, suggesting that the $^{99m}$Tc-labeled chemotactic peptide may offer a rapid alternative for infection imaging. As the difference in normal muscle accumulation was insignificant, the improved T/B ratios of $^{99m}$Tc-HP over $^{111}$In-WBC's is predominantly due to the greater concentration of $^{99m}$Tc-HP at the site of infection.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of detecting a site of infection or inflammation in an individual which comprises:

a. administering to the individual a diagnostically effective amount of a detectably labeled chemotactic peptide

wherein:

X is an amino-protecting group,

Y is an amino acid residue,

Z is a spacer sequence, n is 0 or 1, and

W is a labeling or attachment substituent of the structure

wherein:

K is an intermediary functional group, v is 0 or 1, and $M^1$ is a diagnostically detectable label; and wherein the chemotactic peptide substantially accumulates at the site of infection or inflammation and does not substantially accumulate at a site that is not infected or inflamed; and b. detecting the chemotactic peptide.

2. A method of detecting a site of infection or inflammation in an individual which comprises:

a. administering to the individual a diagnostically effective amount of a detectably labeled chemotactic peptide

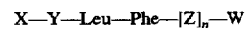

wherein:

X is an amino protecting group,

Y is

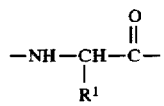

where
$R^1$ is benzyl, alkyl, or —$CH_2$—$CH_2$13 $R^2$—$CH_3$ and

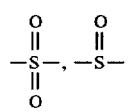

Z is a spacer sequence, n is 0 or 1, and

W is a labeling or attachment substituent of the structure

wherein:

K is an intermediary functional group,
v is 0 or 1, and
$M^1$ is a diagnostically detectable label; and
wherein the chemotactic peptide substantially accumulates at the site of infection or inflammation and does not substantially accumulate at a site that is not infected or inflamed; and b. detecting the chemotactic peptide.

3. The method of claim 1 wherein X is an amino protecting group selected from the group consisting of carbamates, carboxamides, thiocarboxamides, ureas, thioureas and their corresponding cyano guanidine derivatives, sulfonamides, and phosphonamides.

4. The method of claim 1 wherein X is $$R^3-C=R^4$$

where $R^3$ is selected from the group consisting of hydrogen, alkyl, alkenyl, alkynyl, alkoxy, aralkoxy, and amino and $R^4$ is a chalcogen.

5. The method of claim 4 wherein $R^4$ is oxygen or sulfur.

6. The method of claim 2 wherein $R^1$ is —$CH_2$—$CH_2$—$R^2$—$CH_3$.

7. The method of claim 6 wherein the detectably labeled chemotactic peptide is

X—Met—Leu—Phe—$[Z]_v$—W.

8. The method of claim 7 wherein the methionine residue is replaced by 4-aminotetrahydrothiopyran-4-carboxylic acid.

9. The method of claim 7 wherein the leucine residue is replaced by dipropylglycine.

10. The method of claim 7 wherein the leucine residue is replaced by 1-aminocyclohexanecarboxylic acid.

11. The method of claim 7 wherein the phenylalanine residue is replaced by z-dehydrophenylalanine.

12. The method of claim 7 wherein the phenylalanine residue is replaced by 2-aminoindanone-2-carboxylic acid.

13. The method of claim 7 wherein the phenylalanine residue is replaced by anilinoglycine.

14. The method of claim 1 wherein n is 1 and Z is $[R^6]_m$ wherein $R^6$ is an amino acid residue and m is an integer greater than or equal to 1.

15. The method of claim 14 wherein m is 1 and $R^6$ is selected from the group consisting of norleucine, tyrosine, aspartic acid, lysine, leucine, and phenylalanine.

16. The method of claim 14 wherein m is 2 or more and each $R^6$ is independently selected from the group consisting of norleucine, tyrosine, aspartic acid, lysine, leucine, and phenylalanine.

17. The method of claim 1 wherein the detectably labeled chemotactic peptide is selected from the group consisting of N-For-Nle-Leu-Phe-Nle-Tyr-Lys-DTPA
N-For-Met-Leu-Phe-Pu-DTPA
N-For-Nle-Leu-Phe-Lys-DTPA
N-For-Nle-Leu-Phe-Lys($NH_2$)-DTPA
N-For-Met-Leu-Phe-Lys-DTPA
N-For-Met-Leu-Phe-D-Lys ($NH_2$)-DTPA
N-Ac-Nle-Leu-Phe-Lys($NH_2$)-DTPA
N-Carbobenzoxy-Met-Leu-Phe-Methyl Ester
IBOC-L-Methionyl (sulfoxide)-L-Leu-L-Phe-L-lysinamide
IBOC-L-Norleucyl-L-Leu-L-Phe-L-lysinamide
N-For-L-Methionyl (sulfoxide)-L-Leu-L-Phe-DTPA-L-Lys
N-For-L-Methionyl (sulfone)-L-Leu-L-Phe-N-DTPA-L-Lys
N-Isobutylurea-Met-Leu-Phe-carboxylate
Isobutyloxycarbonyl-Met-Leu-Phe-N-DTPA-Lys
N-For-(D)-Met-Leu-Phe-Lys Amide Solvated
t-BOC-Nle-Leu-Phe-Lys Solvated
N-For-Methionyl-Sulfoxide-Leu-Phe-Lys Amide Solvated
N-For-Methionyl-Sulfone-Leu-Phe-Lys Amide Solvated
N-Carbamyl-Met-Leu-Phe-Lys Amide Solvated
N-Trimethylacetyl-Met-Leu-Phe-Lys Amide Solvated
Isobutyloxycarbonyl-Met-Leu-Phe-Lys Amide Solvated
N-For-Nle-Leu-Phe-Nle-Tyr-$N^\epsilon$-DTPA-Lys
Isopropylurea-Met-Leu-Phe-Lys-SHNH-BOC
Isopropylurea-Met-Leu-Phe-n-propyldiamine-Asp-SHNH HBr
Isopropylurea-Met-Leu-Phe-Lys-Asp-SHNH HBr
Isopropylurea-Met-Leu-Phe-Lys-SHNH HBr
N-Phenylurea-Met-Leu-Phe
Isopropylurea-Met-Leu-Phe-Propane diamine-SHNH
N-n-Butyl-thiourea-Met-Leu-Phe
N-n-butylurea-Phe-Leu-Phe-Leu-Phe
N-isopropylurea-Phe-Leu-Phe-Leu-Phe—COOH
iBOC-Met-Leu-Phe—COOH
iBOC-Met-Leu-Phe|amido(propylamido)carboxy|(propyl) carboxy)]-(amido propanol SPNH) ester
N-isobutylurea-Met-Leu-Phe-Carboxylate
N-n-Propyl-urea-Met-Leu-Phe
N-t-Butyl-urea-Met-Leu-Phe
N-n-Butyl-urea-Met-Leu-Phe
iBOC-Met-Leu-Phe-(amido ethoxy ethyl |3-amido]-6-propenal hydrazone)-pyridine
N-iBOC-Met-Leu-Phe-SPNH-thioester
N-isopropylurea-Met-Leu-Phe
N-iBOC-Met-Leu-Phe-Propylene diamine-SPNH
Cyclohexyl-urea-Met-Leu-Phe—COOH
N-n-Butyl carbamate-Met-Leu-Phe-Methyl ester
N-iBOC-Met-Leu-Phe-Methyl ester
N-Methyl carbamate-Met-Leu-Phe-Methyl ester
N-Adamantylurea-Met-Leu-Phe
N-Cinnamoyl-Met-Leu-Phe
P-Tolylurea-Met-Leu-Phe
M-Tolylurea-Met-Leu-Phe
N-Cinnamoyl-Phe-Leu-Phe-Leu-Phe.

18. The method of claim 1 wherein $M^1$ comprises a radioactive isotope.

19. The method of claim 18 wherein $M^1$ is $^{111}$In or $^{99m}$Tc.

20. The method of claim 1 wherein $M^1$ comprises a paramagnetic isotope or a compound that can be imaged by PET.

21. The method of claim 18 wherein the administering is parenteral.

22. The method of claim 20 wherein the administering is parenteral.

23. The method of claim 21 wherein the parenteral administration comprises intradermal, subcutaneous, intramuscular, intraperitoneal, or intravenous injection.

24. The method of claim 22 wherein the parenteral administration comprises intradermal, subcutaneous, intramuscular, intraperitoneal, or intravenous injection.

25. The method of claim 23 wherein the administration is by gradual perfusion.

51

26. The method of claim 24 wherein the administration is by gradual perfusion.

27. The method of claim 25 wherein the gradual perfusion is by the intravenous route using peristaltic means.

28. The method of claim 26 wherein the gradual perfusion is by the intravenous route using peristaltic means.

29. The method of claim 19 wherein the individual is human.

30. The method of claim 1 wherein v is 1 and K is DTPA, EDTA, or HYNIC.

31. The method of claim 30 wherein $M^1$ comprises a radioactive isotope.

32. The method of claim 31 wherein said radioactive isotope is $^{111}$In or $^{99m}$Tc.

33. The method of claim 30 wherein $M^1$ comprises a paramagnetic isotope or a compound that can be imaged by PET.

34. The method of claim 30 wherein K is HYNIC.

35. The method of claim 34 wherein W additionally comprises L, wherein L is an ancillary ligand.

36. The method of claim 35 wherein the ancillary ligand comprises glucoheptonate, tricine, or an additional peptide unit.

37. The method of claim 36 wherein the additional peptide unit is

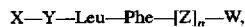
X—Y—Leu—Phe—[Z]$_n$—W, wherein W is a labeling or attachment substituent of the structure

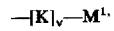
—[K]$_v$—M$^{1}$, wherein K is HYNIC, v is 1, and $M^1$ is a diagnostically detectable label.

38. A method of detecting a site of infection or inflammation in an individual which comprises:

a. administering to the individual a diagnostically effective amount of a detectably labeled chemotactic peptide

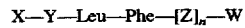
X—Y—Leu—Phe—[Z]$_n$—W wherein:

X is an amino protecting group of the structure $$R^3-\underset{|}{C}=R^4$$

where $R^3$ is selected from the group consisting of hydrogen, alkyl, alkenyl, alkynyl, alkoxy, aralkoxy, and amino and $R^4$ is oxygen or sulfur, Y is Met, Phe, or Nle, Z is a spacer sequence selected from the group consisting of aliphatic diamines of 1 to 6 carbon atoms, [R$^6$]$_m$, and mixtures thereof, wherein R$^6$ is an amino acid residue and m is an integer of from 1 to 3, n is 0 or 1, and W is a labeling or attachment substituent of the structure

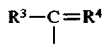
—[K]$_v$—M$^1$ wherein:

K is DTPA, EDTA, or HYNIC, v is 1, and $M^1$ is $^{111}$In or $^{99m}$Tc;

and wherein the chemotactic peptide substantially accumulates at the site of infection or inflammation and

52 does not substantially accumulate at a site that is not infected or inflamed; and b. detecting the chemotactic peptide.

39. The method of claim 38 wherein Y is Met.

40. The method of claim 39 wherein the methionine residue is replaced by 4-aminotetrahydrothiopyran-4-carboxylic acid.

41. The method of claim 39 wherein the leucine residue is replaced by dipropylglycine.

42. The method of claim 39 wherein the leucine residue is replaced by 1-aminocyclohexanecarboxylic acid.

43. The method of claim 39 wherein the phenylalanine residue is replaced by z-dehydrophenylalanine.

44. The method of claim 39 wherein the phenylalanine residue is replaced by 2-aminoindanone-2-carboxylic acid.

45. The method of claim 39 wherein the phenylalanine residue is replaced by anilinoglycine.

46. The method of claim 38 wherein n is 1 and Z is [R$^6$]$_m$.

47. The method of claim 46 wherein m is 1 and R$^6$ is selected from the group consisting of norleucine, tyrosine, aspartic acid, lysine, leucine, and phenylalanine.

48. The method of claim 46 wherein m is 2 and each R$^6$ is independently selected from the group consisting of norleucine, tyrosine, aspartic acid, lysine, leucine, and phenylalanine.

49. The method of claim 46 wherein m is 3 and each R$^6$ is independently selected from the group consisting of norleucine, tyrosine, aspartic acid, lysine, leucine, and phenylalanine.

50. The method of claim 49 wherein K is HYNIC.

51. The method of claim 50 wherein W additionally comprises L, wherein L is an ancillary ligand.

52. The method of claim 51 wherein the ancillary ligand comprises glucoheptonate, tricine, or an additional peptide unit.

53. The method of claim 52 wherein the additional peptide unit is

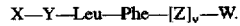
X—Y—Leu—Phe—[Z]$_v$—W.

wherein W is a labeling or attachment substituent of the structure

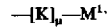
—[K]$_\mu$—M$^{1}$, wherein K is HYNIC, v is 1, and $M^1$ is a diagnostically detectable label.

54. The method of claim 38 wherein the administering is parenteral.

55. The method of claim 54 wherein the parental administration comprises intradermal, subcutaneous, intramuscular, intraperitoneal, or intravenous injection.

56. The method of claim 55 wherein the administration is by gradual perfusion.

57. The method of claim 56 wherein the gradual perfusion is by the intravenous route using peristaltic means.

58. The method of claim 38 wherein the individual is human.

59. A detectably labeled chemotactic peptide

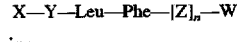
X—Y—Leu—Phe—[Z]$_n$—W wherein:

X is an amino protecting group of the structure $$R^3-\underset{|}{C}=R^4$$

where $R^3$ is selected from the group consisting of hydrogen, alkyl, alkenyl, alkynyl, alkoxy, aralkoxy, and amino and $R^4$ is oxygen or sulfur,

53

Y is an amino acid residue,

Z is a spacer sequence selected from the group consisting of aliphatic diamines of 1 to 6 carbon atoms, $|R^6|_m$, and mixtures thereof, wherein $R^6$ is an amino acid residue and m is an integer greater than or equal to 1, n is 0 or 1, and W is a labeling or attachment substituent of the structure $$-|K|_v-M^1$$

wherein:

K is DTPA, EDTA, or HYNIC, v is 1, and $M^1$ is $^{111}$In or $^{99m}$Tc; and wherein the chemotactic peptide substantially accumulates at the site of infection or inflammation and does not substantially accumulate at a site that is not infected or inflamed.

60. The peptide of claim 59 wherein Y is Met, Phe, or Nle.
61. The method of claim 60 wherein K is HYNIC.
62. The method of claim 61 wherein W additionally comprises L, wherein L is an ancillary ligand.
63. The method of claim 62 wherein the ancillary ligand comprises glucoheptonate, tricine, or an additional peptide unit.
64. The method of claim 63 wherein the additional peptide unit is $$X-Y-Leu-Phe-|Z|_n-W,$$

wherein W is a labeling or attachment substituent of the structure $$-|K|_v-M^{1,}$$

wherein K is HYNIC, v is 1, and $M^1$ is a diagnostically detectable label.

65. A pharmaceutical preparation of the chemotactic peptide of claim 59 suitable for parenteral administration.
66. A chemotactic peptide selected from the group consisting of N-For-Nle-Leu-Phe-Nle-Tyr-Lys-DTPA, N-For-Met-Leu-Phe-Pu-DTPA, N-For-Nle-Leu-Phe-Lys-DTPA, N-For-Nle-Leu-Phe-Lys(NH$_2$)-DTPA, N-For-Met-Leu-Phe-Lys-DTPA, N-For-Met-Leu-Phe-D-Lys (NH$_2$)-DTPA, N-Ac-Nle-Leu-Phe-Lys(NH$_2$)-DTPA, IBOC-L-Methionyl (sulfoxide)-L-Leu-Phe-L-lysinamide, IBOC-L-Norleucyl-L-Leu-L-Phe-L-lysinamide, N-For-L-Methionyl (sulfoxide)-L-Leu-L-Phe-DTPA-L-Lys, N-For-L-Methionyl (sulfone)-L-Leu-L-Phe-N-DTPA-L-Lys, N-Isobutylurea-Met-Leu-Phe-carboxylate, Isobutyloxycarbonyl-Met-Leu-Phe-N-DTPA-Lys, N-For-(D)-Met-Leu-Phe-Lys Amide Solvated, t-BOC-Nle-Leu-Phe-Lys Solvated, N-For-Methionyl-Sulfoxide-Leu-Phe-Lys Amide Solvated, N-For-Methionyl-Sulfone-Leu-Phe-Lys Amide Solvated, N-Carbamyl-Met-Leu-Phe-Lys Amide Solvated, N-Trimethylacetyl-Met-Leu-Phe-Lys Amide Solvated,

54

Isobutyloxycarbonyl-Met-Leu-Phe-Lys Amide Solvated, and

N-For-Nle-Leu-Phe-Nle-Tyr-N$^\epsilon$-DTPA-Lys

N-Adamantylurea-Met-Leu-Phe

N-Cinnamoyl-Met-Leu-Phe

P-Tolylurea-Met-Leu-Phe

M-Tolylurea-Met-Leu-Phe

N-Cinnamoyl-Phe-Leu-Phe-Leu-Phe wherein said chemotactic peptide is labeled with a diagnostically detectable label, and said chemotactic peptide is capable of accumulating at a site of infection or inflammation in an individual and does not substantially accumulate in said site in the absence of infection or inflammation.

67. The peptide of claim 66 wherein the detectable label is a radioactive isotope.
68. The peptide of claim 67 wherein the radioactive isotope is $^{111}$In or $^{99m}$Tc.
69. The peptide of claim 66 wherein the detectable label is a paramagnetic isotope or a compound that can be imaged by PET.
70. A therapeutic composition comprising a chemotactic peptide $$X-Y-Leu-Phe-|Z|_n-|T|_\alpha$$

wherein:

X is an amino protecting group of the structure

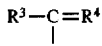

where $R^3$ is selected from the group consisting of hydrogen, alkyl, alkenyl, alkynyl, alkoxy, aralkoxy, and amino and $R^4$ is oxygen or sulfur, Y is an amino acid residue, Z is a spacer sequence selected from the group consisting of aliphatic diamines of 1 to 6 carbon atoms, $[R^6]_m$, and mixtures thereof, wherein $R^6$ is an amino acid residue and m is an integer greater than or equal to 1, n is 0 or 1, and T is a therapeutic agent, and $\alpha$ is 0 or 1;

and wherein the chemotactic peptide substantially accumulates at the site of infection or inflammation and does not substantially accumulate at a site that is not infected or inflamed.

71. The therapeutic composition of claim 70 wherein $\alpha$ is 1 and T is selected from the group consisting of drugs, lectins, toxins, antimicrobial agents, and moieties of the structure:

$$-|K|_v-|M^2|_\mu$$

wherein:

K is an intermediary functional group, v is 0 or 1, $M^2$ is a therapeutic radioisotope, and $\mu$ is 0 or 1.

72. The therapeutic composition of claim 71 wherein v is 0.
73. The therapeutic composition of claim 72 wherein $M^2$ is selected from the group consisting of $^{125}$I, $^{131}$I, $^{90}$Y, $^{67}$Cu, $^{217}$Bi, $^{211}$At, $^{212}$Pb, $^{47}$Sc, $^{186}$Re, $^{188}$Re, $^{105}$Rh, $^{153}$Sm, and $^{109}$Pd.

* * * * *

UNITED STATES PATENT AND TRADEMARK OFFICE
CERTIFICATE OF CORRECTION

PATENT NO. : 5,792,444
DATED : August 11, 1998
INVENTOR(S) : Fischman et al.

It is certified that error appears in the above-identified patent and that said Letters Patent is hereby corrected as shown below:

Title page,
Page 1, left column,
Line 4, of item [63], ("Related U.S. Application Data"), please delete "May 4, 1989" and insert therein -- May 9, 1989 --.
After line 24, of item [56], ("References cited") please insert -- 823633 4/83 Finland. --.
Above line 25, of item [56], ("References cited") please insert -- 870122 7/88 Finland. --.

Page 2, left column, Under the heading "Other Publications",
Line 12, please delete "Absract" and insert therein -- Abstract --.
Line 45, please delete "Multile" and insert therein -- Multiple --.
Line 46, please delete "(Mar. 1995)" and insert therein -- (Mar. 1955) --.

Page 2, right column, under the heading "Other Publications",
Line 1, after "Freer, R.J." please insert -- et al. --.
Line 10, please delete "Peptides" and insert therein -- Peptide --.
Line 42, please delete "Indium-11-" and insert therein -- Indium-111 --.
Line 51, please delete "9399" and insert therein -- 939 --.
Line 11, please delete "Reduction of Acids to Alcohols:" and insert therein -- "Reduction of Acids to Alcohols-" --.

Page 3, left column, under the heading "Other Publications",
Line 52, please delete "(1985)." and insert therein -- (1975). --.
Line 8, please delete "(Suppl.)" and insert therein -- (Suppl. 5) --.
Line 27, please delete "Chemoattrctants" and insert therein -- Chemoattractants --.

Page 3, right column, under the heading "Other Publications",
Line 33, please delete "Neurophils" and insert therein -- Neutrophils --.
Line 46, please delete "Neotrophiles" and insert therein -- Neutrophiles --.
Line 53, please delete "Acylated" and insert therein -- "Acylated --.
Last line after "Antagonists." please insert -- " --.

UNITED STATES PATENT AND TRADEMARK OFFICE
CERTIFICATE OF CORRECTION

PATENT NO. : 5,792,444  
DATED : August 11, 1998  
INVENTOR(S) : Fischman et al.

It is certified that error appears in the above-identified patent and that said Letters Patent is hereby corrected as shown below:

Column 1,  
Line 8, after "1993," please insert -- now --.  
Line 10, please delete "May 4, 1989" and insert therein -- May 9, 1989 --.

Column 3,  
Line 43, please delete *"Nonsef and insert* therein -- *Nonself* --.

Column 6,  
Line 16, after "and" please insert -- Rz is —S—, --.  
Line 20, af- "$-\overset{\overset{O}{\|}}{S}-$" ter please insert -- or —O— --.

Column 8,  
Line 46, please delete "four" and insert therein --three--.  
Line 47, after "blood" please insert -- (FIG. 10A) --.  
Line 47, after "lung" please insert -- (FIG. 10B) --.  
Line 47, after "liver" please insert -- (FIG. 10C) --.  
Line 47, after "spleen" please insert -- (FIG. 10D) --.  
Line 47, after "kidney" please insert -- (FIG. 10E) --.  
Line 48, after "GI-tract" please insert -- (FIG. 10F) --.  
Line 56, after "(ng/kg)" please insert -- (FIGS. 12A-12D) --.  
Line 59, after "3" please insert -- hours (FIG. 13A) --.  
Line 59, please delete "12 hours" and insert therein -- 15 hours (FIG. 13B) --.  
Line 65, after "HP" please insert -- (FIG. 14A) --.  
Line 65, after "labeled" please insert -- (FIG. 14B) --.

Column 9.  
Line 27, please delete "form" and insert therein -- from --.  
Line 39, please delete "animals. e.g." and insert therein -- animals, e.g., --.

Column 9 and 10,  
In the title of the schematic diagram, please delete "Derivitization" and insert therein -- Derivatization --.

Column 11,  
Line 6, after "f." please insert -- 1. --.  
Line 49, please delete "of-the" and insert therein -- of the --.

UNITED STATES PATENT AND TRADEMARK OFFICE
CERTIFICATE OF CORRECTION

PATENT NO. : 5,792,444
DATED : August 11, 1998
INVENTOR(S) : Fischman et al.

It is certified that error appears in the above-identified patent and that said Letters Patent is hereby corrected as shown below:

Column 13,
Line 42, after "and" please insert -- $R_2$ is —S—, --.

Line 45, after "$-\overset{\overset{O}{\|}}{S}-$" please insert -- or —O— --.

Column 14,
Line 61, after "Isot." please delete ".".

Column 16,
Line 35, please delete "$SnCl_2.2H_2O$" and insert therein-- $SnCl_2 \cdot 2H_2O$ --.

Column 17,
Line 15, please delete "$N^6$" and insert therein -- $N^\varepsilon$ --.

Column 18,
Line 13, please delete "norieucyl" and insert therein -- norleucyl --.

Columns 23 and 24, within Table 1
Example 27, please delete "N-butlyurea-MLF-Lys-SHNH" and insert therein
-- N-butylurea-MLF-Lys-SHNH --
Example 29, please delete "i-proplyurea-MLF-Lys-Asp-SHNH" and insert
therein -- i-propylurea-MLF-Lys-Asp-SHNH --.
Example 31 "i-propylurea-MLF-n-propyldiamine-Asp-SHNH", under the column
heading "Adhesion Agonist $EC_{50}, \mu M$", please delete " 1,1 " and insert therein -- 1.1 --.
Example 32 "i-propylurea-MLF-Lys-SHNH-Boc", under the column heading "Adhesion
Antagonist $IC_{50}, \mu, M$", please insert -- - --.

Columns 25 and 26, within Table 1,
Example 91, please delete 4-carboxy-thiazoidine-MLF" and insert therein
-- 4-carboxy-thiazolidine-MLF --.

Column 29,
Line 46, Please delete "*E. coli*infected" and insert therein -- *E. coli* infected --.

Columns 33 and 34,
Line 1, within Table III heading, please delete "$^{99mm}Tc$" and insert therein -- $^{99m}Tc$ --.
Line 15, within Table III, under "Liver 60 (mins.) HP2" please delete "0.S0 ± 0.022"
and insert therein -- 0.50 ± 0.022 --.

UNITED STATES PATENT AND TRADEMARK OFFICE
CERTIFICATE OF CORRECTION

PATENT NO.  : 5,792,444
DATED       : August 11, 1998
INVENTOR(S) : Fischman et al.

It is certified that error appears in the above-identified patent and that said Letters Patent is hereby corrected as shown below:

Column 34,
Line 64, please delete "H P3" and insert therein -- HP3 --.

Column 35,
Line 54, after "shown" please insert -- in --.

Column 36,
Line 47, please delete "$EC_{50}$'s" and insert therein -- $EC_{50}$'s --.

Column 37,
Line 66, please delete "these four" and insert therein -- three --.

Column 39,
Line 31, please delete "dimethformamide" and insert therein -- dimethylformamide --.

Column 41,
Line 41, after "1,000 ng/kg)," please insert -- (FIGS. 12A and 12B, respectively) --.
Line 51, after "dose" please insert -- (FIG. 12C) --.
Line 56, after "(10 ng/kg)" please insert -- (FIG. 12D) --.
Line 65, after "3" please insert -- hours (FIG. 13A) --.
Line 65, after "15 hours" please insert -- (FIG. 13B) --.

Column 43,
Line 43, please delete "thispeptide" and insert therein -- this peptide --.

Column 47,
Line 2, please delete "(p<0,05)" and insert therein -- ($p<0.05$) --.

Column 48 Claim 2,
Line 54 please delete "—CHZ—$CH_2$13$R^2$—$CH_3$" and insert therein
-- —$CH_2$—$CH_2$—$R^2$—$CH_3$ --,
Line 54, after "and" please insert -- $R^2$ is —S—, --.

Line 57, after "—$\overset{\overset{O}{\|}}{S}$—" please insert -- or —O— --.

UNITED STATES PATENT AND TRADEMARK OFFICE
CERTIFICATE OF CORRECTION

PATENT NO. : 5,792,444
DATED : August 11, 1998
INVENTOR(S) : Fischman et al.

It is certified that error appears in the above-identified patent and that said Letters Patent is hereby corrected as shown below:

<u>Column 49 Claim 7,</u>
Line 29, please delete "X—Met—Leu—Phe—$[Z]_v$—W" and insert and insert therein
-- X—Met—Leu—Phe$[Z]_n$—W --.

<u>Column 52 Claim 53,</u>
Line 38, please delete "X—Y—Leu—Phe—$[Z]_v$—W" and insert therein
-- X—Met—Leu—Phe—$[Z]_n$—W --.
Line 41, please delete "—$[K]_\mu$—$M^1$" and insert therein -- —$[K]v$—$M^1$ --.

Signed and Sealed this

Thirtieth Day of October, 2001

Attest:

*Attesting Officer*

NICHOLAS P. GODICI
*Acting Director of the United States Patent and Trademark Office*